United States Patent
Stocki et al.

(10) Patent No.: US 11,512,136 B2
(45) Date of Patent: Nov. 29, 2022

(54) TRANSFERRIN RECEPTOR (TFR)-SELECTIVE BINDING PEPTIDES CAPABLE OF CROSSING THE BLOOD BRAIN BARRIER AND METHODS OF USE THEREOF

(71) Applicant: Ossianix, Inc., Philadelphia, PA (US)

(72) Inventors: Pawel Stocki, Royston (GB); Krzysztof Bartlomiej Wicher, Cambridge (GB); Jaroslaw Michal Szary, Stevenage (GB); Julia Lynn Rutkowski, Bryn Mawr, PA (US)

(73) Assignee: Ossianix, Inc., Philadelphia, PA (US)

( * ) Notice: Subject to any disclaimer, the term of this patent is extended or adjusted under 35 U.S.C. 154(b) by 181 days.

(21) Appl. No.: 16/761,190

(22) PCT Filed: Oct. 27, 2018

(86) PCT No.: PCT/US2018/057887
§ 371 (c)(1),
(2) Date: May 1, 2020

(87) PCT Pub. No.: WO2019/089395
PCT Pub. Date: May 9, 2019

(65) Prior Publication Data
US 2021/0403591 A1    Dec. 30, 2021

Related U.S. Application Data

(60) Provisional application No. 62/624,107, filed on Jan. 30, 2018, provisional application No. 62/580,453, filed on Nov. 2, 2017, provisional application No. 62/580,934, filed on Nov. 2, 2017.

(51) Int. Cl.
*C07K 16/28* (2006.01)
*A61K 47/68* (2017.01)

(52) U.S. Cl.
CPC ...... *C07K 16/2881* (2013.01); *A61K 47/6849* (2017.08); *C07K 2317/565* (2013.01); *C07K 2317/567* (2013.01); *C07K 2317/92* (2013.01); *C07K 2319/00* (2013.01)

(58) Field of Classification Search
CPC .......... C07K 16/2881; C07K 2317/565; C07K 2317/567; C07K 2317/92; C07K 2319/00; A61K 47/6849
See application file for complete search history.

(56) References Cited

U.S. PATENT DOCUMENTS

| 10,479,990 | B2 | 11/2019 | Häsler et al. |
| 10,722,576 | B2 | 7/2020 | Häsler et al. |
| 2019/0175746 | A1 | 6/2019 | Stocki et al. |
| 2020/0115702 | A1 | 4/2020 | Häsler et al. |
| 2020/0316195 | A1 | 10/2020 | Häsler et al. |

FOREIGN PATENT DOCUMENTS

| WO | 2006068867 | A1 | 6/2006 |
| WO | 2007140371 | A2 | 12/2007 |
| WO | 2012075037 | A1 | 6/2012 |
| WO | 2014033074 | A1 | 3/2014 |
| WO | 2015200883 | A2 | 12/2015 |
| WO | 2016077840 | A2 | 5/2016 |
| WO | 2016094566 | A2 | 6/2016 |
| WO | 2016207240 | A1 | 12/2016 |
| WO | 2018031424 | A1 | 2/2018 |

OTHER PUBLICATIONS

Clark E, et al. (2022) Pharmaceutics 14:1335 (16 pages).*
Abbott, N Joan et al. "Structure and function of the blood-brain barrier." Neurobiology of disease vol. 37,1 (2010): 13-25.
Ahmad, et al., (2012). scFv antibody: principles and clinical application. Clinical & developmental immunology, 2012, 980250.
Alata, W., et al, (2014). "Brain uptake of a fluorescent vector targeting the transferrin receptor: a novel application of in situ brain perfusion." Mol Pharm 11(1): 243-253.
Bien-Ly, N., et al., (2014). "Transferrin receptor (TfR) trafficking determines brain uptake of TfR antibody affinity variants." J Exp Med 211(2): 233-244.
Boado et al., "Engineering and expression of a chimeric transferrin receptor monoclonal antibody for blood-brain barrier delivery in the mouse" Biotechnol Bioeng. Mar. 1, 2009;102(4):1251-8.
Boje, K. M. (1996). "Inhibition of nitric oxide synthase attenuates blood-brain barrier disruption during experimental meningitis." Brain Res 720(1-2): 75-83.
Cheng, Y., et al., (2004). "Structure of the human transferrin receptor-transferrin complex." Cell 116(4): 565-576.
Couch, J. A., et al., (2013). "Addressing safety liabilities of TfR bispecific antibodies that cross the bloodbrain barrier." Sci Transl Med 5(183): 183ra157, 181-112.
Crépin et al., Cancer Res., Jul. 1, 2019;70(13): 5497-506.
de Vries, et al., "Effect of endotoxin on permeability of bovine cerebral endothelial cell layers in vitro," J. Pharmacol. Exp. Ther. (1996), 277(3): 1418-1423.
Demeule, M., et al., (2014). "Conjugation of a brain-penetrant peptide with neurotensin provides antinociceptive properties." J Clin Invest 124(3): 1199-1213.
Demogines A, et al., (2013) "Dual hostvirus arms races shape an essential housekeeping protein" PLoS Biol. 11(5): e1001571.

(Continued)

*Primary Examiner* — Robert S Landsman
(74) *Attorney, Agent, or Firm* — KDB Firm PLLC

(57) ABSTRACT

The present invention relates to the fields of molecular medicine and targeted delivery of therapeutic or diagnostic agents to cells outside the vascular system and into the parenchymal tissue of organs within the body. More specifically, the present invention relates to improved TfR-binding moieties based on shark VNARs capable of crossing the blood brain barrier (BBB) and capable of carrying and releasing cargo specifically targeted to the parenchymal tissue of the brain.

16 Claims, 23 Drawing Sheets

Specification includes a Sequence Listing.

(56) References Cited

OTHER PUBLICATIONS

Forejtnikovà, Hana et al. "Transferrin receptor 2 is a component of the erythropoietin receptor complex and is required tor efficient erythropoiesis." Blood vol. 116,24 (2010): 5357-67.

Friden et al., "Anti-transferring receptor antibody and antibody-drug conjugates cross the blood-brain barrier," (Jun. 1991) Proc. Natl. Acad. Sci., 88 (11):4771-5.

Hasler, J., et al. (2016). "VNAR single-domain antibodies specific for BAFF inhibit B cell development by molecular mimicry." Mol Immunol 75: 28-37.

Jefferies, et al., "Authentic T helper CD4 (W3/25) antigen on rat peritoneal macrophages," J.Exp.Med., vol. 162, Jul. 1985, pp. 117-127.

Jones, A. R., & Shusta, E. V. (2007). Blood-brain barrier transport of therapeutics via receptor-mediation. Pharmaceutical research, 24(9), 1759-1771.

Lawrence CM, Ray S, Babyonyshev M, Galluser R, Borhani DW, et al. Crystal structure of the ectodomain of human transferrin receptor. Science. Oct. 22, 1999;286(5440):779-82.

Mayhan, W. G. (1998). "Effect of lipopolysaccharide on the permeability and reactivity of the cerebral microcirculation: role of inducible nitric oxide synthase." Brain Res 792(2): 353-357.

Moos, T. and E. H. Morgan (2001). "Restricted transport of anti-transferrin receptor antibody (OX26) through the blood-brain barrier in the rat" J Neurochem 79(1): 119-129.

Niewoehner J, et al. (2014) "Increased brain penetration and potency of a therapeutic antibody using a monovalent molecular shuttle." Neuron. 81(1):49-60.

Pardridge, William M. "Drug transport across the blood-brain barrier." Journal of cerebral blood flow and metabolism : official journal of the International Society of Cerebral Blood Flow and Metabolism vol. 32,11 (2012): 1959-72.

Pardridge, W. M., & Boado, R. J. (2012). Reengineering biopharmaceuticals for targeted delivery across the blood-brain barrier. Methods in enzymology, 503, 269-292.

Pasqualini, R. and E. Ruoslahti (1996). "Organ targeting in vivo using phage display peptide libraries." Nature 380 (6572): 364-366.

Shukla, A., M. Dikshit and R. C. Srimal (1995). "Nitric oxide modulates bloodbrain barrier permeability during infections with an inactivated bacterium." Neuroreport 6(12): 1629-1632.

Silvestri et al., "The extrahepatic role of TFR2 in iron homeostasis" Front. Pharmacol., May 7, 2014, 6 pages.

Stanfield, R. L., H. Dooley, P. Verdino, M. F. Flajnik and I. A. Wilson (2007). "Maturation of shark single-domain (IgNAR) antibodies: evidence for induced-fit binding." J Mol Biol 367(2): 358-372.

Triguero, D., et al., (1990). "Capillary depletion method for quantification of blood-brain barrier transport of circulating peptides and plasma proteins." J Neurochem 54(6): 1882-1888.

Tuma, P., & Hubbard, A. L. (2003). Transcytosis: crossing cellular barriers. Physiological reviews, 83(3), 871-932. https://doi.org/10.1152/physrev.00001.2003.

Weber et al. (2018) "Brain Shuttle Antibody for Alzheimer's Disease with Attenuated Peripheral Effector Function due to an Inverted Binding Mode", Cell Reports 22, 149-162 Jan. 2, 2018.

Weiner, et al., (2012). Antibody-based immunotherapy of cancer. Cell, 148(6), 1081-1084. https://doi.org/10.1016/j.cell.2012.02.034.

Williams, S. K., et al., (1980). "Isolation and Characterization of Brain Endothelial Cells: Morphology and Enzyme Activity." Journal of Neurochemistry 35(2): 374-381.

Yu, Y. J., et al., (2011). "Boosting brain uptake of a therapeutic antibody by reducing its affinity for a transcytosis target." Sci Transl Med 3(84): 84ra44.

\* cited by examiner clone H variants that showed binding to mTfR1

| | 1 | 2 | 3 | 4 | 5 | 6 | 7 | 8 | 9 | 10 | 11 | 12 | 13 |
|---|---|---|---|---|---|---|---|---|---|---|---|---|---|
| clone C | V | Q | Y | P | S | Y | N | N | Y | X | F | W | C |
| clone H | Q | Q | F | P | S | S | S | N | G | R | Y | W | C |

FIG. 13

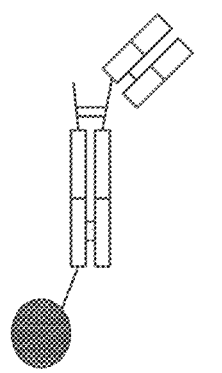
Fc1C
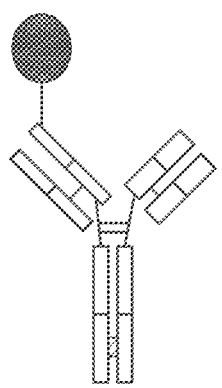
HC1N
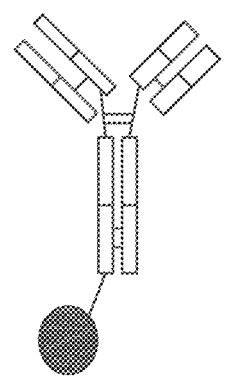
HC1C
HC2N
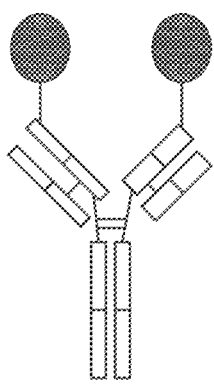
LC2N
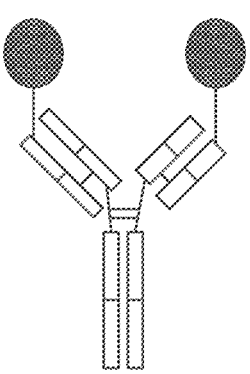
HC2C
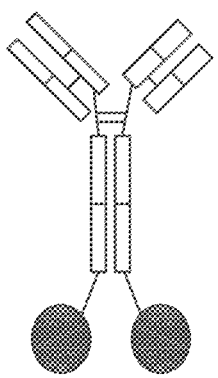
LC2C
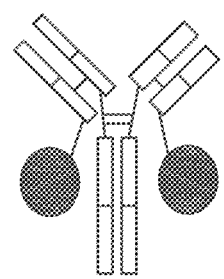
FIG.14

| | |
|---|---|
| sp\|P02786\|TFR1_HUMAN | SKVWRDQHFVKIQVKDSAQNSVIIVDKNGRLVYLVENPGGYVAYSKAATVTGKLVHANFG |
| sp\|Q62351\|TFR1_MOUSE | SKVWRDEHYVKIQVKSSIGQNMVTIVQSNGNLDPVESPEGYVAFSKPTEVSGKLVHANFG |
| sp\|P02786\|TFR1_HUMAN | TKKDFEDLYTPVNGSIVIVRAGKITFAEKVANAESLNAIGVLIYMDQTKFPIVNAELSFF |
| sp\|Q62351\|TFR1_MOUSE | TKKDFEELSYSVNGSLVIVRAGEITFAEKVANAQSFNAIGVLIYMDKNKFPVVEADLALF |
| sp\|P02786\|TFR1_HUMAN | GHAHLGTGDPYTPGFPSFNHTQFPPSRSSGLPNIPVQTISRAAAEKLFGNMEGDCPSDWK |
| sp\|Q62351\|TFR1_MOUSE | GHAHLGTGDPYTPGFPSFNHTQFPPSQSGLPNIPVQTISRAAAEKLFGKMEGSCPARWN |
| sp\|P02786\|TFR1_HUMAN | TDSTCRMVTSESKNVKLTVSNVLKEIKILNIFGVIKGFVEPDHYVVVGAQRDAWGPGA-A |
| sp\|Q62351\|TFR1_MOUSE | IDSSCKLELSQNQNVKLTVSNVLKEIKILNIFGVIKGYEEPDRYVVVGAQRDALGAGVAA |

FIG. 20

TRANSFERRIN RECEPTOR (TFR)-SELECTIVE BINDING PEPTIDES CAPABLE OF CROSSING THE BLOOD BRAIN BARRIER AND METHODS OF USE THEREOF

CROSS REFERENCE TO RELATED APPLICATION

This application is a national stage filing under 35 U.S. § 371 of Intl. Appln. No. PCT/US2018/057887, filed Oct. 27, 2018, which claims the benefit of provisional applications U.S. Ser. No. 62/580,453; filed Nov. 2, 2017; U.S. Ser. No. 62/580,934; filed Nov. 2, 2017; and U.S. Ser. No. 62/624,107; filed Jan. 30, 2018, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 1, 2020, is named OSX1701-US4_SL.txt and is 37,531 bytes in size.

FIELD OF THE INVENTION

The present invention relates to improved peptides that bind with high specificity and functionally interact with the transferrin receptor ("TfR") and with improved ability to cross the blood brain barrier (BBB). Such TfR-binding moieties may be used alone or as components in specific conjugates that target the transferrin/transferrin receptor transport system. The invention relates more specifically to VNAR single chain antibodies derived from nurse shark that bind to TfR, compounds and compositions comprising a TfR-specific binding moiety, diagnostic and therapeutic methods of use in vitro or in vivo, e.g., to diagnose, treat and/or prevent a pathological condition, disorder or disease in which it is beneficial to deliver a heterologous biomolecule across the blood brain barrier by association with a TfR-specific VNAR binding moiety. Other uses for TfR-specific binding moieties of the invention include, e.g., regulating the interaction of iron-charged transferrin with TfR (receptor cycling or cell surface presentation), such as may be therapeutic in treatment of certain cancer cells and tumors of various tissue types.

BACKGROUND OF THE INVENTION

The blood-brain barrier (BBB) is the principal interface between blood and the interstitial fluid that bathes neurons within the brain parenchyma (Abbott et al., Neurobiol Dis. 2010 January; 37(1):13-25). The BBB is formed by highly specialized endothelial cells that maintain an optimal environment for neuronal function by eliminating toxic substances and supplying the brain with nutrients and other metabolic requirements. The BBB likewise presents a formidable obstacle for the systemic delivery of many potentially important therapeutic and diagnostics agents. With the exception of small, lipophilic molecules (MW less than 500 Daltons), which can cross the BBB by transmembrane diffusion, nearly all hydrophilic small molecules, peptides, proteins, RNAs and genetic vectors that could be of therapeutic value are excluded (Pardridge, J Cereb Blood Flow Metab. 2012 November; 32(11):1959-72.). For example, many of the antibodies designed to treat a variety of neurodegenerative disorders including Alzheimer's disease, Parkinson's disease, Huntington's disease and frontotemporal dementia will be limited by their inability to reach the pathological target within the brain. Thus, despite tremendous progress in the discovery of potential therapeutics for CNS diseases, successful development is hindered without an effective means of delivery across the BBB.

Although the BBB restricts the passage of many substances, brain capillaries use membrane transport systems to deliver nutrients and macromolecules important for normal brain function. The main route for large molecules, such as proteins and peptides, to enter the CNS is by receptor-mediated transcytosis (RMT) which might also be used to shuttle a wide range of therapeutics into the brain in a non-invasive manner (Jones and Shusta, Pharm Res. 2007 September; 24(9):1759-71). Circulating ligands such as transferrin, insulin and leptin interact with specific receptors concentrated on the luminal side of the brain capillary endothelial cells. Once bound to the receptor, the process of endocytosis is initiated as the receptor-ligand complexes cluster and intracellular transport vesicles detach from the membrane (Tuma and Hubbard, Physiol Rev. 2003 July; 83(3):871-932). The transport vesicles containing receptor-ligand complexes or dissociated ligands are directed away from the lysosomal compartment and trancytosed to the brain interstitial side of the endothelial cell, where they are released without disrupting the BBB.

The transferrin receptor 1 (TfR-1) endocytotic pathway for iron homeostasis has been one of the most extensively characterized systems for drug delivery across the BBB. TfR-1 mediates influx of iron-loaded transferrin from blood to brain in addition to the transcytosis of iron-depleted transferrin in the reverse direction. Transferrin itself has been used as a vehicle for brain delivery, but transferrin conjugates have to compete for the receptor with the high plasma concentration of the endogenous ligand. The OX-26 mouse monoclonal antibody, which specifically binds the rat transferrin receptor in brain capillaries without blocking the binding of transferrin (Jefferies et al., 1985), was the first antibody used to carry a drug cross the BBB (Freiden et al., Proc Natl Acad Sci USA. 1991 Jun. 1; 88(11):4771-5).

Anti-TfR antibodies have since been modified in a several different ways to deliver heterologous biomolecules, e.g., a drug cargo, to the brain. Potential biotechnology products, including lysosomal enzymes, neurotrophins, decoy receptors and antibody fragments, have been fused to the carboxyl terminus of the Fc domain of TfR for CNS delivery (Pardrige and Boado, Methods Enzymol. 2012; 503:269-92). More recently, bispecific antibodies have been produced by knobs-into-holes technology whereby one half of the antibody binds the CNS target and the other binds the TfR-1 (Yu et al., Sci Transl Med. 2011. 3(84):84ra44). Bispecific antibodies have also been generated by fusing the ScFv portion of a TfR-1 antibody to the carboxyl terminus of a therapeutic antibody (Niewoehner et al., Neuron. 2014 Jan. 8; 81(1):49-60) which maintains avid binding to the target. Each of these approaches has provided evidence of CNS activity in animal models following the intravenous injection, indicating that TfR-1 antibodies hold significant promise as therapeutic carriers for the non-invasive treatment of CNS disorders.

Despite these advances, several features of monoclonal antibodies as BBB carriers have hampered their translation from animal to humans. Antibodies are large molecules composed of 4 disulfide-linked subunits that are challenging to format as bispecific molecules. Moreover, functional components outside the antigen recognition domain can lead to off-mechanism toxicity, and complement-mediated lysis of TfR-rich reticulocytes has been reported (Couch et al., Sci Transl Med. 2013 May 1; 5(183):183ra57, 1-12). Another drawback is that TfR antibodies used to date are species-specific, which is problematic for preclinical safety testing of potential therapeutic molecules. Surrogate antibodies to TfR-1 with the same biochemical properties (binding epitope, affinity, avidity and pH sensitivity) and transcytosis activity will be difficult to identify. Moreover, antibodies that block ligand binding (Crépin et al., Cancer Res. 2010 Jul. 1; 70(13):5497-506), inhibit transcytosis or deplete surface receptors (Bien-Ly et al., J Exp Med. 2014 Feb. 10; 211(2):233-44) would be unsuitable as BBB carriers due to potential iron deprivation.

To address the drawbacks inherent in full size antibodies as BBB carriers, a panel of species cross-reactive VNARs to TfR-1 were identified by phage display and selected for brain uptake. VNARs are isolated variable domains derived from the naturally-occurring single chain antibodies found in the shark (Stanfiled et al., Science. 2004 Sep. 17; 305 (5691):1770-3.). Their small size (~12 kDa), high solubility, thermal stability and refolding capacity (Wesolowski et al., Med Microbiol Immunol. 2009 August; 198(3):157-74) simplifies coupling to a monoclonal antibody or other pharmaceutical. Their modularity offers a wide range of therapeutic design and species cross-reactivity facilitates the development and clinical translation of brain penetrant therapeutics to treat a broad spectrum of CNS disorders.

Recently developed methods for in vivo enrichment and isolation of peptides capable of crossing the BBB, described in PCT/US2017/045592, filed Aug. 4, 2017 (now WO2018/031424), yielded VNARs that binds to human and mouse TfR-1 and are capable of penetrating the BBB. When formatted as an Fc-fusion, one clone (Clone C; also referred to as Clone 10 in the WO2018/031424) crossed the BBB and reached a concentration of 5 nM in murine whole brain tissue and is the most potent shuttle to TfR-1 identified to date. The next most potent clone reached a concentration of 0.7 nM (Clone H and shown as Sequence 169 in WO2018/031424).

Both clones cross the BBB at low therapeutic doses (2 mg/kg), are rapidly taken up into the brain (with 1 hr), continue to accumulate over several days and slowly decline over the next week after a single IV injection. These profiles markedly contrast with other BBB shuttles to the TFR1, which are rapidly cleared by the liver (Biotechnol. Bioeng. 2009. 102(4):1251-1258; Neuron 2014. 81(1):49-60) or require very high doses (e.g., 50 mg/kg, Genentech, Yu et al. Sci. Transl. Med. 3:84ra44 (2011)).

Clone C and Clone H differ structurally from other TfR shuttles in that each contains a VNAR domain derived from a shark single chain antibody rather than from a monoclonal antibody or scFv fragment. VNARs bind antigens predominantly through a single CDR3 region, which is much longer than CDRs in monoclonal antibodies. The more focused binding paratope of the VNAR is able to seek out small epitopes on antigens that are inaccessible to the large binding paratope of monoclonal antibodies. In the case of TfR-1, VNARs were able to access short regions of homology in surface exposed region in both the mouse and human versions of the receptor. To date there are no species cross-reactive monoclonal antibodies to TfR-1, except those that bind the highly homologous transferrin binding site. Such conventional-type antibodies block the transport iron-carrying transferrin, cause severe cytotoxicity and are not suitable for therapeutic use.

The ability to generate species cross-reactive binders is important for two reasons. Numerous antibodies can be generated to TfR-1, but very few cross the BBB. With a pool of cross-reactive binders, it is possible to select VNARs that are highly brain penetrant in mice but that also retain binding to the identical site in the human receptor, for example as reported herein. This not only increases the probability of discovering rare, highly functional binders but makes them suitable for clinical use in humans.

Nevertheless, the need remains for new additional molecules that selectively deliver compounds such as biomolecules (e.g., therapeutics and diagnostics) across membrane systems in mammalian subject, such as into various organs, tumors or across the BBB. Moreover, it would be advantageous to have new selective TfR-specific binding compounds, especially ones having one or more advantageous biological properties with therapeutic and/or diagnostic benefit over current anti-TfR antibodies and other regulators of iron transport systems. The present invention addresses this need through restricted random mutagenesis of CDR3 of the TfR-1 binding paratope of Clone C and Clone H. These variants provide further sequence variations that confer additional advantages for brain uptake and therapeutic development.

SUMMARY OF THE INVENTION

The present invention provides a family of Clone C and Clone H variants that are TfR-specific binding moieties and comprise a VNAR domain capable of specifically binding to human TfR-1 without substantially interfering with transferrin binding to and/or transport by human TfR-1 and capable of crossing the blood brain barrier. In some embodiments, these variants exhibit species cross reactivity with murine TfR-1

More particularly, and encompassing the Clone C and Clone H variants disclosed herein, the present invention further provides isolated TfR-specific binding moieties comprising a VNAR scaffold represented by the formula, from N to C terminus,

FW1-CDR1-FW2-HV2-FW2'-HV4-FW3-CDR3-FW4, wherein the CDR1 region consists of a peptide having an amino acid sequence of formula DSNCALS (SEQ ID NO. 2) or DSNCELS (SEQ ID NO. 7), wherein the CDR3 region consists of a peptide having an amino acid sequence of formula $$X_1\text{-}Q\text{-}X_2\text{-}P\text{-}X_3\text{-}X_4\text{-}X_5\text{-}X_6\text{-}X_7\text{-}X_8\text{-}X_9\text{-}W\text{-}C\text{-}D\text{-}V, \quad \text{(SEQ ID NO. 11)}$$

wherein
$X_1$ is A, L, Q or V,
$X_2$ is F, H, R, S, W or Y,
$X_3$ is F, H, N, Q, R, S, T or V,
$X_4$ is H, I, L, N, P, Q, R, S, T, W or Y,
$X_5$ is D, E, F, G, H, N, P, Q, R, S, T or W,
$X_6$ is H, N, P, R or S,
$X_7$ is A, F, G, H, L, P, or Y,
$X_8$ is R or absent, and
$X_9$ is F or Y; and
wherein the moiety is capable of specifically binding to human TfR-1 without substantially interfering with transferrin binding to and/or transport by human TfR-1, and is capable of crossing the blood brain barrier, with the proviso that the VNAR scaffold does not have an amino acid sequence of (Clone C; SEQ ID NO. 1)
ARVDQTPQTITKETGESLTINCVLRDSNCALSSTYWYRKKSGSTNEENIS

KGGRYVETVNSGSKSFSLRINDLTVEDSGTYRCNVVQYPSYNNYFWCDVY

GDGTAVTVN
or (Clone H; SEQ ID NO. 6)
ARVDQTPQTITKETGESLTINCVLRDSNCELSSTYWYRKKSGSTNEESIS

KGGRYVETVNSGSKSFSLRINDLVVEDSGTYRCNVQQFPSSSNGRYWCDV

YGGGTAVTVNA.

In embodiments of the foregoing based on the Clone C variants, the TfR-specific binding moieties of the invention comprise a CDR1 region which consists of a peptide having an amino acid sequence of formula DSNCALS (SEQ ID NO. 2), and wherein the amino acids in CDR3 are such that $X_1$ is V, A or L; $X_2$ is Y, H, R, S or W; $X_3$ is S, F, H, Q, R, S, T or V; $X_4$ is Y, H, I, L, N, Q, T or W; $X_5$ is N, D, E, F, H, P, Q, R, S, T or W; $X_6$ is N, H, R or S; $X_7$ is Y, A, H, L or P; $X_8$ is absent; and $X_9$ is F or Y. In some of these embodiments, the TfR-specific binding moieties comprise an FW1-CDR1-FW2-HV2-FW2'-HV4 region with a sequence of ARVDQTPQTITKETGESLTINCVLRDSNCALS STYWYRKKSGSTNEENISKGGRYVET VNSGSKSFSL-RINDLTVEDSGTYRCNV (SEQ ID NO. 4); a CDR3 region with a sequence selected from any one of the CDR3 sequences shown in Table 1 (Clone C variants; SEQ ID NOS. 14-51), and an FW4 region with a sequence of YGDGTAVTVN (SEQ ID NO. 5).

In embodiments based on the Clone H variants, the TfR-specific binding moieties of the invention comprise a CDR1 region which consists of a peptide having an amino acid sequence of formula DSNCELS (SEQ ID NO. 7), and wherein the amino acids in CDR3 are such that $X_1$ is Q or V; $X_2$ is F or W; $X_3$ is S, N or T; $X_4$ is S, R, W or P; $X_5$ is S, W, F, G, N, H, T, or P; $X_6$ is N or P; $X_7$ is G or F; $X_8$ is R; and $X_9$ is Y. In some of these embodiments, the TfR-specific binding moieties comprise have an FW1-CDR1-FW2-HV2-FW2'-HV4 region with a sequence of ARVDQTPQTITKETGESLTINCVLRDSN-CELSSTYWYRKKSGSTNEESISKGGRYVET VNSG-SKSFSLRINDLVVEDSGTYRCNV (SEQ ID NO. 9); a CDR3 region with a sequence selected from any one of the CDR3 sequences shown in Table 6 (Clone H variants; SEQ ID NOS. 55-64); and an FW4 region with a sequence of YGGGTAVTVNA (SEQ ID NO. 10).

Analysis of Clone C, Clone H and their variants establish that their VNAR domains bind to an epitope on human TfR-1 that comprises amino acids NGS at residues 251-253 thereof and to a corresponding epitope on mouse TfR-1 which comprises amino acids NGS at residues 253-255 thereof. Hence in some embodiments of the invention, the TfR-specific binding moieties comprise a VNAR domain capable of specifically binding to human TfR-1 at the NGS epitope without substantially interfering with transferrin binding to and/or transport by human TfR-1 and capable of crossing the blood brain barrier, and have any of the foregoing sequences. In some embodiments, these moieties exhibit species cross reactivity with murine TfR-1.

The TfR-specific binding moieties of the invention are capable of penetrating the brain which, when formatted as Fc fusion proteins and injected into mice at 1.875 mg/kg as described herein, accumulate murine brain homogenates at concentrations ranging from at least about 0.4 nM to about 15 nM, from about 0.8 nM to about 15 nM, from about 1 nM to about 12 nM, or from about 2.5 nM to about 10 nM.

In accordance with the invention, a correlation has been observed between the binding affinity (KD as measured herein) of the TfR-specific binding moiety for its ligand and the brain penetrant ability of the moiety, with higher affinity being correlated with increased brain concentrations. Thus, in some embodiments, the TfR-specific binding moieties of the invention exhibit KDs for human or mouse TfR-1 ranging from about 100 pM to about 50 nM, or from about 200 pM to about 3 nM. In other words, Tfr binders having KDs no greater than 3 nM exhibit unexpectedly good ability to cross the BBB.

In accordance with the invention, a correlation has been observed between the association rate (ka as measured herein) of the TfR-specific binding moiety for its ligand and the brain penetrant ability of the moiety, with higher association rates being correlated with increased brain concentrations. Thus, in some embodiments, the TfR-specific binding moieties of the invention have a ka for human or mouse TfR-1 ranging from about 1.0E+04 1/Ms to about 4.5E+05 1/Ms, or from about 1.2E+04 1/Ms to about 3.5E+05 1/Ms, with a threshold ka value of at least 1.0E+04 1/Ms.

In accordance with the invention, the TfR-specific binding moiety of the invention are formulated as conjugates, including but not limited to, conjugates which comprise a heterologous agent which is a diagnostic or therapeutic agent. In some embodiments, the conjugate comprises one or more of the following agents: a small molecule, peptide or polypeptide, a DNA, RNA, or hybrid DNA-RNA, a traceable marker such as a fluorescent or phosphorescent molecule, a radionuclide or other radioactive agent, an antibody, single chain variable domain, immunoglobulin fragment, variant or fusion, a small molecule diagnostic or therapeutic.

Further embodiments of the invention are directed to nucleic acids encoding the TfR-specific binding moiety or conjugate, as well as vectors and host cells containing those nucleic acids and vectors.

Some embodiments of the invention provide pharmaceutical compositions comprising a TfR-specific binding moiety of the invention or a conjugate thereof.

The instant invention also provides methods of medical treatment, including a method to administer a therapeutically-effective amount of a pharmaceutical composition of the invention to deliver a diagnostic or therapeutic agent to the brain of a mammalian subject in need thereof.

Additional methods of the invention are directed to targeting delivery of a payload to brain parenchymal tissue in a mammal by administering a TfR-specific binding moiety or conjugate of the invention.

Certain embodiments of the invention provide a kit for detecting or quantifying TfR-1 in a sample which comprises at least one TfR-specific binding moiety or conjugate of the invention.

Other embodiments relate to a compound for use as a diagnostic or therapeutic agent in a subject, where the compound comprises a diagnostic or therapeutic agent operably linked to a TfR-specific binding moiety of the invention, and wherein the TfR-specific binding moiety, when formatted as an Fc fusion protein is capable of achieving at least about 0.8 nM in homogenized mouse brain tissue, and upon binding to human TfR-1 in a cell membrane, is endocytosed to thereby deliver said diagnostic or therapeutic agent across the cell membrane. In some embodiments, the concentration of fusion protein ranges from at least about 0.8 nM to about 15 nM, from about 1 nM to about 12 nM, or from about 2.5 nM to about 10 nM. In some embodiments, the operable linkage dissociates after endocytosis to release said diagnostic or therapeutic agent into said cell. In some embodiments, the cell membrane is part of the blood brain barrier or the GI tract.

Another aspect of the invention provides methods of delivering a therapeutic or diagnostic molecule across the blood brain barrier which comprises administering a TfR-specific binding moiety of the invention, wherein said therapeutic molecule is conjugated to said moiety, to a subject for a time and in an amount effective to treat or diagnose a CNS disease or condition.

Another aspect of the invention provides methods of delivering a therapeutic or diagnostic molecule to the gastrointestinal (GI) tract of a subject which comprises administering a TfR-specific binding moiety of the invention, wherein said therapeutic molecule is conjugated to said moiety, to a subject for a time and in an amount effective to treat or diagnose a GI disease or condition.

Further methods of the invention are directed to a method of treatment which comprises administering to a subject in need thereof a compound or composition comprising a TfR-specific binding moiety of the invention. In some embodiments, the disease, disorder or condition is ameliorated upon transport of a heterologous molecule across a cell membrane of a TfR-positive cell, wherein said heterologous molecule comprises or is associated with a TfR-specific binding moiety of the invention. In some embodiments, the TfR-specific binding moiety is internalized by a TfR in a cell membrane associated with the blood brain barrier or the gastrointestinal (GI) tract. In some embodiments, the disease, disorder or condition is a central nervous system disease or condition. In some embodiments, the disease or condition is cancer, and more particularly, a cancer in which the cancer cells express a higher level of TfR relative to equivalent non-cancerous cells.

Yet another aspect of the invention relates to methods of identifying, quantifying or localizing a TfR-containing biological sample or cell which comprises contacting a test sample in vitro or in vivo with a TfR-specific binding moiety of the invention, or a conjugate thereof, and directly or indirectly measuring the TfR-specific binding in or to said sample.

Another embodiment of the invention is directed to targeting delivery of a heterologous molecule to a TfR-expressing cell by delivering a TfR-specific conjugate the invention the target. Another embodiment of the invention is directed a method of increasing the oral bioavailability of a drug by associating the drug with a TfR-specific-binding moiety of the invention.

BRIEF DESCRIPTION OF THE DRAWINGS

FIG. 13. Alignment of Clone C and Clone H CDR3s. Identical residues between the two clones are shaded dark grey and residues with similar side chains are shaded light grey. The (X) in the box at position 10 of Clone C indicates the absence of a corresponding residue.

FIG. 14. Clone C Variant Fusion Proteins. Antibodies with a monovalent VNAR (top row) or bivalent VNARs (bottom row) were genetically fused to a monoclonal antibody via glycine linkers. (Example 5)

FIG. 20. Homology Alignment of Human and Mouse TfR-1 Near Extended Binding Interfaces. The relevant fragment of mouse and human TfR-1 sequences (SEQ ID NOS. 90 and 91, respectively) are aligned and compared for homology. Underlined and bold residues (SK) correspond to binding residues of Clone C identified by cross-linking experiments. The surface residues marked as extended binding interface site of Clone C in FIG. 18 are highlighted in grey.

DETAILED DESCRIPTION OF THE INVENTION

Figure 1:
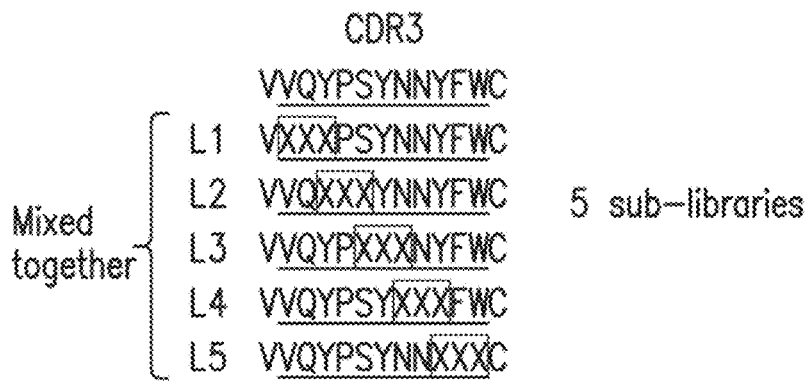
FIG. 1. Phage Library Mutagenesis Design for Clone C. Five phage libraries based on Clone C CDR3 were designed. In each library, three adjacent residues were randomized with one residue overlap between libraries. The phage libraries were pooled together before panning on recombinant human TfR-1. The top line shows the amino acid sequence of the Clone C CDR3 without its last two amino acids (SEQ ID NO. 73) and remaining lines show the sequences of the mutagenized CDR3 sequences used in the five libraries (SEQ ID NOS. 74-78, from top to bottom).

In order that the present invention may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The symbol "#" when used as the column header in any table depicting amino acid or nucleic acid sequences is short hand notation for "SEQ ID NO." and the number thereunder is the actual SEQ ID NO. in the Sequence Listing for the given sequence (unless indicated differently in a specific table).

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "non-human mammal" means a mammal which is not a human and includes, but is not limited to, a mouse, rat, rabbit, pig, cow, sheep, goat, dog, primate, or other non-human mammals typically used in research.

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically-effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

A physiologically-acceptable solution for use in an amount and for a time sufficient to effectively reduce a circulating concentration of the plurality of polypeptides is also referred to herein as a perfusate. The amount of perfusate and time of perfusion depends on the non-human mammal and can be readily determined by those of skill in the art. For example, with a mouse, using a volume of perfusate approximately 10× the blood volume of the mouse is effective at reducing the circulating concentration of polypeptides. Likewise, any volume of perfusate that reduces the circulating concentration of the plurality of polypeptides by about 10%, 25%, 50% or more (relative to the theoretical concentration of the plurality of polypeptides) being delivered is considered effective at reducing the circulating concentration of that plurality.

As used herein, the term "TfR," "TfR1" or "TfR-1" refers to a mammalian transferrin receptor-1 (in context as a protein or a nucleic acid), unless the context indicates that it refers specifically to human TfR-1 (see, e.g., UniProt P02786 TFR1_Human) or mouse TfR-1.

Polypeptide Sequences and Compounds Comprising a TfR Specific VNAR

The present invention provides improved TfR-specific binding moieties based on Clone C and Clone H, two human and mouse TfR-binding VNARs obtained by in vivo selection of brain penetrating phages as described in WO2018/031424.

To improve BBB shuttling function of Clone C and Clone H, each of their CDR3 regions was subjected to a restricted randomization mutagenesis process. For each clone, five new phage libraries were prepared based on the CDR3 with three subsequent residues randomized in each library and with the offset of two residues (FIGS. 1 and 9). The improved Clone C VNAR domains are referred to herein as "Clone C variants" and the improved Clone H VNAR domains are referred to herein as "Clone H variants."

Thus, the present invention provides Clone C and Clone H variants which are TfR-specific binding moieties, e.g., a polypeptide comprising a TfR-binding VNAR; TfR mediated drug vehicles that can carry heterologous molecules across the membrane of a TfR-positive cell. Isolated TfR-binding VNARs are also provided. In certain embodiments, the TfR-specific binding moiety is specific for a mammalian TfR. In certain embodiments, the TfR-binding moiety is specific for human TfR. In certain embodiments, the TfR-specific binding moiety is a component of a BBB vehicle and mediates endocytosis of an associated heterologous molecule across a cell membrane, and in particular, across the BBB. In certain embodiments, the TfR-specific binding moiety is itself or is a component of a TfR antagonist compound which blocks the interaction between TfR, such as hTfR, and one or more of its ligands in vivo. In certain embodiments, the TfR-specific binding moiety mediates endocytosis without blocking ligand binding.

The VNAR domain amino acid sequence for Clone C is

```
                                            (SEQ ID NO. 1)
ARVDQTPQTITKETGESLTINCVLRDSNCALSSTYWYRKKSGSTNEENI

SKGGRYVETVNSGSKSFSLRINDLTVEDSGTYRCNVVQYPSYNNYFWCD

VYGDGTAVTVN.
The CDR1 domain is bolded and italicized; the
CDR3 domain is underlined and bolded.
```

The VNAR domain amino acid sequence for Clone H is

```
                                            (SEQ ID NO. 6)
ARVDQTPQTITKETGESLTINCVLRDSNCELSSTYWYRKKSGSTNEESI

SKGGRYVETVNSGSKSFSLRINDLVVEDSGTYRCNVQQFPSSSNGRYV

VCDVYGGGTAVTVNA.
The CDR1 domain is bolded and italicized; the
CDR3 domain is underlined and bolded.
```

A comparison of the CDR3s of Clone C and Clone H show certain sequence similarities (FIG. 13). These two Type II VNARS are unusual in that the CDR3 cysteine which forms a disulfide with the cysteine in CDR1 is located at the C-terminus rather than the more usual mid-region location of CDR3. The N-terminal portion of CDR3 is highly conserved in both clones. The mid regions of both clones can tolerate substitutions, with the highest degree of diversity found at position 7 and with Clone H able to tolerate an additional amino acid at position 10. In light of the observed sequence similarity between the Clone C and Clone H paratopes, these clones were analyzed for the ability to block each other's binding to mouse or human TfR-1 in a cross-competition ELISA (Table 11). The results clearly indicate that the two clones a share a similar or overlapping binding site. With Clone C's epitope mapped to the NGS at amino acids 251-253 on human TfR-1 (see Examples 6-8 for full discussion) and the similar properties of the variants, these TfR-specific binding moieties constitute a family of molecules that can be represented by a single consensus sequence with respect to CDR3 as well as their ability to bind the same or overlapping epitopes that contain the NGS motif.

Hence, the present invention provides a family of Clone C and Clone H variants that are TfR-specific binding moieties and comprise a VNAR domain capable of specifically binding to human TfR-1 without substantially interfering with transferrin binding to and/or transport by human TfR-1 and capable of crossing the blood brain barrier. In some embodiments, these variants exhibit species cross reactivity with murine TfR-1. In some embodiments these moieties bind the NGS motif of hTfR-1 as described herein.

More particularly, and encompassing the Clone C and Clone H variants disclosed herein, the present invention thus provides isolated TfR-specific binding moieties comprising a VNAR scaffold represented by the formula, from N to C terminus,

FW1-CDR1-FW2-HV2-FW2'-HV4-FW3-CDR3-FW4, wherein the CDR1 region consists of a peptide having an amino acid sequence of formula DSNCALS (SEQ ID NO. 2) or DSNCELS (SEQ ID NO. 7), wherein the CDR3 region consists of a peptide having an amino acid sequence of formula

```
                                          (SEQ ID NO. 11)
        X₁-Q-X₂-P-X₃-X₄-X₅-X₆-X₇-X₈-X₉-W-C-D-V,
``` wherein
$X_1$ is A, L, Q or V,
$X_2$ is F, H, R, S, W or Y,
$X_3$ is F, H, N, Q, R, S, T or V,
$X_4$ is H, I, L, N, P, Q, R, S, T, W or Y,
$X_5$ is D, E, F, G, H, N, P, Q, R, S, T or W,
$X_6$ is H, N, P, R or S,
$X_7$ is A, F, G, H, L, P, or Y,
$X_8$ is R or absent, and
$X_9$ is F or Y; and
wherein the moiety is capable of specifically binding to human TfR-1 without substantially interfering with transferrin binding to and/or transport by human TfR-1, and is capable of crossing the blood brain barrier, with the proviso that the VNAR scaffold does not have an amino acid sequence of

```
                                    (Clone C; SEQ ID NO. 1)
ARVDQTPQTITKETGESLTINCVLRDSNCALSSTYWYRKKSGSTNEENIS

KGGRYVETVNSGSKSFSLRINDLTVEDSGTYRCNVVQYPSYNNYFWCDVY

GDGTAVTVN
or
                                    (Clone H; SEQ ID NO. 6)
ARVDQTPQTITKETGESLTINCVLRDSNCELSSTYWYRKKSGSTNEESIS

KGGRYVETVNSGSKSFSLRINDLVVEDSGTYRCNVQQFPSSSNGRYWCDV

YGGGTAVTVNA.
```

In embodiments based on the Clone C variants, the TfR-specific binding moieties of the invention comprise a CDR1 region which consists of a peptide having an amino acid sequence of formula DSNCALS (SEQ ID NO. 2), and wherein the amino acids in the formula for CDR3 are selected such that
$X_1$ is V, A or L;
$X_2$ is Y, H, R, S or W;
$X_3$ is S, F, H, Q, R, S, T or V;
$X_4$ is Y, H, I, L, N, Q, T or W;
$X_5$ is N, D, E, F, H, P, Q, R, S, T or W;
$X_6$ is N, H, R or S;
$X_7$ is Y, A, H, L or P;
$X_8$ is absent; and
$X_9$ is F or Y.
In some of these embodiments, the TfR-specific binding moieties comprise an FW1-CDR1-FW2-HV2-FW2'-HV4 region with a sequence of ARVDQTPQTITKETGESLTINCVLRDSN-CALSSTYWYRKKSGSTNEENISKGGRYVET VNSG-SKSFSLRINDLTVEDSGTYRCNV (SEQ ID NO. 4); a CDR3 region with a sequence selected from any one of the CDR3 sequences shown in Table 1 (Clone C variants; SEQ ID NOS. 14-51), and an FW4 region with a sequence of YGDGTAVTVN (SEQ ID NO. 5).

In embodiments based on the Clone H variants, the TfR-specific binding moieties of the invention comprise a CDR1 region which consists of a peptide having an amino acid sequence of formula DSNCELS (SEQ ID NO. 7), and wherein the amino acids in the formula for CDR3 are such that $X_1$ is Q or V;
$X_2$ is F or W;
$X_3$ is S, N or T;
$X_4$ is S, R, W or P;
$X_5$ is S, W, F, G, N, H, T, or P;
$X_6$ is N or P;
$X_7$ is G or F;
$X_8$ is R; and
$X_9$ is Y.

In some of these embodiments, the TfR-specific binding moieties comprise have an FW1-CDR1-FW2-HV2-FW2'-HV4 region with a sequence of ARVDQTPQTITKET-GESLTINCVLRDSNCELSSTYWYRKKSGSTNEESI-SKGGRYVET VNSGSKSFSLRINDLVVEDSGTYRCNV (SEQ ID NO. 9); a CDR3 region with a sequence selected from any one of the CDR3 sequences shown in Table 6 (Clone H variants; SEQ ID NOS. 55-64); and an FW4 region with a sequence of YGGGTAVTVNA (SEQ ID NO. 10).

Analysis of Clone C, Clone H and their variants establish that their VNAR domains bind to an epitope on human TfR-1 that comprises amino acids NGS at residues 251-253 thereof and to a corresponding epitope on mouse TfR-1 which comprises amino acids NGS at residues 253-255 thereof. Hence in some embodiments of the invention, the TfR-specific binding moieties comprise a VNAR domain capable of specifically binding to human TfR-1 at the NGS epitope without substantially interfering with transferrin binding to and/or transport by human TfR-1 and capable of crossing the blood brain barrier, and have any of the foregoing sequences. In some embodiments, these moieties exhibit species cross reactivity with murine TfR-1.

Figure 5:
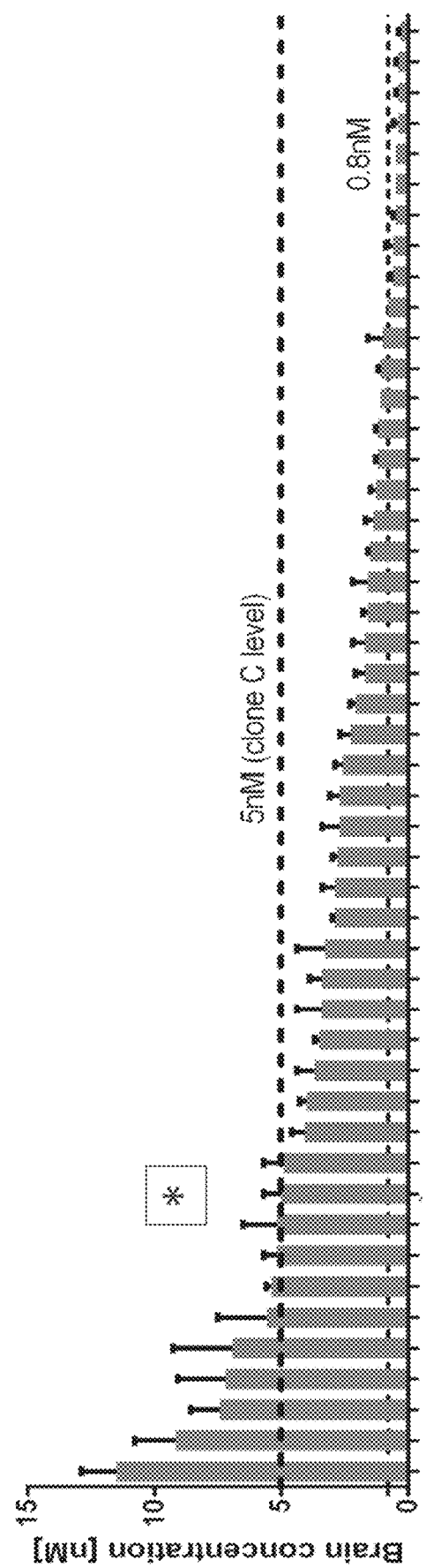
FIG. 5. Brain uptake of Clone C Variants as Fc Fusion Proteins. Clone C variants (47 in total) were generated as bivalent human Fc fusion proteins and tested for brain penetration in mice. The dashed line at 5 nM indicates the brain concentration of Clone C (*) and the dashed line at 0.8 nM indicates the cut-off used for positive effects in this experiment. VNAR-Fcs were administered intravenously to mice at 25 nmol/kg and brains were excised 18 hours later following cardiac perfusion as detailed in the Examples. The VNAR-Fc concentration in brain homogenates was measured by human Fc capture ELISA and the values represent the mean±SD, N=3/group.
Figure 12:
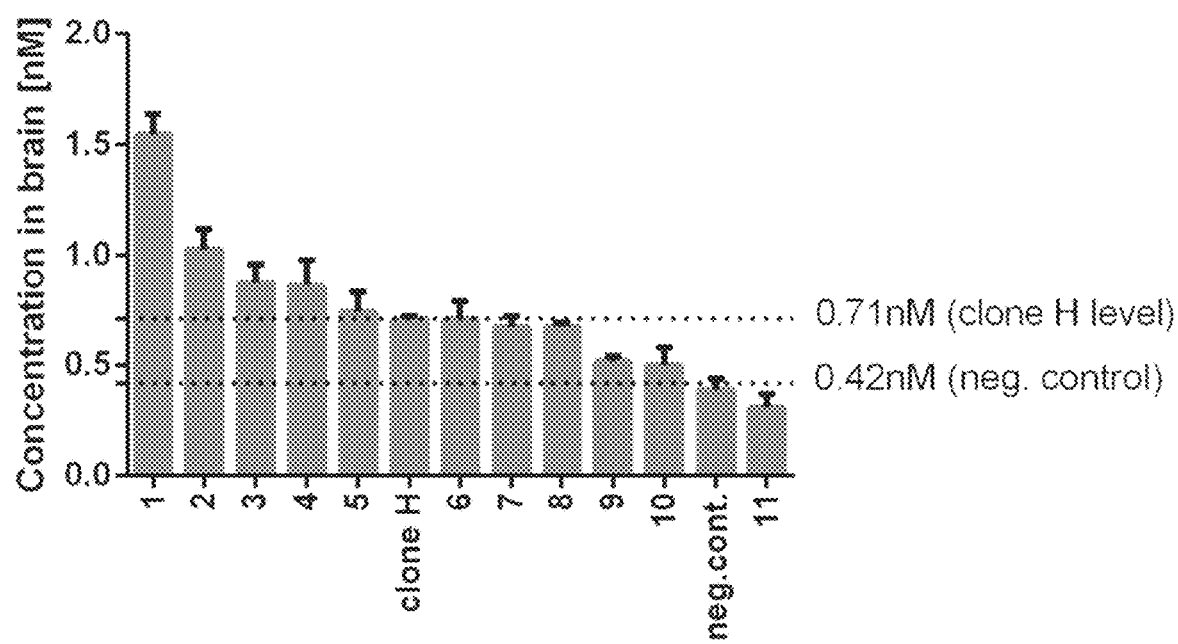
FIG. 12. Brain uptake of Clone H Variants as Fc Fusion Proteins. Clone H variants were generated as bivalent human Fc fusion proteins and tested for brain penetration in mice. The dotted line at 0.71 nM indicates the brain concentration of Clone H and the dotted line at 0.42 nM indicates the cut-off used for positive effects in this experiment. VNAR-Fcs were administered intravenously to mice at 25 nmol/kg and brains were excised 18 hours later following cardiac perfusion as detailed in the Examples. The VNAR-Fc concentration in brain homogenates was measured by human Fc capture ELISA and the values represent the mean±SD, N=3/group.

The Clone C and Clone H variants are TfR-specific binding moieties, which like Clone C and Clone H, are capable of specific binding to human TfR-1 and mouse TfR-1 and crossing the BBB. For example, when formatted as Fc fusion proteins and injected into mice 1.875 mg/kg as described in the Examples below, the TfR-specific binding moieties of the invention accumulate in murine brain homogenates at concentrations ranging from at least about 0.4 nM to 15 nM, from about 0.8 nM to about 15 nM, from about 1 nM to about 12 nM, or from about 2.5 nM to about 10 nM (FIGS. 5 and 12).

Figure 6:
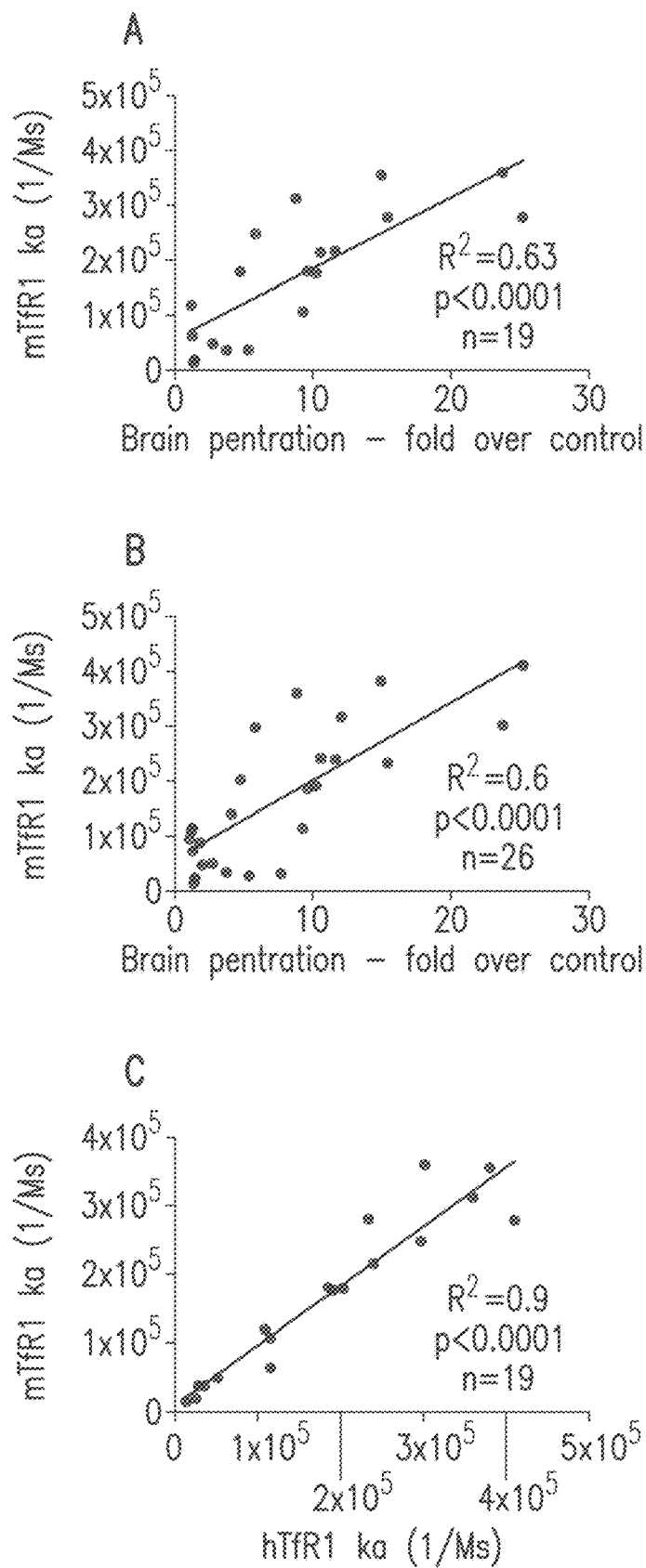
FIG. 6. Brain Penetration of Clone C Variants as a function of the Association Rate (ka). Pearson correlation analysis of association rates (ka) of Clone C variants for binding to (A) mouse and (B) human TfR-1 with brain penetration (expressed as fold increase over control). The ka of Clone C variants was measured using Biacore™ surface plasmon resonance (SPR) system with anti-His capture chip and immobilised His-tagged TfR-1. (C) Correlation of binding ka of the Clone C variants with mouse and human TfR-1.
Figure 7:
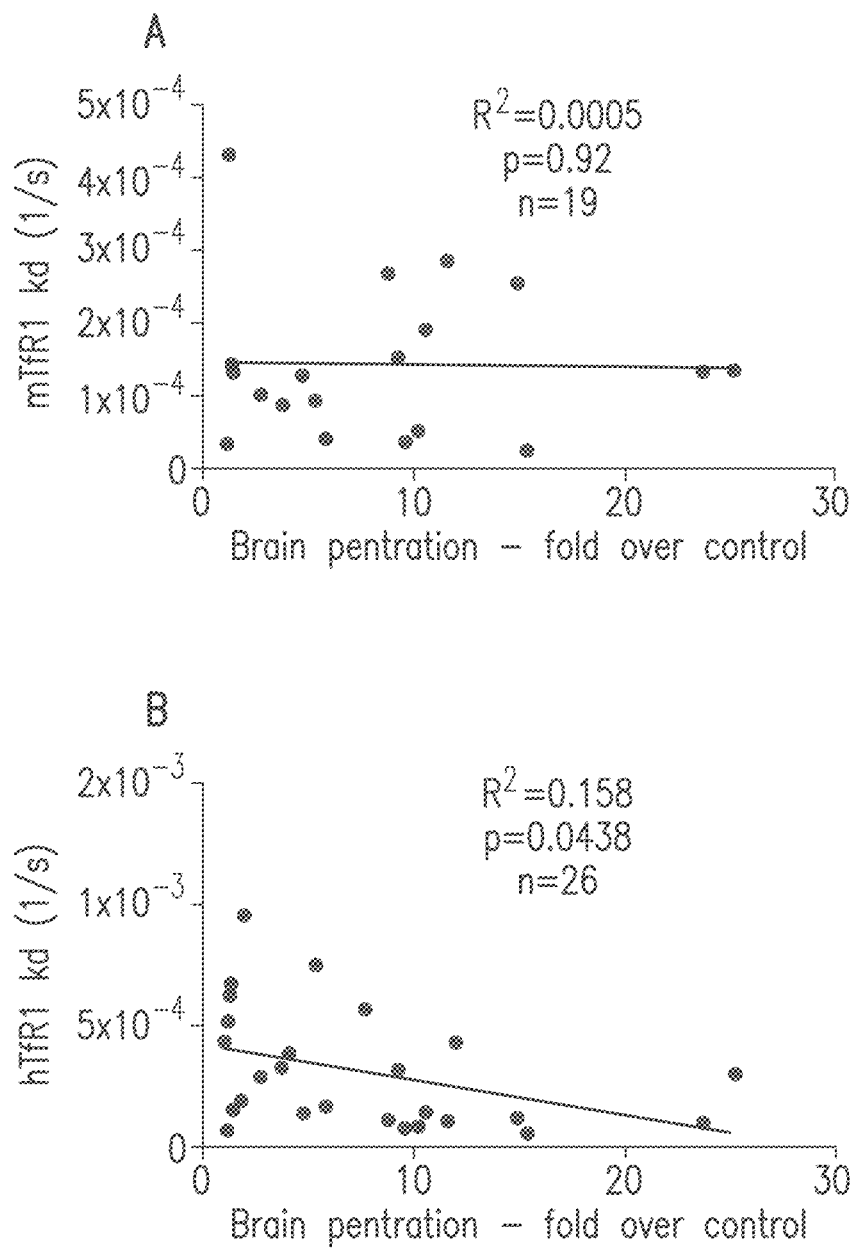
FIG. 7. Brain Penetration of Clone C Variants as a function of the Dissociation Rate (kd). Pearson correlation analysis of dissociation rates (kd) of Clone C variants for binding to (A) mouse and (B) human TfR-1 with brain penetration (expressed as fold increase over control). The kd of Clone C variants was measured using Biacore with anti-His capture chip and immobilised His-tagged TfR-1.

In analyzing the Clone C variants, a correlation was observed between the association rate (ka), or on rate of the TfR-specific binding moiety with hTfR or mTfR as shown in FIGS. 6A and B. In particular, binders with higher association rates exhibit increased brain concentrations. Variants with good brain penetration ability have a ka for human or mouse TfR-1 ranging from about 1.0E+04 1/Ms to about 4.5E+05 1/Ms, or from about 1.2E+04 1/Ms to about 3.5E+05 1/Ms, with a threshold ka value of at least about 1.0E+04 1/Ms. In contrast, no correlation was found between dissociation rate (kd) and brain penetration (FIG. 7).

Figure 8:
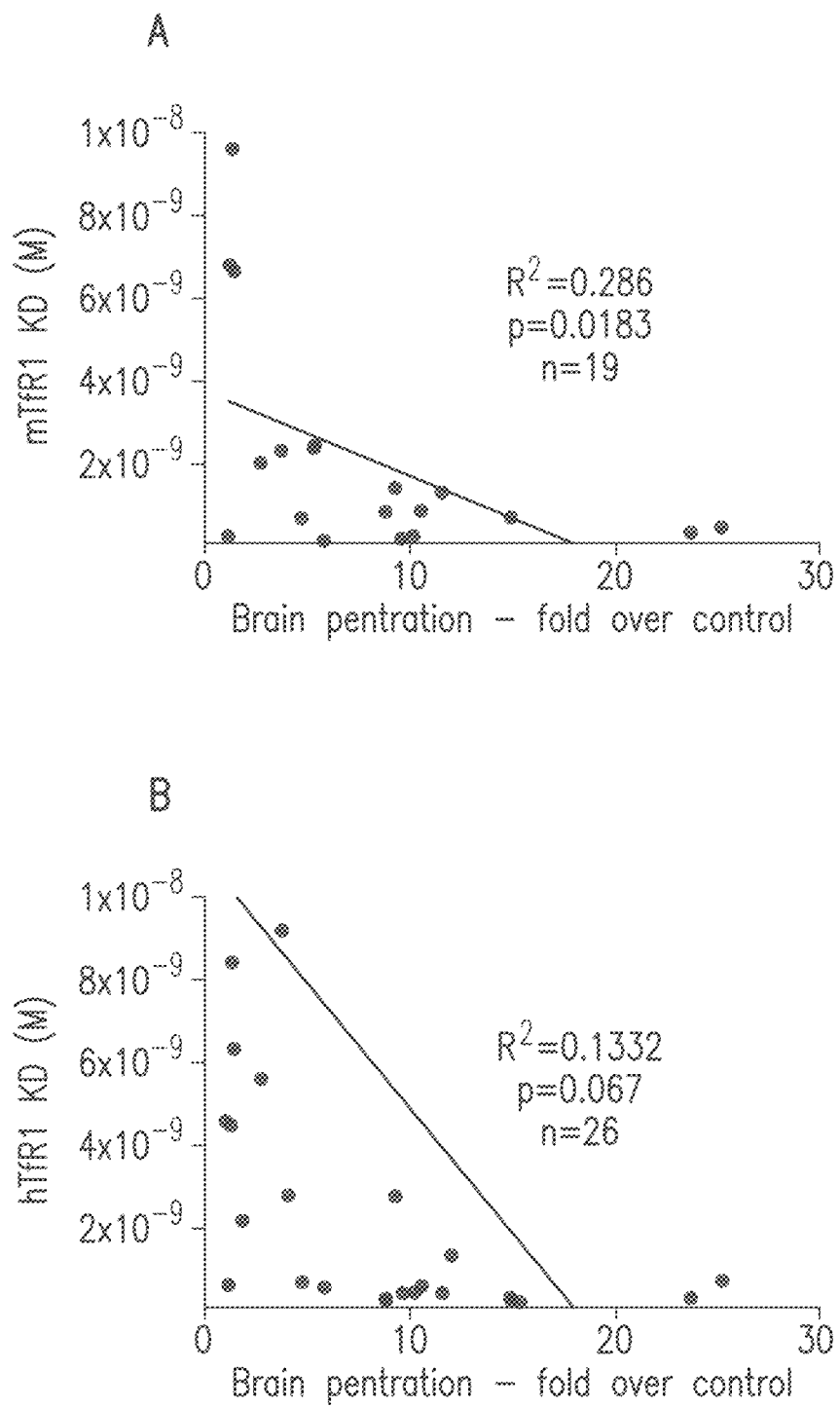
FIG. 8. Brain Penetration of Clone C Variants as a function of the Binding Affinity. Pearson correlation analysis of dissociation constants (KDs) of Clone C variants for binding to (A) mouse and (B) human TfR-1 with brain penetration (expressed as fold increase over control).

Further analysis of the Clone C variants demonstrated, in contrast to other studies, that variants with higher binding affinities (KD) were better at penetrating the BBB and release into brain tissue (FIG. 8). Thus, in some embodiments, the TfR-specific binding moieties of the invention exhibit KDs for human or mouse TfR-1 ranging from about 100 pM to about 50 nM, or from about 200 pM to about 3 nM. In other words, TfR binders having KDs no greater than 3 nM exhibit unexpectedly good ability to cross the BBB.

As used herein, a "VNAR scaffold" has the general structure, from N to C terminus, given by the formula FW1-CDR1-FW2-HV2-FW2'-HV4-FW3-CDR3-FW4, wherein the FWs are framework regions, CDRs are complementarity determining regions and HVs are hypervariable regions that form the variable domain of a shark IgNAR ("VNAR"). VNAR scaffolds of the invention where the FW1, FW2, FW2', FW3 and FW4 regions have naturally occurring VNAR sequences or altered VNAR sequences with amino acid substitutions, insertions or deletions (typically, but not limited to, no more than 1-10 amino acids a changes) provided that such changes maintain the overall primary and tertiary structure of the VNAR. Those of skill in the art can identify and ascertain the effect of such alterations. In addition, the FW1, FW2, FW2', FW3 and FW4 regions can have any of the sequences shown in Table 1 for these regions under the VNAR Domain Amino Acid Sequence column of WO2016/077840, provided functionality of the overall TfR-specifi binding moiety is maintained in accordance with the instant invention.

As used herein a "VNAR domain" means a naturally-occurring VNAR, an altered VNAR (such as those described herein), a variable domain of a camelid antibody (known as a VHH) or the variable domain of any single chain antibody, whether such domains are naturally occurring, selected or engineered.

The VNARs, the VNAR scaffolds and the VNAR domains of the invention can optionally have a His-Tag (or other convenient tag for purification purposes). In some cases, such tags are removable.

In yet another aspect of the invention, any of the TfR-specific binding moieties can form all or part of the variable domain of a single variable domain antibody, a bi- or tri-functional VNAR or IgNAR, a conventional antibody, or any fragment or fusion protein of said antibody as well as variable domains with antibody-like backbones.

Examples of single variable domain antibodies include, but are not limited to, a shark or other cartilaginous fish antibodies, camelid antibodies and nobodies. Examples conventional antibodies include, but are not limited to, immunoglobins having both heavy and light chains, such as IgM's, IgA's, IgG's, IgE's, single chain Fv's, Fab fragments, or any fragment or fusion protein of such antibodies or fragments.

Non-limiting examples of antibody-like backbones that may be used according to the invention include monospecific and bispecific such as multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H$1 domains, bivalent F(ab')2 fragments, Fd fragments consisting of the heavy chain and $C_H$1 domains, dimeric $C_H$2 domain fragments ($C_H$2D), Fc antigen binding domains (Fcabs), single chain Fv-$C_H$3 minibodies, bispecific minibodies, isolated complementary determining region 3 (CDR3) fragments, constrained FR3-CDR3-FR4 polypeptides, SMIP domains, and any genetically manipulated counterparts of the foregoing that retain TfR-1 binding function (see e.g., Weiner L, Cell 148: 1081-4 (2012); Ahmad Z et al., Clin Dev Immunol 2012: 980250 (2012) for reviews).

Therefore, in one aspect, the invention provides a TfR-selective compound comprising or consisting essentially of a VNAR-derived TfR-specific binding moiety which binds selectively to a TfR polypeptide, preferably to human TfR (see e.g., UniProt P02786 TFR1 Human) or to a, e.g., human, TfR epitope-containing polypeptide.

In certain embodiments, a TfR-specific binding moiety of the invention binds to a transferrin receptor (TfR) on the membrane of a mammalian cell and TfR-specific binding mediates transport of the TfR-specific binding moiety and at least one associated heterologous molecule across the cell membrane. Any TfR-positive cell or cell type (i.e., one with the transferrin receptor localized at the cell membrane) may thus be used to target delivery of heterologous molecules across its membrane by association (e.g., as a complex or conjugate) with a TfR-specific binding moiety of the invention. As described in more detail below, heterologous molecules may be selected from an enormously wide variety of agents, limited only by the target cell's requirement of having a cell surface TfR which can internalize upon binding of a TfR-specific binding moiety of the invention.

In certain embodiments of the invention, the cell membrane is part of the blood brain barrier (BBB) and TfR-mediated transport across the BBB of a heterologous molecule may be accomplished. In certain other embodiments of the invention, the cell membrane is part of the GI tract and TfR-mediated transport of a heterologous molecule may be accomplished, enabling oral drug delivery routes, especially advantageous for previously non-orally bioavailable drugs or molecules for therapeutics and/or diagnostics.

Associated heterologous molecules which may be used in conjunction with any one of the above embodiments may comprise, e.g., one or more biologically active molecules and/or imaging agents. Exemplary biologically active molecules which may be transported into a TfR-positive cell in association with a TfR-specific binding moiety of the invention include, e.g., toxins for targeted TfR-positive cell death (useful e.g., in certain hyperproliferative diseases or disorders such as cancers or aberrant proliferative conditions). Other exemplary biologically active molecules which may be transported in association with a TfR specific binding moiety include, e.g., polypeptides, such as an antibody or antibody fragment; a therapeutic peptide such as a hormone, cytokine, growth factor, enzyme, antigen or antigenic peptide, transcription factor, or any functional domain thereof. Other exemplary biologically active molecules which may be transported into a TfR-positive cell in association with a TfR specific binding moiety include, e.g., nucleic acid molecules, such as an oligonucleotide (e.g., single, double or more stranded RNA and/or DNA molecules, and analogs and derivatives thereof); small regulatory RNA such as shRNA, miRNA, siRNA and the like; and a plasmid or fragment thereof.

Exemplary polypeptides which may be therapeutically beneficial when administered as a heterologous molecule for TfR-mediated transport across the BBB or other TfR-containing cell membrane include but are not limited to: a brain derived neurotrophic factor (BDNF), a bone morphogenic protein (e.g., BMP-1 through BMP-7, BMP8a, BMP8b, BMP10 and BMP15), a ciliary neurotrophic factor (CNF), an epidermal growth factor (EGF), erythropoietin, a fibroblast growth factor (FGF), a glial derived neurotrophic factor (GDNF), a heptocyte growth factor, an interleukin (e.g., IL-1, IL-4, IL-6, IL-10, IL-12, IL-13, IL-15, IL-17), a nerve growth factor (NGF), a neurotrophin (e.g., NT-3 and NT-4/5), a neurturin, a neuregulin, a platelet derived growth factor (PDGF), a transforming growth factor (e.g., TGF-alpha and TGF-beta), apolipoprotein E (ApoE), a vasoactive intestinal peptide, artemin, persephin, netrin, neurotensin, GM-GSF, cardiotrophin-1, stem cell factor, midkine, pleiotrophin, a saposin, a semaporin, leukemia inhibitory factor, and the like.

Exemplary therapeutic antibodies or fragments that may be transported across the BBB or other TfR-containing cell membrane as a heterologous biologically active molecule of the invention include but are not limited to: antibodies for neurodegeneration including anti-Abeta, anti-Tau, anti-alpha-synuclein anti-Trem2, anti-C9orf7 dipeptides, anti-TDP-43, anti-prion protein C, anti-huntingtin, anti-nogo A, anti-TRAIL (tumor necrosis factor-related apoptosis-inducing ligand); antibodies for neuro-oncology including anti-HER2, anti-EGF, anti-PDGF, anti-PD1/PDL1, anti-CTLA-4, anti-IDO, anti-LAG-3, anti-CD20, anti-CD19, anti-CD40, anti-OX40, anti-TIM3, anti-toll-like receptors; antibodies for neuroinflammation including anti-TNF, anti-CD138, anti-IL-21, anti-IL-22; antibodies to viral diseases of the brain including anti-West Nile virus, anti-Zika, anti-HIV, anti-CMVanti-HSV and the like.

Exemplary enzymes that may be transported across the BBB or other TfR-containing cell membrane as a heterologous biologically active molecule of the invention include but are not limited to: alpha-L-iduronidase, iduronate-2-sulfatase, N-acetyl-galactosamine-6-sulfatase, arylsulfatase B, acid alpha-glucosidase, tripeptidyl-peptidase 1, acid sphingomyelinase glucocerebrosidase and heparan sulfamidase.

Also included as exemplary biologically active molecules are small molecules comprising chemical moieties (such as a therapeutic small molecule drugs); carbohydrates; polysaccharides; lipids; glycolipids and the like. Exemplary embodiments of such small molecule therapeutic agents include certain cancer drugs, such as daunorubicin, doxorubicin, and other cytotoxic chemical agents including microtubule inhibitors, topoisomerase inhibitors, platins, alkylating agents, and anti-metabolites all of which may beneficially be administered across the BBB at lower overall systemic doses than by IV administration. Other small molecule therapeutic agents may include corticosteroids, NSAIDs, COX-2 inhibitors, small molecule immunomodulators, non-steroidal immunosuppressants, 5-amino salicylic acid, DMARDs, hydroxychloroquine sulfate, and penicillamine. 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, among others. Small molecule therapeutic agents which may be used according to the invention also include bevacizumab, cisplatin, irinotecan, methotrexate, temozolomide, taxol and zoledronate. Certain anti-inflammatory agents may be useful biologically active molecules. Fluoxetine, for example, reportedly inhibits MMP-2, MMP-9 and MMP-12 expression associated with blood-brain barrier disruption and inflammatory reactions after spinal cord injury, which may be used according to the invention to protect blood-brain barrier and to inhibit deleterious inflammatory responses in spinal cord injury and central nervous system disease. Other non-limiting examples of therapeutic antibodies which may be beneficially transported across the BBB include anti-CD133, anti-CD137, anti-CD27, anti-VEGF, anti-EGRFvIII, anti-IL-15 and anti-IL13R.

Exemplary embodiments of an imaging agent as an associated heterologous molecule include agents that comprise at least one of a metal such as a paramagnetic metal, a radionuclide such as a radioisotope, a fluorochrome or fluorophor, an energy emitting particle, a detectable dye, and an enzyme substrate.

Further examples of biologically active molecules include small molecules, including therapeutic agents, in particular those with low blood-brain barrier permeability. Some examples of these therapeutic agents include cancer drugs, such as daunorubicin, doxorubicin, and toxic chemicals which, because of the lower dosage that can be administered by this method, can now be more safely administered. For example, a therapeutic agent can include bevacizumab, irinotecan, zoledronate, temozolomide, taxol, methotrexate, and cisplatin.

In another embodiment, the therapeutic agent can include a broad-spectrum antibiotic (e.g., cefotaxime, ceftriaxone, ampicillin and vancomycin); an antiviral agent (e.g., acyclovir); acetazolamide; carbamazepine; clonazepam; clorazepate dipotassium; diazepam; divalproex sodium; ethosuximide; felbamate; fosphenytoin sodium; gabapentin; lamotrigine; levetiracetam; lorazepam; oxcarbazepine; phenobarbital; phenytoin; phenytoin sodium; pregabalin; primidone; tiagabine hydrochloride; topiramate; trimethadione; valproic acid; zonisamide; copaxone; tysabri; novantrone; donezepil HCL; rivastigmine; galantamine; memantine; levodopa; carbidopa; parlodel, permax, requip, mirapex; Symmetrel; artane; cogentin; eldepryl; and deprenyl. Antiviral compounds are also beneficial therapeutic agents that can be delivered using a TfR-specific binding moiety of the invention, especially for cases in which the virus uses UR transport as its route of entry into infected cells.

Numerous other examples of biologically active molecules may be used in association with a TfR-specific binding moiety of the invention, appropriate selection of which will be apparent to the skilled artisan depending on the condition, disease or disorder to be treated.

Yet other examples of a biologically active molecule which may be used according to the present invention is an antigenic peptide. Antigenic peptides may provide immunological protection when imported by cells involved in an immune response. Other examples include immunosuppressive peptides (e.g., peptides that block autoreactive T cells, such peptides being known in the art).

An imaging agent, as used herein, may be any chemical substance which may be used to provide a signal or contrast in imaging. A signal enhancing domain may be an organic molecule, metal ion, salt or chelate, a particle (e.g., iron particle), or a labeled peptide, protein, glycoprotein, polymer or liposome. For example, an imaging agent may include one or more of a radionuclide, a paramagnetic metal, a fluorochrome, a dye, and an enzyme substrate.

For x-ray imaging, the imaging agent may comprise iodinated organic molecules or chelates of heavy metal ions of atomic numbers 57 to 83. In certain embodiments, the imaging agent is $I^{125}$ labeled IgG (see, e.g., M. Sovak, ed., "Radiocontrast Agents," Springer-Verlag, pp. 23-125 (1984).

For ultrasound imaging, an imaging agent may comprise gas-filled bubbles or particles or metal chelates where the metal ions have atomic numbers 21-29, 42, 44 or 57-83. See e.g., Tyler et al., Ultrasonic Imaging, 3, pp. 323-29 (1981) and D. P. Swanson, "Enhancement Agents for Ultrasound: Fundamentals," Pharmaceuticals in Medical Imaging, pp. 682-87. (1990) for other suitable compounds.

For nuclear radiopharmaceutical imaging or radiotherapy, an imaging agent may comprise a radioactive molecule. In certain embodiments, chelates of Tc, Re, Co, Cu, Au, Ag, Pb, Bi, In and Ga may be used. In certain embodiments, chelates of Tc-99m may be used. See e.g., Rayudu GVS, Radiotracers for Medical Applications, I, pp. 201 and D. P. Swanson et al., ed., Pharmaceuticals in Medical Imaging, pp. 279-644 (1990) for other suitable compounds.

For ultraviolet/visible/infrared light imaging, an imaging agent may comprise any organic or inorganic dye or any metal chelate.

For MRI, an imaging agent may comprise a metal-ligand complex of a paramagnetic form of a metal ion with atomic numbers 21-29, 42, 44, or 57-83. In certain embodiments, the paramagnetic metal is selected from: Cr(III), Cu(II), Dy(III), Er(III) and Eu(III), Fe(III), Gd(III), Ho(III), Mn(II and III), Tb(III). A variety of chelating ligands useful as MRI agents are well known in the art.

In sum, the invention includes TfR-specific conjugate comprising a TfR-specific binding moiety of the invention operably linked to a heterologous molecule which differs in biological activity from said moiety. Such operable linkages can be a covalent or non-covalent linkage and the heterologous molecule can be a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with targeting or other regulatory properties (e.g., silencers) or which encodes a regulatory molecule for a cell.

For the avoidance of doubt, a TfR-selective binding compound includes TfR-specific binding moieties alone, as part of antibodies (or fragments thereof as described herein), as part of conjugates or encoded in viral or other vectors.

Monitoring TfR Binding and Cell Internalization

TfR-binding activity (also referred to herein as "TfR bioactivity") may be determined by one or more assays described in the Examples herein, or by any other suitable method in the art, including well-known immunoassays, such as for example the ELISAs or variations thereon described in the Examples. Any other binding assay which directly or indirectly measures the binding of the TfR-specific binding moiety to a cell surface TfR, or alternatively, which measures the ability of a TfR-specific binding moiety, conjugate or compound comprising such a moiety of the invention to compete for binding to TfR in the presence of a different TfR binding compound (such as an anti-TfR antibody) such as by a competitive inhibition assay, may be used. Preferably, a selected assay measures the effect of a TfR-specific binding moiety or compound comprising such a moiety on its ability to transport a heterologous molecule or biomolecule across the membrane of a TfR-positive cell. In certain embodiments, the TfR-positive cell is one which transports a heterologous molecule across the blood brain barrier (BBB). In certain embodiments, the TfR-positive cell is one which transports a heterologous molecule across cells of the gastrointestinal tract. In certain embodiments, binding of the TfR binding moiety to TfR is measured by monitoring internalization of the TfR binding moiety into TfR-positive cells or cell type. In vivo assays of TfR bioactivity include, but are not limited to those described in the Examples herein.

Other test systems to assess TfR binding and functional activity include, for example: Surface plasmon resonance to determine affinity and off-rates; using radiolabeled or fluorescent tagged molecule or GFP fusion proteins in in vitro or in vivo animal studies including binding and internalization in tumor cell lines, immortalized endothelial cell lines or primary cells expressing TfR; in vitro transcytosis in capillary endothelial cells and cells lines; and permeability assay using Caco-2 and MDCK epithelial cell lines; in situ perfusion models and immunohistochemical or immunofluorescent staining of tissue sections; optical or PET animal imaging; standard PK and tissue distribution assays; and measuring one or more biological effects of a heterologous molecule (drug cargo or payload) in normal animals or disease animal models.

Therapeutic versions of compounds with TfR-specific binding moieties of the invention include other molecular configurations, e.g., a VNAR monomer (i.e., a TfR-binding moiety) fused to stabilizing heterologous peptide regions, e.g., the Fc domain of an IgG or other immunoglobulin molecule, which may be expressed and then further purified as multimers, such as covalent dimmers, allowing the activity of certain such therapeutic molecules to have even greater potency, preferably by at least 2-10 fold higher potencies and different binding affinities to TfR-1. Any of the antibody or antibody-like structures contemplated by the invention can be used as therapeutics Pharmaceutically acceptable salts or solvates of any of the TfR-specific binding compounds of the invention are likewise within the scope of the present invention. As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type N(R1)(R2)(R3)(R4)+, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), N.Y., USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

In each of the sequences described above, and in each sequence described herein, a C-terminal "—OH" moiety may be substituted for a C-terminal "—NH$_2$" moiety, and vice-versa.

Each of the specific compounds of the invention (e.g., TfR binding moieties, TfR antagonist peptides and compounds), and pharmaceutically acceptable salts and solvates thereof, constitutes an individual embodiment of the invention.

Conjugates

TfR specific VNAR comprising compounds of the invention may optionally be conjugated (e.g., using linkers such as chemical linkers and/or linker peptides which are not usually associated with the domains being associated) to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like. In certain embodiments, the pharmaceutically active moieties of the invention comprise at least one scFv molecule that is operably linked via a linker peptide to the C-terminus and/or N-terminus of an Fc region.

In certain embodiments, a compound of the invention comprising a TfR-specific binding moiety is multispecific, i.e., has at least one binding site that binds to a first molecule or epitope of a molecule (e.g., human TfR-1) and one or more other binding sites that bind to at least one heterologous molecule or to an epitope of either TfR-1 or another molecule. Multispecific binding molecules of the invention may comprise at least two binding sites, three binding sites, four binding sites or more. In certain embodiments, at least two binding site of a multispecific binding molecule of the invention are capable of transporting a linked molecule across the BBB.

The invention thus further provides methods of making derivatives of TfR specific VNARs of the invention using biochemical engineering techniques well known to those of skill in the art. Such derivatives include, inter alia, multivalent or multispecific molecules comprising a TfR-specific binding moiety, including immunoconjugates. A large body of art is available relating to how to make and use antibody drug conjugates. Such knowledge and skill in the art may be adapted for use with the TfR specific binding moieties and TfR selective binding compounds of the invention. See, e.g., WO2007/140371; WO2006/068867 specific to TfR; methods relating to making and/or using different ligand conjugates may be applied. In certain embodiments, the TfR selective binding moieties and TfR selective binding compounds of the present invention include covalently modified and conjugated polypeptides forms of the polypeptides (e.g., immunoadhesins, radiolabeled or fluorescently labeled compounds, and the like). Methods for peptide conjugation and for labeling polypeptides and conjugating molecules are well known in the art.

Nucleic Acid Sequences That Encode a TfR Selective Binding Moiety or TfR Antagonist Compound In one aspect, the invention provides an isolated nucleic acid which encodes a TfR specific binding moiety or compound of the invention, or a fragment or derivative thereof. The invention also provides an isolated nucleic acid molecule comprising a sequence that hybridizes under stringent conditions to a nucleic acid sequence which encodes a TfR specific binding moiety or compound of the invention, or a fragment or derivative thereof, or the antisense or complement of any such sequence.

In another aspect, the invention provides an isolated nucleic acid molecule encoding a fusion protein comprising at least two segments, wherein one of the segments comprises a Clone C variant according to the invention. In certain embodiments, a second segment comprises a heterologous signal polypeptide, a heterologous binding moiety, an immunoglobulin fragment such as a Fc domain, or a detectable marker.

One aspect of the invention provides isolated nucleic acid molecules that encode TfR specific binding moiety proteins or biologically active portions thereof. Also included are nucleic acid fragments sufficient for use as hybridization probes to identify TfR binding moiety encoding nucleic acids and fragments for use as polymerase chain reaction (PCR) primers for the amplification or mutation of TfR specific binding moiety encoding nucleic acid molecules.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the invention may be single-, double-, or triple-stranded. A nucleic acid molecule of the present invention may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the invention may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a TfR selective binding moiety or compound of the invention may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the invention include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. A percent identity for any candidate nucleic acid or polypeptide relative to a reference nucleic acid or polypeptide may be determined by aligning a reference sequence to one or more test sequences using, for example, the computer program ClustalW (version 1.83, default parameters), which enable nucleic acid or polypeptide sequence alignments across their entire lengths (global alignment) or across a specified length. The number of identical matches in such a ClustalW alignment is divided by the length of the reference sequence and multiplied by 100.

Also included are nucleic acid molecules capable of hybridizing to the complement of a sequence encoding the proteins of the invention under stringent or moderately stringent conditions. See e.g. Ausubel, et al., CURRENT PROTOCOLS IN MOLECULAR BIOLOGY, John Wiley & Sons, New York, N.Y., 1993, and below. An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing TfR Specific VNAR Binding Moieties and Compounds Comprising Them The compounds of the invention may be manufactured by standard synthetic methods, by use of recombinant expression systems, or by any other suitable method. Thus, the compounds may be synthesized in a number of ways, including, e.g., methods comprising: (1) synthesizing a polypeptide or polypeptide component of a TfR specific binding compound using standard solid-phase or liquid-phase methodology, either stepwise or by fragment assembly, and isolating and purifying the final peptide compound product; (2) expressing a nucleic acid construct that encodes a polypeptide or polypeptide component of a TfR specific binding compound in a host cell and recovering the expression product from the host cell or host cell culture; or (3) cell-free in vitro expression of a nucleic acid construct encoding a polypeptide or polypeptide component of a TfR specific binding compound, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a TfR-specific binding compound of the invention by means of solid-phase or liquid-phase peptide synthesis. Compounds of the invention may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a TfR specific binding compound of the invention according to above recited methods; a nucleic acid molecule encoding part or all of a polypeptide of the invention, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

TfR specific binding compounds of the invention may be prepared using recombinant techniques well known in the art. In general, methods for producing polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available.

Expression vectors capable of directing transient or stable expression of genes to which they are operably linked are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce TfR specific binding compounds of the invention. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, Arabidopsis, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a TfR-specific binding moiety, conjugate or compound of the invention can be accomplished using standard techniques known in the art. Mammalian cells are preferred host cells for expression of peptides. Particularly useful mammalian cells include, inter alia, HEK 293, NSO, DG-44, and CHO cells, but any other suitable host cell may be used according to the invention. Preferably, the TfR-specific moieties, conjugates or compounds are secreted into the medium in which the host cells are cultured, from which the TfR-specific binding moieties, conjugates or compounds may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a TfR-specific binding moiety, conjugate or compound of the invention.

Methods of Detection

In certain embodiments, the TfR specific binding compounds of the invention may be used to detect and quantify levels of TfR, or cells that express TfR. This can be achieved, for example, by contacting a test sample (such as an in vitro sample) and a control sample with a TfR specific binding moiety of the invention, or a compound comprising it, under conditions which permit formation of a complex between the compound and TfR, or between TfR and an anti-TfR antibody, or both. Any bound TfR complexes are detected and/or quantified in TfR specific VNAR containing samples and control samples.

Accordingly, the invention further provides methods for detecting the presence of TfR or TfR antibodies in a sample, or measuring the amount of either of the foregoing, comprising contacting the sample, and preferably a control sample, with a TfR-binding compound of the invention under conditions that permit complex formation between the TfR binding moiety of the compound and TfR, e.g., human TfR. Formation or inhibition of formation of a TfR-binding compound/TfR complex is then detected and/or quantified. A variety of tests can be designed based on features of binding or competition for binding. For example, the presence of TfR in a test sample may be detected directly, or may be detected and quantified based on the ability to compete for binding of TfR by a TfR-binding moiety, conjugate or compound. In general, the difference in complex formation between a test sample and a control sample is indicative of a binding interaction.

Methods of Treatment Using TfR Binding Moieties and Compositions

The present invention provides a TfR binding moiety or TfR specific binding compound for use, alone or in combination with one or more additional therapeutic agents in a pharmaceutical composition, for treatment or prophylaxis of conditions, diseases and disorders responsive to modulation (such as inhibiting or blocking) of the interaction between TfR and its in vivo ligands.

In certain embodiments, a TfR specific binding moiety or a conjugate or drug delivery vehicle comprising such a binding moiety is administered in combination with at least one additional agent that mediates blood-brain barrier transport, such as an agent comprising a receptor binding domain of an apolipoprotein such as a receptor binding domain of ApoA, ApoB, ApoC, ApoD, ApoE, ApoE2, ApoE3 or ApoE4, and any combination thereof. Any one of a number of other molecules which mediate transport of heterologous molecules across the blood brain barrier may be used in combination with the TfR specific binding moiety comprising agents of the invention, including, e.g., IgG, YY (PYY), neuropeptide Y (NPY), corticotropin releasing factor (CRF), and urocortin. Certain viral glycoproteins (e.g., rabies virus glycoprotein (RVG) peptide) and antibodies and antibody fragments may also be used in this regard.

Combination therapies may include co-administration of agents or alternate administrations which result in a combination therapy within the patient based on duration of the therapeutic agent(s) or their biological effects in the patient.

In certain embodiments, a therapeutic agent transported across the BBB in association with a TfR-specific binding moiety of the invention is effective in treating a brain or CNS disease, condition, injury or disorder, such as, for example, neurodegenerative diseases, neuronal injury, stroke, genetic disorders, psychiatric disorders, developmental disorders, inflammation, infection or damage, and brain cancers, spinal cord injury (SCI) and traumatic brain injury (TBI). In certain embodiments, a brain disorder is selected from epilepsy, meningitis, encephalitis including HIV Encephalitis, progressive multifocal leukoencephalopathy, neuromyelitis optica, multiple sclerosis, late-stage neurological trypanosomiasis, amyotrophic lateral sclerosis (ALS), progressive bulbar palsy (PBP), primary lateral sclerosis (PLS), progressive muscular atrophy (PMA), Alzheimer's disease, Parkinson's disease, Huntington's disease, De Vivo disease, and any type of tumor, cancer or hyperproliferative disease in the brain or CNS.

In certain embodiments, a therapeutic agent transported across a hTfR1-containing membrane in association with a TfR-specific binding moiety of the invention is effective in treating a condition, disease or disorder associated with the GI tract or one which will otherwise benefit from drug delivery across an epithelial membrane of the gut mediated by hTfR1 transport.

The invention in certain embodiments provides methods of treatment or prevention of a TfR associated disorder, the method comprising the step of administering to a subject (e.g., a patient) in need thereof a therapeutically effective amount of the TfR specific binding compound or pharmaceutical composition comprising a TfR binding compound of the invention, as described herein. As used herein, an "effective amount," a "therapeutically effective amount" or an "effective dose" is an amount of a composition (e.g., a therapeutic composition or agent) that produces at least one desired therapeutic effect in a subject, such as preventing or treating a target condition or beneficially alleviating a symptom associated with the condition.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, Pa., 2005.

Additionally, for some embodiments specificity for TfR1 is an important feature for a BBB carrier because off target binding to TfR2 could have undesirable safety and/or PK consequences. The expression of TFR2 is restricted to hepatocytes and erythroid precursors (Silvestri et al., Front Pharmacol. 2014 May 7; 5:93). Interference with transferrin binding to TfR2, which is a component of the erythropoietin receptor complex, could disrupt normal erythropoiesis (Forejtnikovà et al., Blood. 2010 Dec. 9; 116(24):5357-67). Additionally, high levels of TfR2 expressed in the liver may be responsible for the rapid clearance and short half life of some cross-reacting TfR antibodies (Boado et al., Biotechnol Bioeng. 2009 Mar. 1; 102(4):1251-8). VNAR antibodies to TfR1 are highly specific and exhibit the same long half-life as IgG.

Pharmaceutical Compositions

The present invention further provides pharmaceutical compositions comprising a TfR-specific binding moiety of the invention or compound, or a pharmaceutically acceptable salt or solvate thereof, according to the invention, together with a pharmaceutically acceptable carrier, excipient or vehicle.

Accordingly, the present invention further provides a pharmaceutical composition comprising a TfR-specific binding moiety of the invention or compound comprising a TfR-specific binding moiety, as well as variant and derivative compounds comprising a TfR-specific binding moiety of the invention. Certain embodiments of the pharmaceutical compositions of the invention are described in further detail below.

The present invention also provides pharmaceutical compositions comprising a TfR-specific binding moiety or a TfR-specific binding compound for use in treating, ameliorating or preventing one or more diseases, conditions, disorders or symptoms relating to B cells and immunoglobulin production, as described in further detail below. Each such disease, condition, disorder or symptom is envisioned to be a separate embodiment with respect to uses of a pharmaceutical composition according to the invention.

Formulations, Administration and Dosing

TfR specific binding compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethypmethyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one or a combination of different TfR specific binding compounds of the invention, or a VNAR sequence containing, TfR specific binding region thereof, or an ester, salt or amide of any of the foregoing, and at least one pharmaceutically acceptable carrier. Such compositions may include one or more different BAFF specific binding moieties or compounds in combination to produce an immunoconjugate or multi-specific molecule comprising at least one TfR specific binding moiety. For example, a pharmaceutical composition of the invention may comprise a combination of TfR specific binding moieties which bind to different epitopes of TfR or which otherwise have complementary biological activities.

Pharmaceutical compositions of the invention may be administered alone or in combination with one or more other therapeutic or diagnostic agents. A combination therapy may include a TfR specific binding compound of the present invention combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the TfR specific binding moiety comprising compound or component may be coated in a material or materials intended to protect the compound from the action of acids and other natural inactivating conditions to which the active TfR binding moiety may encounter when administered to a subject by a particular route of administration.

As above, a compound of the invention may encompass one or more pharmaceutically acceptable salts. As used herein a "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N,N'-dibenzylethylene diamine, N-methylglucamine, chloroprocaine, choline, diethanolamine, ethylenediamine, procaine and the like.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

TfR selective binding moieties and compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active TfR specific binding compound. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a TfR specific binding moiety (or a TfR binding compound comprising such a moiety) in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a TfR selective binding moiety or composition of the invention is administered by, e.g., intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a TfR selective binding moiety or compound, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. TfR specific binding compounds will typically be administered on multiple occasions. Intervals between single dosages can be, for example, 2-5 days, weekly, monthly, every two or three months, every six months, or yearly. Intervals between administrations can also be irregular, based on regulating blood levels of TfR specific binding compound to the target TfR ligand in the subject or patient. In some methods, dosage is adjusted to achieve a plasma antagonist concentration of about 1-1000 µg/ml and in some methods about 25-300 µg/ml. Dosage regimens for a TfR specific binding compound of the invention include intravenous administration of 1 mg/kg body weight or 3 mg/kg body weight with the compound administered every two to four weeks for six dosages, then every three months at 3 mg/kg body weight or 1 mg/kg body weight.

In certain embodiments, two or more TfR specific binding compounds with different binding properties may be administered simultaneously or sequentially, in which case the dosage of each administered compound may be adjusted to fall within the ranges described herein.

In certain embodiments, a TfR specific binding compound of the invention may be administered as a sustained release formulation, in which case less frequent administration is required. Dosage and frequency vary depending on the half-life of the TfR specific binding compound in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the TfR specific binding compound alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular TfR specific binding compound or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Administration of a "therapeutically effective dosage" of a TfR-binding compound of the invention may result in a decrease in severity of disease symptoms, an increase in frequency and duration of disease symptom-free periods, or a prevention of impairment or disability due to the disease affliction.

A TfR specific binding compound or composition of the present invention may be administered via one or more routes of administration, using one or more of a variety of methods known in the art. As will be appreciated by the skilled worker, the route and/or mode of administration will vary depending upon the desired results. Routes of administration for TfR specific binding compounds or compositions of the invention include, e.g., intravenous, intramuscular, intradermal, intraperitoneal, subcutaneous, spinal or other parenteral routes of administration, for example by injection or infusion. The phrase "parenteral administration" as used herein refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

In other embodiments, a TfR specific binding compound or composition of the invention may be administered by a non-parenteral route, such as a topical, epidermal or mucosal route of administration, for example, intranasally, orally, vaginally, rectally, sublingually or topically.

As described elsewhere herein, an active TfR specific binding compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compounds or compositions of the invention may be administered with one or more of a variety of medical devices known in the art. For example, in one embodiment, a therapeutic TfR specific binding composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the TfR specific binding compound or composition of the invention may be formulated to ensure a desired distribution in vivo. For example, the blood-brain barrier (BBB) excludes many highly hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 and the like.

Kits for Detecting or Quantifying TfR in a Sample

Also within the scope of the invention are kits comprising at least one TfR specific binding moiety or TfR specific binding compound or composition of the invention, and optionally, instructions for use. Kits may be useful for quantifying TfR or TfR specific antibodies in a sample, or may be useful for detection of TfR, such as in diagnostics methods. The kit may further or alternatively comprise at least one nucleic acid encoding a TfR specific binding moiety of the invention. A kit of the invention may optionally comprise at least one additional reagent (e.g., standards, markers and the like). Kits typically include a label indicating the intended use of the contents of the kit. The kit may further comprise reagents and other tools for measuring TfR in a sample or in a subject, or for diagnosing whether a patient belongs to a group that responds to a TfR-specific binding compound which makes use of a compound, composition or related method of the invention as described herein.

Delivery Devices and Further Kits

In certain embodiments, the invention relates to a device comprising one or more TfR specific binding compounds of the invention, or pharmaceutically acceptable salts or solvates thereof, for delivery to a subject. Thus, one or more compounds of the invention or pharmaceutically acceptable salts or solvates thereof can be administered to a patient in accordance with the present invention via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising one or more peptides, or pharmaceutically acceptable salts or solvates thereof, of the invention. In other embodiments, the kit comprises one or more pharmaceutical compositions comprising one or more peptides or pharmaceutically acceptable salts or solvates thereof. In certain embodiments, the kit further comprises packaging and/or instructions for use.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

EXAMPLES

The examples presented herein represent certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1

Restricted, Random Mutagenesis of Clone C

Clone C, a human and mouse TfR-binding VNAR was obtained by in vivo selection of brain penetrating phages as described in Examples 1 and 2 of Intl. Appln. No. PCT/US2017/045592, filed Aug. 4, 2017 (now WO2018/031424). The VNAR domain amino acid sequence for Clone C is:

(SEQ ID NO. 1)

ARVDQTPQTITKETGESLTINCVLR*DSNCALS*STYWYRKKSGSTNEE

NISKGGRYVETVNSGSKSFSLRINDLTVEDSGTYRCNVVQYP

SYNNYFWCDVYGDGTAVTVN.

The CDR1 domain is bolded and italicized;
the CDR3 domain is underlined and bolded.

To improve BBB shuttling function of Clone C, its CDR3 region was subjected to a restricted randomisation process. Five new phage libraries were prepared based on the CDR3 with three subsequent residues randomised in each library and with the offset of two residues (FIG. 1).

The five restricted random mutagenized VNARs were inserted into modified pSEX81 (Progen) plasmid and used for M13-based phage display (Hasler, Flajnik et al. 2016). Recombinant human TfR-1 (Sino Biological, 11020-H07H) protein was biotinylated using Sulfo-NHS-Biotin EZ-Link™ kit (spacer product Thermo, 21326) and subsequently used at 100 nM concentration for each round of soluble phase in vitro selection (Griffiths, Williams et al. 1994). Magnetic streptavidin coupled Dynabeads® (magnetic spherical polystyrene beads; Thermo) were used for pulldown of the protein that, following washes, was eluted with 100 nM triethylamine, then pH adjusted and subsequently used for infection of E. coli ER2738 bacterial strain. The output titer was calculated by counting antibiotic resistant colonies and the culture was super-infected with M13K07 helper phage in order to produce phage for a round of selection.

Figure 2:
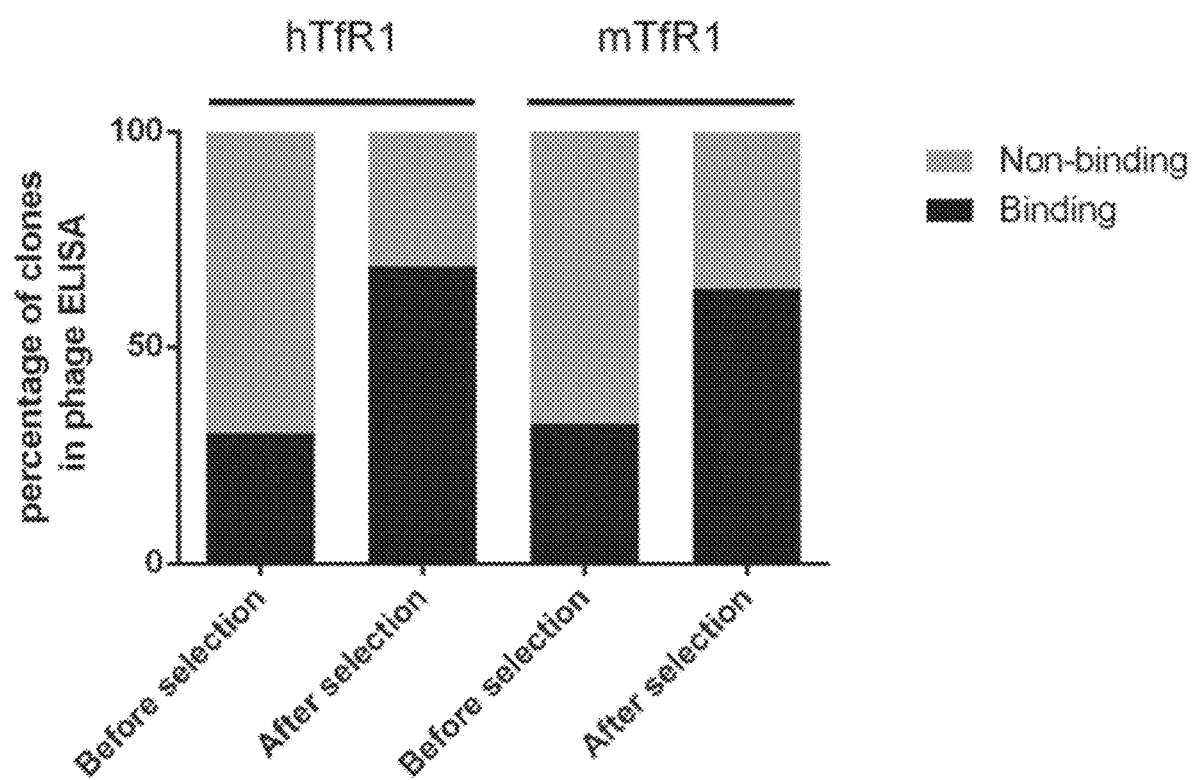
FIG. 2. Enrichment of TfR-binding Clone C Variants After Mutagenesis. Percentage of binding (OD at 450 nm>0.2) and non-binding (OD at 450 nm<0.2) clones to human and mouse TfR-1 before and after one round of panning of the pooled library of Clone C variants determined by phage ELISA.
Figure 3:
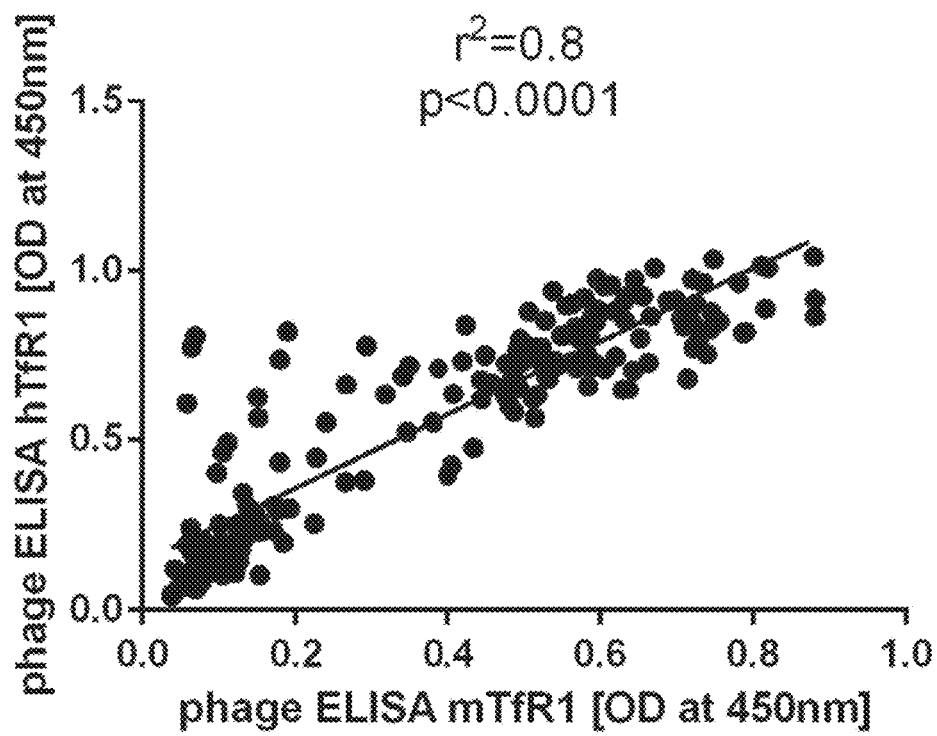
FIG. 3. Correlation of hTfR and mTfR binding in Clone C variants. Pearson's correlation analysis of binding to human and mouse TfR-1 by phage ELISA after one round of panning the pooled library of Clone C variants.

The five libraries were pooled together before phage panning on recombinant human TfR-1. Two rounds of selection were performed in total, which improved the percentage of positive clones from 30% to 70% after round one (FIG. 2) with no further improvement after round two. Phage ELISA performed with human and mouse TfR-1 showed that the variants retained the cross-species reactivity of the parent Clone C (FIG. 3) as generally described in WO2016/077840.

Figure 4:
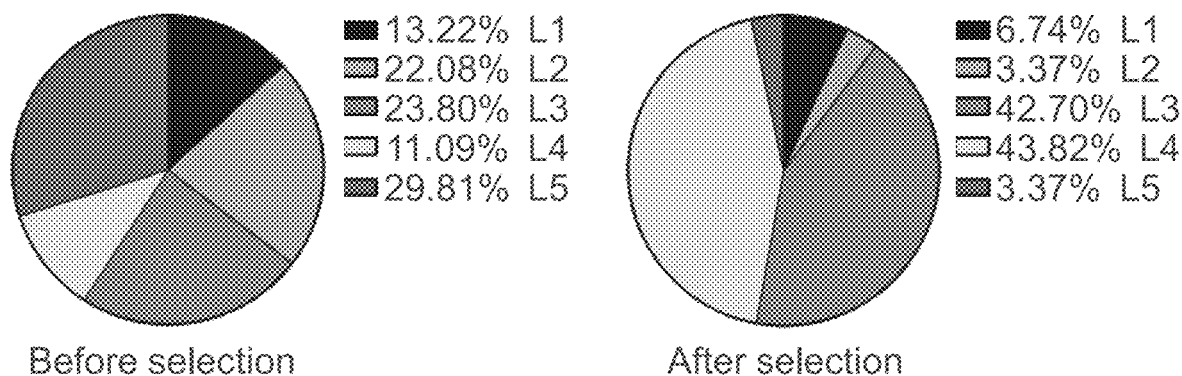
FIG. 4. Library Representation of Clone C Variants. Percentage representation of individual phage libraries (L1, L2, L3, L4 and L5) in the mixed library before and after two rounds of panning on recombinant human TfR-1.

Over 400 clones in total were sequenced both before and after selection process. The sequence analysis revealed a shift from relatively equally distributed sub-libraries in the starting library mix towards over representation of library 3 and 4 (corresponding to residues 5-9 in CDR3 region of Clone C) after the selection process (FIG. 4). A percentage-change analysis of residues before and after selection was performed without division into sub-libraries. This indicated that the binding to TfR-1 relied on the conservation residues VQYP in position 1-4 (SEQ ID NO. 12) and FW in position 10-11. The analysis also indicates that substitutions were tolerated within residues SYNNY (position 5-9; SEQ ID NO. 13) in middle part of the CDR3.

Example 2

Brain Uptake of Clone C Variants as Fc Fusions

Variants of Clone C with confirmed ELISA binding to mTfR-1 were reformatted as bivalent VNAR-Fc fusions and tested in mice for brain penetration. In particular, forty-seven (47) clones were reformatted as bivalent VNAR-Fc by cloning the VNARs into the commercial pFUSE vector (pFUSE-hIgG1e3-Fc2). The Fc region of the protein contained CH2 and CH3 domains with the hinge that served as a flexible spacer between the two parts of the Fc-fusion protein. N-termini of the construct contained the IL2 signal sequence to allow secretion. A HEK Expi293 expression system was used to transiently express the proteins. The VNAR clones were expressed as Fc formats in small (1 ml) scale in 96-well plates. Media was collected and used directly for ELISA in order to confirm binding to mouse and human TfR-1.

These VNAR-Fcs were further tested in animal experiments for their blood brain barrier penetration ability. Five animals per group were used. Mice were intravenously injected with 25 nmol/kg (approximately 2 mg/kg) of purified VNAR-Fc constructs and the brains were collected 18 hours post injection. The whole brains were homogenised in 1% Triton X-100 and used for ELISA with anti-Fc capture and detection antibody. Standard curves were prepared individually for each of the molecules to assure accuracy of the calculated concentrations. A control VNAR-Fc that binds at nM concentration to TfR-1 but lacks a blood brain penetration property was used as negative control. Clone C showed approximately 10-fold higher signal than the negative control, reaching 5 nM concentration in the whole brain tissue.

The results showed that brain penetration of 5 clones was improved; another five had a similar level of brain uptake to the parental clone and ten clones showed brain concentration <0.8 nM, which was considered insignificant (FIG. 5). Clone C is marked with an *.

Table 1 lists the amino acid sequences of the Clone C variants that penetrate the brain. Detailed binding kinetic analyses were performed to gain a better understanding of the relationship between affinity and brain penetration of the Clone C variants. Biacore surface plasmon resonance (SPR) analysis using immobilised mouse and human TfR-1 was performed for selected clones (Table 2).

Pearson's correlation analyses revealed a significant linear correlation (r2=0.6, p value=0.001) between brain penetration and association rate (ka) for both the human and human TfR1 (FIGS. 6A and 6B). There was also a strong correlation (r2=0.9, p value=0.001) in the binding ka between mouse and human TfR1 (FIG. 6C). There was no correlation between the dissociation rate (kd) and brain transport (FIG. 7). The dissociation constant (KD) showed no linear correlation, however the trend indicated that high affinity was beneficial for BBB transport with a possible KD threshold value required for brain penetration (FIG. 8). The conserved ends of the CDR3 confer high affinity binding, which is necessary but insufficient for high brain penetration since there are also high affinity binders with poor brain penetration.

TABLE 1

Brain Penetrant CDR3s of Clone C variants

| SEQ ID NO. | Variant | CDR3 |
|---|---|---|
| 3 | Clone C | VQYPSYNNYFWCDV |
| 14 | 1 | AQRPSYNNYFWCDV |
| 15 | 2 | LQRPSYNNYFWCDV |
| 16 | 3 | VQHPSYNNYFWCDV |
| 17 | 4 | VQRPSYNNYFWCDV |
| 18 | 5 | VQSPSYNNYFWCDV |
| 19 | 6 | VQWPSIQSPFWCDV |
| 20 | 7 | VQWPSLSSPFWCDV |
| 21 | 8 | VQWPSYNNYFWCDV |

TABLE 1-continued

Brain Penetrant CDR3s of Clone C variants

| SEQ ID NO. | Variant | CDR3 |
|---|---|---|
| 22 | 9 | VQWPTLSSPFWCDV |
| 23 | 10 | VQYPFLENYFWCDV |
| 24 | 11 | VQYPHYNNYFWCDV |
| 25 | 12 | VQYPQQDNPFWCDV |
| 26 | 13 | VQYPQQDNYFWCDV |
| 27 | 14 | VQYPQQDRPFWCDV |
| 28 | 15 | VQYPQQPNYFWCDV |
| 29 | 16 | VQYPQQTRPFWCDV |
| 30 | 17 | VQYPQYDNYFWCDV |
| 31 | 18 | VQYPQYPNYFWCDV |
| 32 | 19 | VQYPRTNNYFWCDV |
| 33 | 20 | VQYPSHNNYFWCDV |
| 34 | 21 | VQYPSIFNYFWCDV |
| 35 | 22 | VQYPSNNNYFWCDV |
| 36 | 23 | VQYPSQQNYFWCDV |
| 37 | 24 | VQYPSWDNYFWCDV |
| 38 | 25 | VQYPSYDNPFWCDV |
| 39 | 26 | VQYPSYDRPFWCDV |
| 40 | 27 | VQYPSYHNYFWCDV |
| 41 | 28 | VQYPSYNHYFWCDV |
| 42 | 29 | VQYPSYNNHFWCDV |
| 43 | 30 | VQYPSYNNLYWCDV |
| 44 | 31 | VQYPSYRSLFWCDV |
| 45 | 32 | VQYPSYTRAFWCDV |
| 46 | 33 | VQYPSYTRPFWCDV |
| 47 | 34 | VQYPTNENYFWCDV |
| 48 | 35 | VQYPVQDNYFWCDV |
| 49 | 36 | VQYPVQPNYFWCDV |
| 50 | 37 | VQYPVYDNYFWCDV |
| 51 | 38 | VQYPVYPNYFWCDV |

TABLE 2

Kinetic Data for Clone C Variants

| CDR3 | hTfR1 ka (1/Ms) | hTfR1 kd (1/s) | hTfR1 KD (M) | mTfR1 ka (1/Ms) | mTfR1 kd (1/s) | mTfR1 KD (M) |
|---|---|---|---|---|---|---|
| Clone C | 2.40E+05 | 1.45E−04 | 6.04E−10 | 2.14E+05 | 1.91E−04 | 8.92E−10 |
| 1 | 1.15E+05 | 3.22E−04 | 2.79E−09 | 1.06E+05 | 1.54E−04 | 1.45E−09 |
| 2 | 1.37E+04 | 6.77E−04 | 4.94E−08 | 1.49E+04 | 1.44E−04 | 9.65E−09 |
| 3 | 3.81E+05 | 1.19E−04 | 3.11E−10 | 3.55E+05 | 2.56E−04 | 7.20E−10 |
| 4 | 3.52E+04 | 3.25E−04 | 9.21E−09 | 3.74E+04 | 8.76E−05 | 2.34E−09 |
| 5 | 4.11E+05 | 3.02E−04 | 7.33E−10 | 2.78E+05 | 1.35E−04 | 4.86E−10 |
| 6 | 4.95E+04 | 9.55E−04 | 1.93E−08 | | | |
| 7 | 1.10E+05 | 7.02E−05 | 6.36E−10 | 1.19E+05 | 3.39E−05 | 2.86E−10 |
| 8 | 1.15E+05 | 5.19E−04 | 4.50E−09 | 6.35E+04 | 4.32E−04 | 6.81E−09 |
| 9 | 2.85E+04 | 7.54E−04 | 2.65E−08 | 3.83E+04 | 9.32E−05 | 2.43E−09 |
| 10 | 1.40E+05 | 3.89E−04 | 2.79E−09 | | | |
| 11 | 1.91E+05 | 9.01E−05 | 4.72E−10 | 1.77E+05 | 5.17E−05 | 2.91E−10 |
| 12 | 2.03E+05 | 1.42E−04 | 6.99E−10 | 1.79E+05 | 1.28E−04 | 7.15E−10 |
| 13 | 2.97E+05 | 1.70E−04 | 5.74E−10 | 2.48E+05 | 4.09E−05 | 1.65E−10 |
| 14 | 2.45E+04 | 1.56E−04 | 6.34E−09 | 1.99E+04 | 1.33E−04 | 6.69E−09 |
| 15 | 2.33E+05 | 5.78E−05 | 2.48E−10 | 2.79E+05 | 2.52E−05 | 9.02E−11 |
| 15 | 3.02E+05 | 1.02E−04 | 3.37E−10 | 3.59E+05 | 1.33E−04 | 3.69E−10 |
| 17 | 1.85E+05 | 8.13E−05 | 4.39E−10 | 1.80E+05 | 3.72E−05 | 2.07E−10 |
| 18 | 3.60E+05 | 1.13E−04 | 3.14E−10 | 3.12E+05 | 2.69E−04 | 8.63E−10 |
| 19 | 2.39E+05 | 1.09E−04 | 4.54E−10 | 2.16E+05 | 2.87E−04 | 1.33E−09 |
| 20 | 5.19E+04 | 2.91E−04 | 5.61E−09 | 5.01E+04 | 1.03E−04 | 2.06E−09 |
| 21 | 9.55E+04 | 4.37E−04 | 4.58E−09 | | | |
| 22 | 7.42E+04 | 6.27E−04 | 8.44E−09 | | | |
| 23 | 3.17E+05 | 4.32E−04 | 1.36E−09 | | | |
| 24 | 8.88E+04 | 1.94E−04 | 2.19E−09 | | | |
| 25 | 3.33E+04 | 5.69E−04 | 1.71E−08 | | | |

Table 3 summarizes the amino acids found at the different positions in the CDR3s of the Clone C variants that penetrated the BBB.

TABLE 3

Clone C Variants: Positional Substitutions
CDR3 genus (SEQ ID NO. 52)

| P1 | P2 | P3 | P4 | P5 | P6 | P7 | P8 | P9 | P10 | P11 | P12 | P13 | P14 |
|----|----|----|----|----|----|----|----|----|-----|-----|-----|-----|-----|
| V  | Q  | Y  | P  | S  | Y  | N  | N  | Y  | F   | W   | C   | D   | V   |
| A  |    | H  |    | F  | H  | D  | H  | A  | Y   |     |     |     |     |
| L  |    | R  |    | H  | I  | E  | R  | H  |     |     |     |     |     |
|    |    | S  |    |    | Q  | L  | S  | L  |     |     |     |     |     |
|    |    | W  |    |    | R  | F  |    | P  |     |     |     |     |     |
|    |    |    |    |    | S  | H  |    |    |     |     |     |     |     |
|    |    |    |    |    | T  | P  |    |    |     |     |     |     |     |
|    |    |    |    |    | V  | Q  |    |    |     |     |     |     |     |
|    |    |    |    |    |    | R  |    |    |     |     |     |     |     |
|    |    |    |    |    |    | S  |    |    |     |     |     |     |     |
|    |    |    |    |    |    | T  |    |    |     |     |     |     |     |

Example 3. Restricted, Random Mutagenesis of Clone H

Clone H, a human and mouse TfR-binding VNAR was obtained by in vivo selection of brain penetrating phages as described in Examples 1 and 2 of Intl. Appin. No. PCT/US2017/045592, filed Aug. 4, 2017(now WO2018/031424). The VNAR domain amino acid sequence for Clone H is:

(SEQ ID NO. 6)
ARVDQTPQTITKETGESLTINCVLR_DSNCELS_STYWYRKKSGSTNEE

SISKGGRYVETVNSGSKSFSLRINDLVVEDSGTYRCNVQQFPSSS

NGRYWCDVYGGGTAVTVNA.
The CDR1 domain is bolded and italicized;
the CDR3 domain is underlined and bolded.

Figure 9:
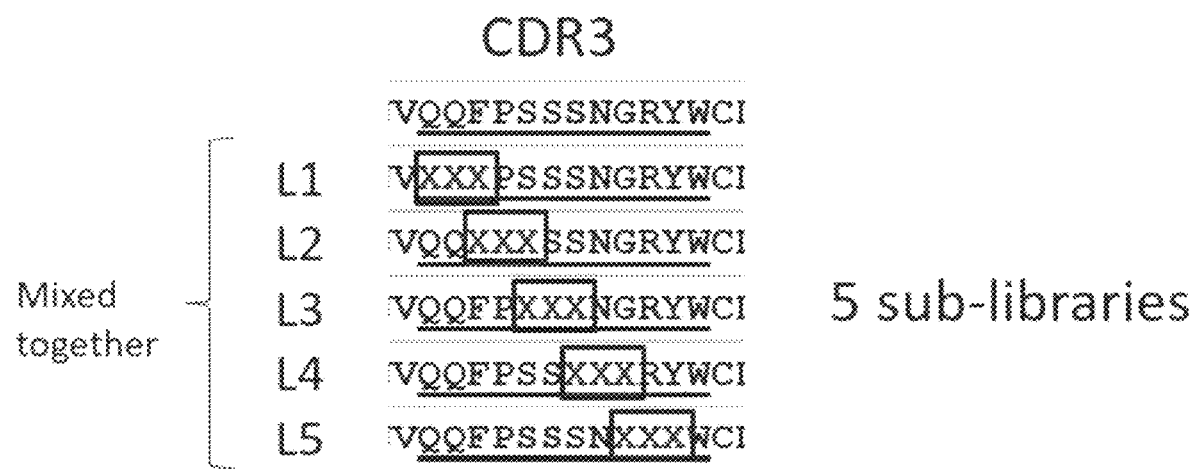
FIG. 9. Phage Library Mutagenesis Design for Clone H. Five phage libraries based on Clone H CDR3 were designed. In each library, three adjacent residues were randomized with one residue overlap between libraries. The phage libraries were pooled together before panning on recombinant human TfR1. The top line shows the amino acid sequence of the Clone H CDR3 without its last two amino acids (SEQ ID NO. 79) and the remaining lines show the sequences of the mutagenized CDR3 sequences used in the five libraries (SEQ ID NOS. 80-84, from top to bottom).

To improve BBB shuttling function of Clone H, its CDR3 region was subjected to a restricted randomization process. Five new phage libraries were prepared based on the CDR3 with three subsequent residues randomized in each library and with the offset of two residues (FIG. 9).

The five restricted random mutagenized VNARs were inserted into modified pSEX81 (Progen) plasmid and used for M13-based phage display (Hasler, Flajnik et al. 2016). Recombinant human TfR-1 (Sino Biological, 11020-H07H) protein was biotinylated using Sulfo-NHS-Biotin EZ-Link kit (Thermo, 21326) and subsequently used at 100 nM concentration for each round of soluble phase in vitro selection (Griffiths, Williams et al. 1994). Magnetic streptavidin coupled Dynabeads (Thermo) were used for pulldown of the protein that, following washes, was eluted with 100 nM triethylamine, then pH adjusted and subsequently used for infection of E. coli ER2738 bacterial strain. The output titer was calculated by counting antibiotic resistant colonies and the culture was super-infected with M13K07 helper phage in order to produce phage for a round of selection.

Figure 10:
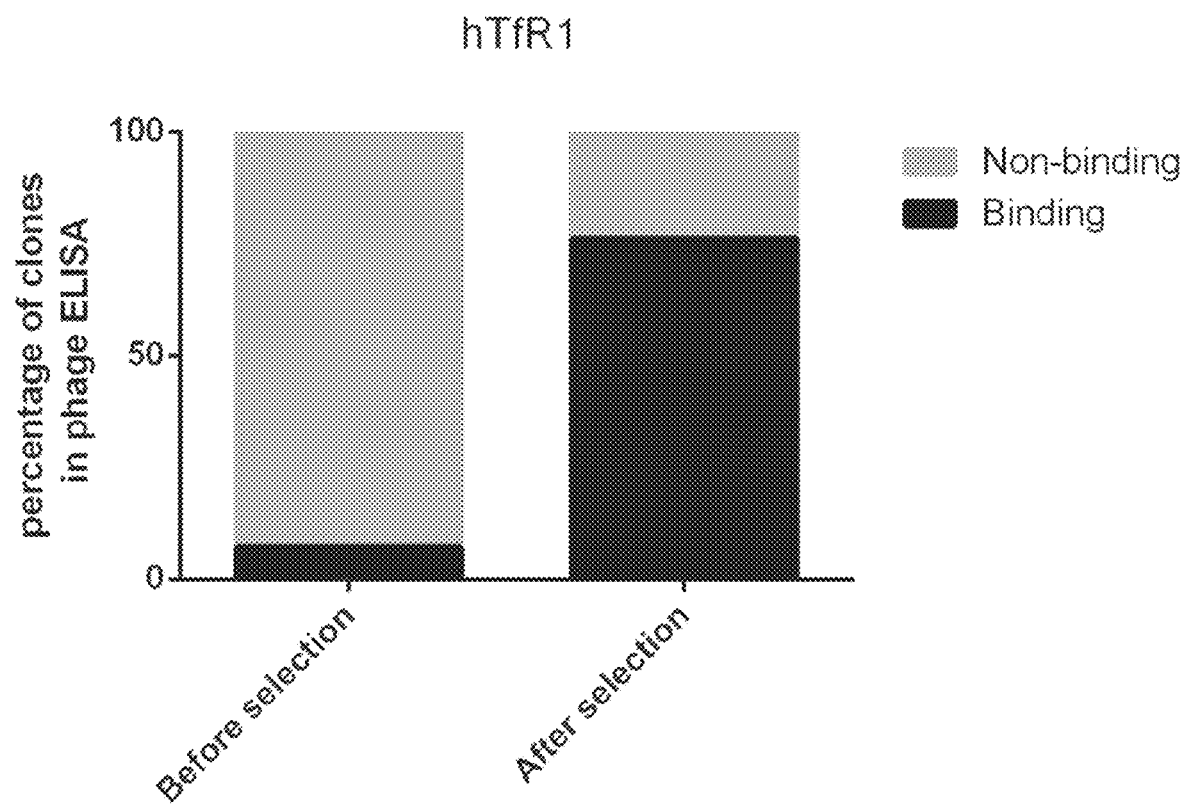
FIG. 10. Enrichment of TfR-binding Clone H Variants After Mutagenesis. Percentage of binding (over double the value of the negative control) and non-binding (below double the value of the negative control) clones to human TfR-1 before and after one round of panning of the pooled library of Clone H variants as determined by phage ELISA.

The five libraries were pooled together before phage panning on recombinant human TfR-1. Two rounds of selection were performed in total, which improved the percentage of positive clones from 7% to 76% after round one (FIG. 10).

Figure 11:
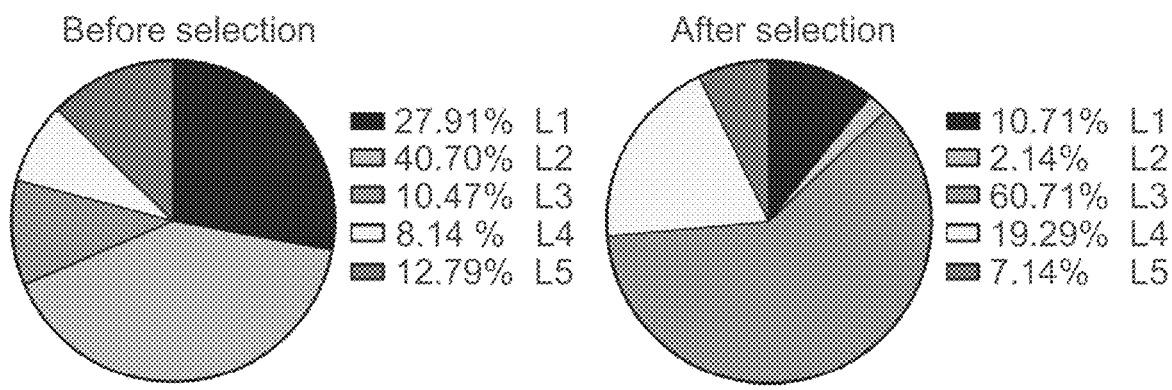
FIG. 11. Library Representation of Clone H Variants. Percentage representation of individual phage libraries (L1, L2, L3, L4 and L5) in the mixed library before and after one round of panning on recombinant human TfR-1.

Over 400 clones in total were sequenced both before and after selection process. The sequence analysis revealed a shift from relatively equally distributed sub-libraries in the starting library mix towards over representation of library 3 and 4 (corresponding to residues 5-9 in CDR3 region of clone H) after the selection process (FIG. 11). The sequence analysis revealed a shift from original sub-library distribution (L1 28%, L2 41%, L3 10%, L4 8% and L5 13%) in the starting library mix towards over representation of library 3 and 4 (L3 60% and L4 19%, corresponding to residues 5-9 in CDR3 region of Clone H) in the clones after the selection process. The main drop in library representation was observed for L2 from original 41% to 2%.

A percentage-change analysis of residues before and after selection was performed without division into sub-libraries. This indicated that the binding to TfR-1 relied on the conservation residues QQFP in position 1-4 (SEQ ID NO. 53) and YW in position 11-12. The analysis also indicates that substitutions were tolerated within residues SYNNG in middle part of the CDR3 (position 5-9; SEQ ID NO. 54).

Example 4. Brain Uptake of Clone H Variants as Fc Fusions

Variants of Clone H with confirmed ELISA binding to mTfR-1 were reformatted as bivalent VNAR-Fc fusions and tested in mice for brain penetration. In particular, eleven (11) clones were reformatted as bivalent VNAR-Fc by cloning the VNARs into the commercial pFUSE vector (pFUSE-hIgG1e3-Fc2). The Fc region of the protein contained CH2 and CH3 domains with the hinge that served as a flexible spacer between the two parts of the Fc-fusion protein. N-termini of the construct contained the IL2 signal sequence to allow secretion. A HEK Expi293 expression system was used to transiently express the proteins. The VNAR clones were expressed as Fc formats in small (1 ml) scale in 96-well plates. Media was collected and used directly for ELISA in order to confirm binding to mouse and human TfR-1.

These VNAR-Fcs were further tested in animal experiments for their blood brain barrier penetration ability. Five animals per group were used. Mice were intravenously injected with 25 nmol/kg (approximately 2 mg/kg) of purified VNAR-Fc constructs and the brains were collected 18 hours post injection. The whole brains were homogenised in 1% Triton X-100 and used for ELISA with anti-Fc capture and detection antibody. Standard curves were prepared individually for each of the molecules to assure accuracy of the calculated concentrations. A control VNAR-Fc that binds at nM concentration to TfR-1 but lacks a blood brain penetration property was used as negative control. Clone H showed approximately 2-fold higher signal than the negative control.

The results showed four clones to have improved brain penetration, another four showed similar brain uptake as Clone H and three clones achieved brain concentration below Clone H (FIG. 12

Table 4 lists the amino acid sequences of the Clone H variants that penetrate the brain. Detailed binding kinetic analyses were performed to gain a better understanding of the relationship between affinity and brain penetration of the Clone H variants. Biacore surface plasmon resonance (SPR) analysis using immobilized mouse and human TfR-1 was performed for the clones (Table 5). Measured on-rates (ka) ranged from 1.9E+04 to 7.4+04 (1/Ms), off-rates (kd) from 6.2E-04 to 9.1E-05 (1/s) and affinity (KD) from 2.5 E-09 to 2.5 E-08 (M) for mouse TfR1. A correlation between kinetic data and brain uptake was not observed for Clone H variants due to a the small spread of brain penetration levels and to the limited number of clones analysed.

TABLE 4

Brain Penetrant CDR3s of Clone H Variants

| SEQ ID NO | Variant | CDR3 |
|---|---|---|
| 55 | 1 | VQWPSSSNGRYWCDV |
| 56 | 2 | QQFPSSWPFRYWCDV |
| 57 | 3 | QQFPSWGNGRYWCDV |
| 58 | 4 | QQFPSRFNGRYWCDV |
| 59 | 5 | QQFPNRWNGRYWCDV |
| 60 | 6 | QQFPSRNNGRYWCDV |
| 61 | 7 | QQFPTRINGRYWCDV |
| 62 | 8 | QQFPSRHNGRYWCDV |
| 63 | 9 | QQFPNPPNGRYWCDV |
| 64 | 10 | QQFPSWFNGRYWCDV |

TABLE 5

Kinetic Data for Clone H Variants

| CDR3 | hTfR1 ka (1/Ms) | hTfR1 kd (1/s) | hTfR1 KD (M) | mTfR1 ka (1/Ms) | mTfR1 kd (1/s) | mTfR1 KD (M) |
|---|---|---|---|---|---|---|
| Clone H | 3.01E+05 | 1.83E−03 | 6.11E−09 | 3.58E+04 | 9.11E−05 | 2.54E−09 |
| 1 | 5.08E+04 | 1.21E−04 | 2.38E−09 | 4.16E+04 | 1.95E−04 | 4.69E−09 |
| 2 | 1.07E+05 | 4.03E−04 | 3.77E−09 | 1.91E+04 | 4.82E−04 | 2.52E−08 |
| 3 | 5.39E+04 | 2.54E−04 | 4.71E−09 | 4.89E+04 | 2.73E−04 | 5.59E−09 |
| 4 | 1.15E+05 | 1.83E−03 | 1.59E−08 | 2.83E+04 | 3.52E−04 | 1.24E−08 |
| 5 | weak binding | | | 3.37E+04 | 3.69E−04 | 1.10E−08 |
| 6 | weak binding | | | 2.53E+04 | 4.17E−04 | 1.65E−08 |
| 7 | weak binding | | | 2.56E+04 | 3.99E−04 | 1.56E−08 |
| 8 | 3.80E+04 | 9.48E−04 | 2.50E−08 | 7.36E+04 | 6.18E−04 | 8.40E−09 |
| 9 | weak binding | | | weak binding | | |
| 10 | 7.99E+04 | 2.69E−04 | 3.37E−09 | 5.05E+04 | 2.79E−04 | 5.53E−09 |

Table 6 provides a summary of the amino acids found at the different positions in the CDR3s of the Clone H variants that penetrated the BBB.

FIG. 13 shows a comparison of the amino acids in CDR3 of Clone C and Clone H. These two Type II VNARS are unusual in that the CDR3 cysteine which forms a disulfide with the cysteine in CDR1 is located at the C-terminus rather than the more usual mid-region location of CDR3. Interestingly, the N-terminal portion of CDR3 is highly conserved in both clones. Both clones are again similar in that their mid regions can tolerate substitutions with the highest degree of diversity in each found at position 7. Clone H can further tolerate an additional amino acid at position 10 and still retain activity.

TABLE 6

Clone H Variants: Positional Substitutions
CDR3 genus (SEQ ID NO. 65)

| P1 | P2 | P3 | P4 | P5 | P6 | P7 | P8 | P9 | P10 | P11 | P12 | P13 | P14 | P15 |
|---|---|---|---|---|---|---|---|---|---|---|---|---|---|---|
| Q | Q | F | P | S | S | S | N | G | R | Y | W | C | D | V |
| V | | W | | N | R | W | P | F | | | | | | |
| | | | | T | W | F | | | | | | | | |
| | | | | | P | P | | | | | | | | |
| | | | | | | G | | | | | | | | |
| | | | | | | N | | | | | | | | |
| | | | | | | H | | | | | | | | |
| | | | | | | T | | | | | | | | |
| | | | | | | P | | | | | | | | |

Detailed Methods for Examples 1-4
Small Scale (96-Well Plate) Expi293 Transfection The transient transfection Expi293 expression system (Thermo) was used following the manufacturer's manual. In brief, 425 µl of Expi293 cells at the concentration of 2.94×10$^6$/ml were plated into a 96-well block. 0.5 µg of each DNA was mixed with Opti-MEM media (Thermo) to make a total volume of 25 µl. 1.35 µl of expifectamine was mixed with 23.65 µl Opti-MEM media and after 5 minutes added to the DNA mix; then incubated for an additional 25 minutes. The cells were grown in an incubator at 350 rpm, 37° C. with 8% $CO_2$ overnight before enhancer 1 (2.5 µl) and enhancer 2 (25 µl) were added and the cells grown for 5 more days.

VNAR-Fc ELISA

Maxisorp™ plates (Nunc, Thermo) were coated with 100 µl of 1 µg/ml of recombinant mouse TfR-1 (Sino 50741-MO7H-100), human TfR1 (Sino 11020-H07H-100), HSA (Sigma A3139), mouse TfR2 (ACRO Biosystems TF2-M5269) and incubated at 4° C. overnight; to measure VNAR-Fc express levels the plate was coated with 1:500 diluted anti-Fc antibody (Sigma 12136). The next day the plates were blocked with 2.5% (w/v) in PBS with 0.1% Tween20 (PBST) for 1 hour at room temperature. Transfected cells were spun down at 2000 rpm for 10 minutes and the collected supernatant was mixed with milk in PBST to a final 2.5% concentration and incubated for 30 minutes. 100 µl of blocked supernatant was transferred into coated plates and incubated for 1 hour. Then the plates were washed with PBST and incubated with anti-Fc-peroxidase antibodies (1:5000) (Sigma A0170) in 2.5% milk in PBST for 30 min. The plates were washed and developed with TMB detection solution before stopping the reaction with 1% HCl. Absorbance was measured at 450 nm. A VNAR-Fc at known concentration was used for a standard curve to calculate VNAR-Fc expression level.

Competition ELISA—Variant 1

Maxisorp™ plates (Nunc, Thermo) were coated with 100 µl of hTfR1 (Sino 11020-H07H-100) at the concentration of 5 µg/ml at 4° C. overnight. Plates were washed with PBST and blocked for 1 h with 2% BSA in PBST. Plates were washed again before adding 100 µl of human biotinylated Tf at the concentration of 2.5 µM (Sigma T3915) in 0.1% BSA in PBST and subjected to al hour incubation at room temperature. Then 100 µl of VNAR-Fc at the concentration ranging from pM to µM was added and further incubated for 1 hour. Following washing, 100 µl of 1:5000 diluted in 0.5% BSA in PBST detection antibody anti-human Fc peroxidase-conjugated (Sigma A0170) was added and incubated for 1 hour. The plates were washed and developed with TMB detection solution before stopping the reaction with 1% HCl. Absorbance was measured at 450 nm. A VNAR-Fc at known concentration was used for a standard curve to calculate VNAR-Fc expression level.

Competition ELISA—Variant 2

Maxisorp plates (Nunc, Thermo) were coated with 100 µl of hTfR1 (Sino 11020-H07H-100) at the concentration of 5 µg/ml at 4° C. overnight. Plates were washed with PBST and blocked for 1 h with 2% BSA in PBST. Washed again before adding 100 µl of human biotinylated Tf at the concentration ranging from pM to µM (Sigma T3915) in 0.1% BSA in PBST. Then incubated for 1 hour at room temperature. Subsequently 100 µl of VNAR-Fc or holo-Tf (Sigmal T4132-100MG) at the concentration of 2.44 nM was added and further incubated for 1 hour. Following washing, 100 µl of either 1:5000 or 1:20,000 diluted in 0.5% BSA in PBST detection antibody anti-human Fc peroxidase-conjugated (Sigma A0170) or streptavidin-peroxidase (Fitzgerald 65R-S104PHRP) was added and incubated for 1 hour, respectively. The plates were washed and developed with TMB detection solution before stopping the reaction with 1% HCl. Absorbance was measured at 450 nm. A VNAR-Fc at know concentration was used for standard curve to calculate VNAR-Fc expression level.

Expression and Purification of VNAR-Fc Fusion Proteins

Selected VNARs were expressed as N-terminal fusions to the human IgG1-Fc region (CH2 and CH3 domains) engineered for the reduced ADCC and CDC of pFUSE-hIgG1e3-Fc2 plasmid. Briefly, cDNAs encoding the VNARs were synthesized and cloned using EcoRV and BglII restrictions site. In addition, the IgG hinge region was extended by incorporating a flexible linker sequences comprising glycine- and serine-rich residues $(G_xS_x)_n$, where x and n typically=0-4 (SEQ ID NO. 66). The IL2 secretory signal sequence (IL2Ss) of the parent plasmid was retained.

Expi293F™ (Invitrogen) cells were cultured in Expi293 expression medium (Invitrogen) supplemented with penicillin (100 U/ml), streptomycin (100 □g/ml) and maintained in a humidified shaking incubator at 37° C. and 5% $CO_2$. Cells were transfected using ExpiFectamine™ 293 Transfection Kit (Invitrogen) according to the manufacturer's protocol. Cells removed from the expression medium by centrifugation 5 days post transfection. The media was filtered and loaded onto PBS equilibrated Mab Select SuRe™ columns (GE Life Sciences). The columns were washed with 10 volumes of PBS and the recombinant protein eluted with linear gradient of 0.1M glycine, pH 2.5 and PBS. Fractions containing the proteins were pooled and buffer exchanged to PBS using Sephadex® 25 desalting columns (GE Life Sciences). Protein concentrations were estimated by absorbance at $280_{nm}$. Purified proteins were stored at −80° C. and once thawed maintained at 4° C. for a period of up to 2 weeks.

Binding Kinetic and Affinity Analysis

Binding kinetics of VNAR-Fcs was determined by surface plasmon resonance (Biacore T200, GE Healthcare). CMS chips were coated with anti-His antibodies (His Capture Kit, GE Healthcare) as recommended by the manufacturer and human or mouse his-tagged TfR1 (SinoBiological) at 10 ug/mL in HBS-EP+ (GE Healthcare) was captured at flow rate 10 ul/min (contact time 120 s). Single cycle kinetic analyses were performed by injecting VNAR-Fcs at increasing concentrations (0.98, 3.9, 15.6, 62.5 and 250 nM) in HBS-EP at flow rate 30 ul/min (contact time: 360 s; dissociation time after injecting 250 nM analyte: 1500 s). A flow cell without TfR1 captured served as a reference. Sensorgrams were fitted and kinetic constants were determined using Biacore T200 Evaluation software. Chips were regenerated in 10 mM Glycine-HCl, pH 1.5 (contact time: 120 s at flow rate 30 ul/min).

Example 5. VNAR-Mediated In Vivo Transport of a Therapeutic Antibody Across the Blood Brain Barrier Brain shuttling efficacy of Clone C was tested by genetically fusing the VNAR to different therapeutic antibodies. Rituximab (RIT), bapineuzumab (BAPI) and durvalumab (DUR) were used as model antibodies and different mono- and bi-valent formats were produced (FIG. 14).

Figure 15:
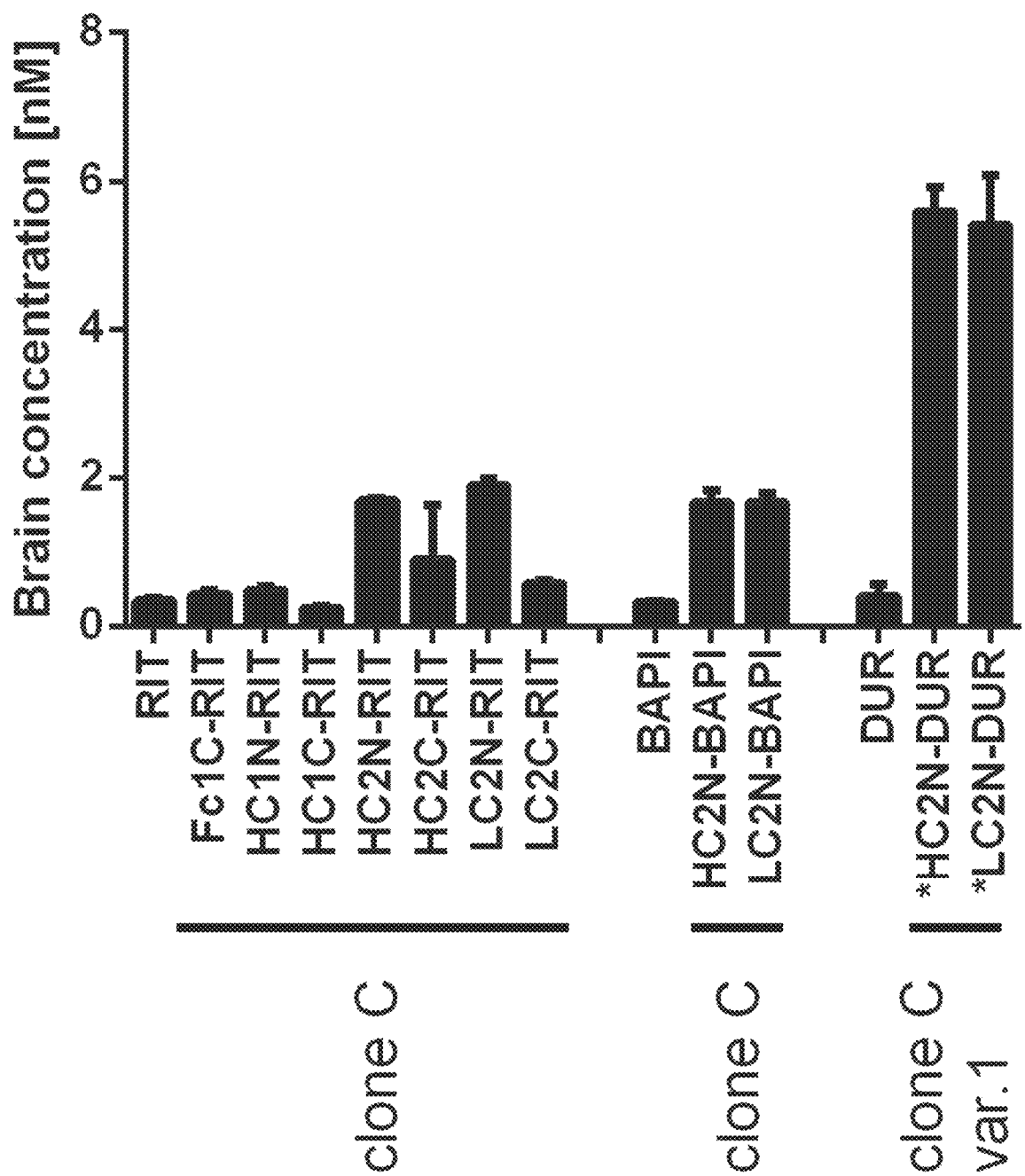
FIG. 15. Brain uptake of Clone C and Clone C Variant Fusion Proteins with Therapeutic Antibodies. Rituximab (RIT), bapineuzumab (BAPI) and durvalumab (DUR) fusions were administered intravenously to mice at 25 nmol/kg (equivalent to 3.5 mg/kg) and the brains were excised 18 hours later following cardiac perfusion. The VNAR-Fc concentration in brain homogenates was measured by human Fc capture ELISA and the values represent the mean±SD, N=3/group. Clone C var. 1 in the drawing has the sequence of variant 18 in Table 1.

Each mono- or bispecific format (Clone C-RIT) was injected into mice at the standard test concentration of 25 nmol/kg (corresponding to 4 mg/kg of unmodified rituximab antibody) and uptake in perfused brain was measured 18 hours later. Of these, Fc1N (monovalent) and scFv2N (bivalent) molecules, both N-terminal fusions, showed the best brain uptake producing over an 11-fold increase over unmodified rituximab (FIG. 15). Two other N-terminal bispecific formats produced approximately 5-fold increase over the unmodified antibody. C-terminal fusions showed poor brain penetration with HC2C and scFv2C averaging a 2-fold increase whereas the others were similar to unmodified rituximab. Plasma levels for all of the constructs were in the range of 50-170 nM, which did not account for the dramatic difference in brain uptake between the various formats.

The binding affinity (Table 7) values for mouse and human TfR1 were determined for the various Clone C-rituximab formats, as shown below.

TABLE 7

Binding Kinetics of Rituximab-Clone C in Different Formats to Mouse and Human TfR-1

| Clone C-Rituximab | human TfR-1 | | | mouse TfR-1 | | |
| --- | --- | --- | --- | --- | --- | --- |
| | ka (1/Ms) | kd (1/s) | KD (M) | ka (1/Ms) | kd (1/s) | KD (M) |
| Fc1N | 2.3E+04 | 1.6E−04 | 6.9E−09 | 4.2E+04 | 3.7E−04 | 8.8E−09 |
| Fc1C | 7.3E+03 | 3.2E−04 | 4.4E−08 | 9.2E+04 | 2.7E−03 | 2.9E−08 |
| HC1N | 3.4E+04 | 3.4E−04 | 1.0E−08 | 7.5E+04 | 9.4E−04 | 1.3E−08 |
| HC1C | 1.1E+04 | 4.9E−04 | 4.5E−08 | 6.6E+04 | 2.4E−03 | 3.6E−08 |
| HC2N | 3.1E+05 | 2.5E−04 | 8.2E−10 | 3.7E+05 | 1.3E−04 | 3.5E−10 |
| HC2C | 4.3E+04 | 2.0E−04 | 4.6E−09 | 4.8E+04 | 1.4E−04 | 3.0E−09 |
| LC2N | 2.9E+05 | 4.0E−04 | 1.4E−09 | 2.4E+05 | 1.8E−04 | 7.2E−10 |
| LC2C | 2.5E+04 | 2.4E−04 | 9.5E−09 | 2.9E+04 | 2.1E−04 | 7.4E−09 |

The bispecific formats had a relatively high affinity for the TfR-1, with KDs ranging from 350 pM to 45 nM. The monovalent versions had lower affinities than the bivalent versions and the close correlation between binding to the mouse and human receptors was retained for all the rituximab bispecific formats. The poor performance of the C-terminal fusion does not appear to be related to affinity for the receptor in vitro, which does not rule out steric interference with receptor binding in the capillary endothelium in vivo.

Figure 16:
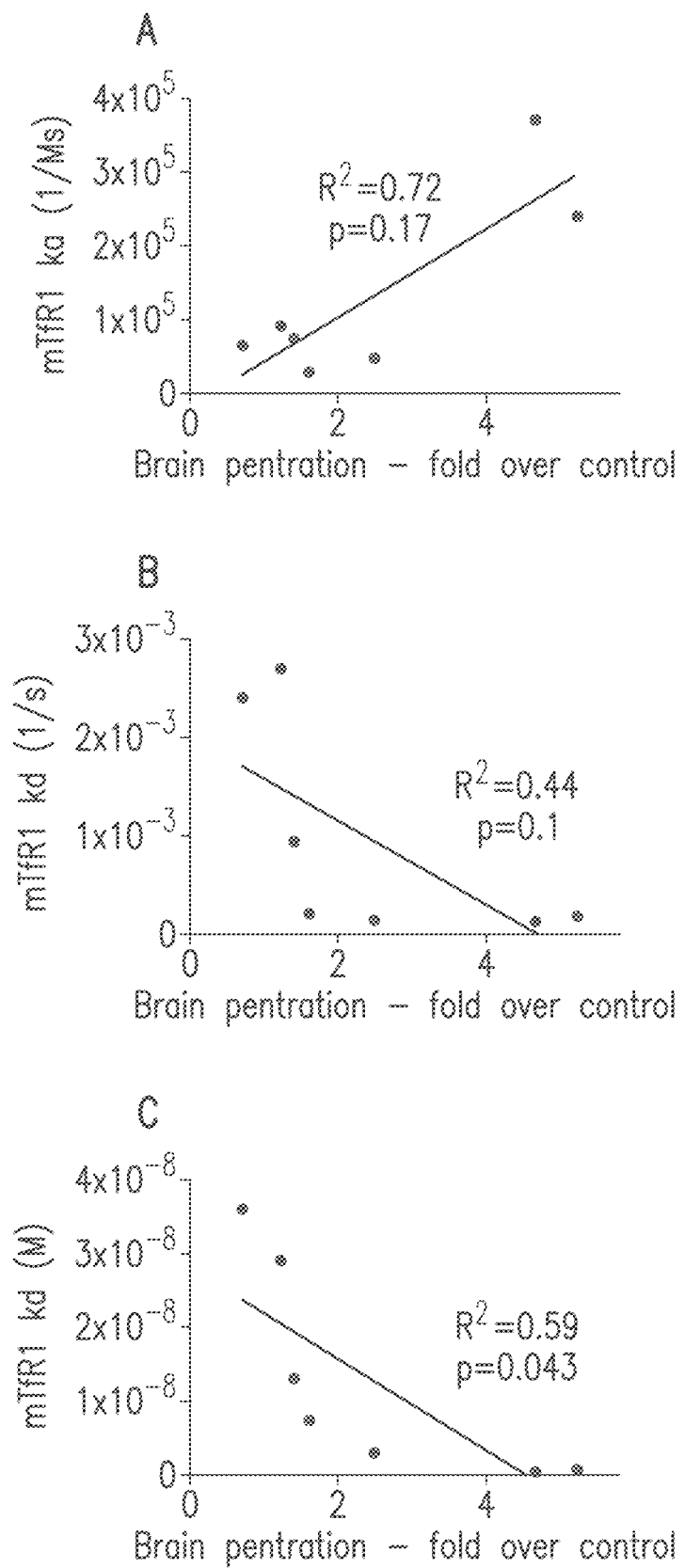
FIG. 16. Correlation of Mouse TfR-1 Binding Kinetics for Clone C-Rituximab Fusions. Pearson correlation analysis of brain penetration expressed as fold increase over control for (A) association rates (ka), (B) dissociation rates (kd) and (C) dissociation constants (KDs).
Figure 17:
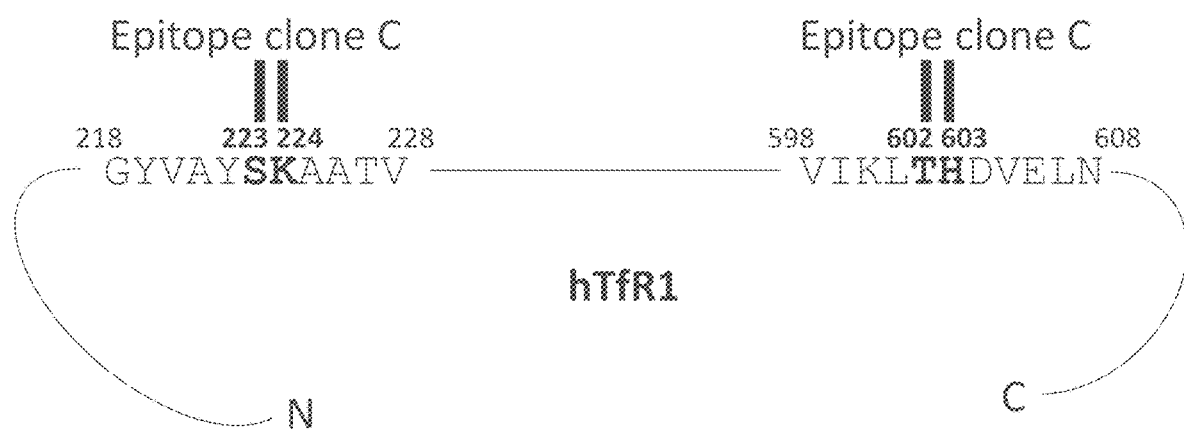
FIG. 17. Clone C Epitope Determined by Chemical Cross-linking to hTfR-1. The interaction interface between Clone C and human hTfR-1 was identified using chemical cross-linking, high-mass MALDI mass spectrometry and nLC-Orbitrap mass spectrometry. The hTfR-1 peptide sequences shown are SEQ ID NOS. 87 and 88, respectively, in order of appearance. The analysis indicates that the epitope included amino acids in positions: 223, 224, 602 and 603 of hTfR-1.

KD values were also plotted against the brain uptake as fold-increase over naked rituximab (FIG. 16). The data showed no linear and relatively poor logarithmic correlation between affinity to mouse TfR-1 and brain uptake. This stands in contrast to a previous report showing an inverse correlation between TfR binding and brain uptake for a bispecific antibody to TfR/BACE1 (Yu et al., Sci Transl Med. 2011. 3(84):84ra44). Low affinity TfR binding (~600 nM) was associated with the highest brain uptake whereas we found that VNAR with the highest brain uptake had sub-nanomolar binding affinity. The benefit of a high affinity BBB carrier is that biological levels can be achieved at lower doses, with fewer side effects and lower cost than a low affinity antibody, which requires higher doses for receptor mediated transport. The reason for this difference between the two TfR carriers is not yet clear, but may be related to the unique epitope and binding mode of the VNAR relative to IgG.

In summary, the RIT and BAPI were tested with fusions to the original Clone C whereas DUR was fused to Clone C variant 18 using the methods above. The DUR-Clone C variant 1 which showed the highest brain penetration as Fc format. N-terminal bi-valent formats showed the best brain penetration with Clone C variant 18 (for sequence see Table 1), which increased the brain transport nearly 3-fold in comparison to original Clone C (FIG. 15). Similar to previous observation with Clone C variants, RIT formats that had the fastest association rate (ka) measured by Biacore also showed the most efficient brain penetration (FIG. 16). The dissociation rate (kd) remained insignificant in Pearson correlation analysis. Affinity (KD) showed a trend similar to Clone C variants where high affinity clones gave more efficient brain penetration.

Example 6. Epitope Mapping of Clone C by Chemical Cross-Linking

A combination of chemical cross-linking and high-resolution mass spectrometry was used to determine the epitope of Clone C on the hTfR1 antigen. Protein samples (recombinant human TfR1 ectodomain and clone C VNAR formatted as a hFc fusion protein) were incubated with a mixture of deuterated cross-linkers (Bich et al. 2010) and subjected to multi-enzymatic cleavage. After enrichment of the cross-linked peptides, the samples were analyzed by high resolution mass spectrometry (nLC-Orbitrap MS) using XQuest and Stavrox software. The cross-linked sites were mapped to the 3D crystal structure of human TfR1 (RCSB: 1SUV; (Cheng et al. 2004) using PyMOL Molecular Graphics System.

Six cross-linking events were detected between peptides belonging to the hTfR1 antigen and peptides belonging to Clone C. nAA1 and nAA2 indicate the position of cross-links in hTfR1 and Clone C, respectively. The analysis indicated that the putative epitope included amino acids on hTfR1: 223, 224, 602 and 603 (Table 8 and FIG. 17).

The two putative binding sites were further evaluated by mapping the residues onto the crystal structure of the hTfR-1-Tf complex (PDB: 1SUV; (Cheng et al. 2004). The putative epitope at 602-603 was located on the interface of the receptor at the cell membrane and appeared to be inaccessible to the VNAR with Tf bound to the receptor (FIG. 18), suggesting a possible competitive interaction between Tf and Clone C. However, Clone C has been shown not to compete with Tf for binding either the receptor ectodomain in vitro or the native receptor in vivo (WO2018/031424). In addition, the corresponding cross-linked site on the Clone C peptide was partially located within CDR1 loop, which is not the main antigen recognition region site for the VNAR (Table 8 and FIG. 19). Therefore, it was likely that these contacts arose as an artefact from using the receptor ectodomain lacking its native membrane attachment in the crosslinking experiments.

The interaction interface identified around hTfR-1 amino acids 223-224 is more likely to be accurate since it is a highly accessible site on the apical domain of the receptor and the corresponding cross-linked residues on the Clone C peptide were near the CDR3 (Table 8 and FIGS. 18 and 19). Cross-linking experiments sometimes fail to identify the precise interaction of the CDR3 with the antigen due to the accessibility of cross-linkers and/or the orientation and distances between the molecules upon complexing. Nevertheless, a site close to the CDR3 is indicative of a true epitope so further studies were performed.

TABLE 8

Cross-linked Peptides between hTfR-1 and Clone C

| Event | hTfR-1 (AA number) | Clone C (AA number) | nAA1 | nAA2 | Digestion Enzyme |
|---|---|---|---|---|---|
| 1 | VAYSKAATVTGKL 220-232 | SSTYWY 35-40 | 224 | 38 | chymotrypsin |
| 2 | THDVELNL 602-609 | SSTYWY 35-40 | 602 | 37 | chymotrypsin |
| 3 | THDVELNL 602-609 | SSTYWY 35-40 | 603 | 35 | chymotrypsin |
| 4 | THDVELNL 602-609 | SSTYWY 35-40 | 603 | 36 | chymotrypsin |
| 5 | THDVELNL 602-609 | SSTYWY 35-40 | 603 | 37 | chymotrypsin |
| 6 | VAYSK 220-224 | VTVNARS 106-112 | 223 | 107 | thermolysin |

The amino acid sequences of the hTfR-1 peptides in Table 8 are SEQ ID NO. 67 for the 220-232 peptide (event 1), SEQ ID NO. 68 for the 602-609 peptide (events 2-5), and SEQ ID NO. 69 for the 220-224 peptide (event 6). Similarly, the amino acid sequences of the Clone C peptides are SEQ ID NO. 70 for the 35-40 peptide (events 1-5) and SEQ ID NO. 71 for the 106-112 peptide (event 6). Note that the last three amino acids of the 106-112 peptide are from the hFc portion of the VNAR-hFc fusion.

Example 7. Epitope Mapping of Clone C by Alanine Scanning Mutants

To confirm the Clone C binding epitope, single alanine mutants were prepared in the region surrounding residues 223-224 (SK). Since Clone C was shown to be species cross-reactive (WO2018/031424), mouse TfR-1 was used because of the availability of the well-characterized 8D3 antibody as a positive control, which binds the apical domain of TfR-1 but does not compete with Clone C. Additionally, mouse trasnferrin (TO was used for expression control in transfected human cells with minimal background signal from the endogenous hTfR-1 expression.

Figure 18:
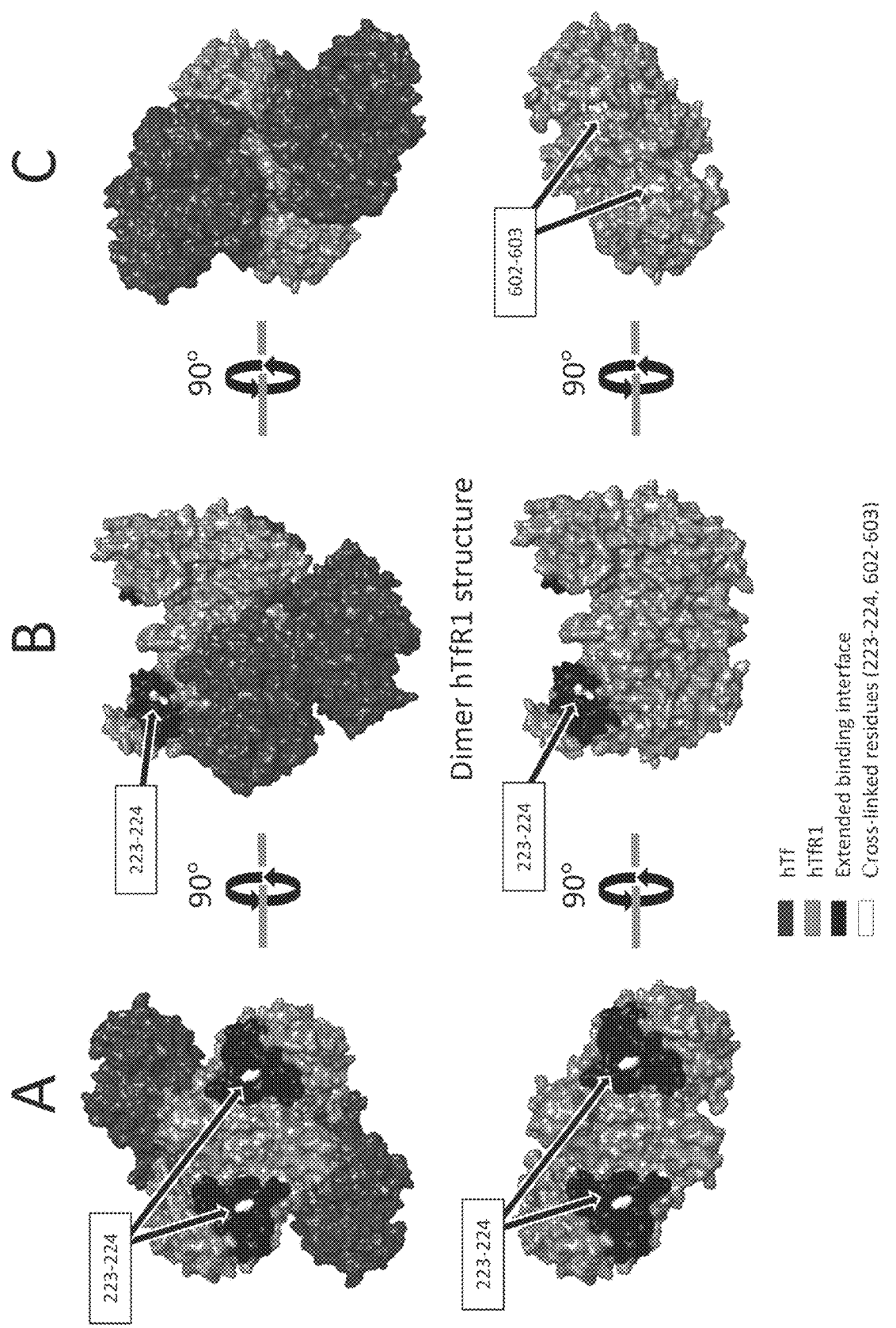
FIG. 18. Structural Model of hTfR-1 Indicating Residues Cross-linked to Clone C. (A), (B) and (C) represent top, side and bottom views of a space filling model of dimeric human TfR-1-transferrin (Tf) structure. The residues at hTfR-1 position 223-224 identified as cross-linking to Clone C (SK) are marked in white on hTfR-1 in the complex (PDB: 1 SUV). Surface residues that surround the identified site of interaction (extended binding interface) are marked in black. The extended binding interface was used further for identification of the exact binding epitope by alanine scanning.
Figure 19:
FIG. 19. Clone C Residues Cross-linked to hTfR-1. The figure depicts the sequence of Clone C (SEQ ID NO. 1) with the CDR1, HV2, HV4 and CDR3 regions (respectively) of the VNAR framework underlined. The large font indicates residues that were cross-linked to hTfR-1. (see discussion in the Examples). The distance between the last residue of the CDR3 (Y100) and the cross-linked residue (T107) as measured on a VNAR structure (PDB: 2I25) using PyMOL software is 18-24 Å, depending on the exact residue and atom used for the measurement.

Alanine mutants included the surface exposed amino acids marked in black in the structure (FIG. 18). The residues that were substituted with alanine are also marked in grey in the linear alignment of mouse and human TfR-1 sequences in FIG. 20. Each of the 48 alanine mutants were transiently expressed individually using the human Expi293 cell expression system (Thermo Fisher Scientific) following the manufacturer's directions.

Transfected Expi293 cells were harvested and 2×10⁵ cells were transferred into V-bottom 96-well plate for staining. The cells were blocked in PBS containing 1% BSA (FACS buffer) for 10 min on ice, centrifuged to remove the buffer and 1 µl of 8D3-hFc formatted antibody, Clone C-hFc or Clone C variants 18 and 13 (Table 1), all at 1 mg/ml, was added to the wells. The cells were co-stained with mouse Tf-Alexa647 (Jackson ImmunoResearch). After 30 minutes on ice, the cells were washed and incubated with anti-hFc-PE (eBioscience) for 20 minutes on ice, washed again and resuspended in 250 nl of FACS buffer containing 5 µl of propidium iodide (PI) to exclude dead cells from the analysis. The percentage of double-positive cells that stained with mTf and the tested antibody was determined on a CytoFlex cytometer (Beckman Coulter). The percentage of cells in the double positive quadrant (Q2) for WT mTfR-1 was used for normalization.

Figure 21:
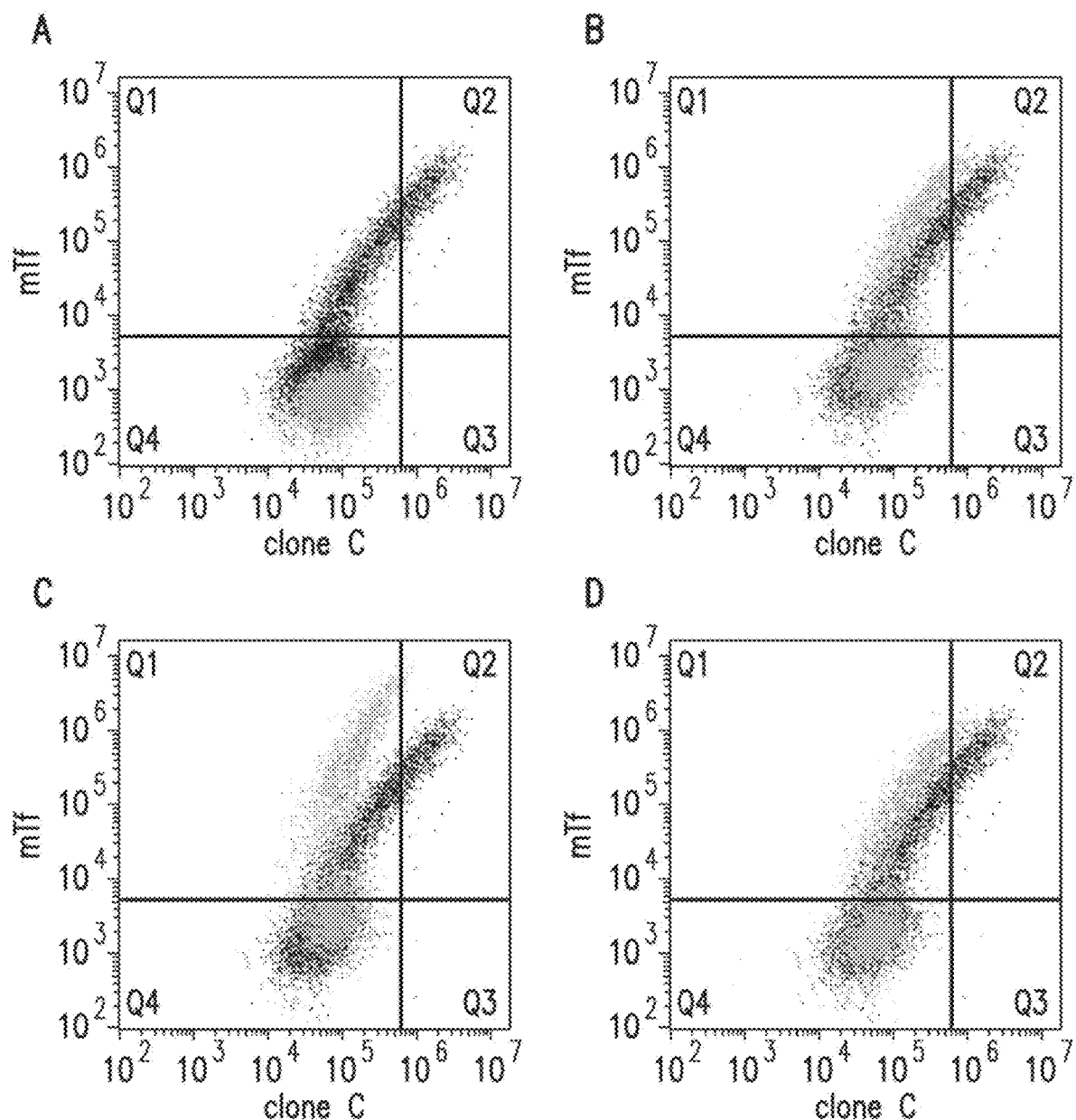
FIG. 21. Flow Cytometry Analysis of Clone C Alanine Mutants. Expi293™ cells were transiently transfected with 48 single mTfR-1 alanine mutants. The cells were co-stained with Clone C and mTf (as an expression control) and analyzed by FACS. Clone C positive cells are shown in grey and mTf positive cells in black. These plots show representative FACS staining of wildtype (WT) cells with (A) untransfected cells, (B) mutant N253A, (C) mutant G254A and (D) mutant S255A to illustrate a population shift from Q2 to Q1. Such a shift indicates reduced affinity of Clone C for a mutant relative to WT.

The flow cytometry results are shown in Table 9. Mutants I192A, N201A, F224A, L256A, A278T, L331A, I334A, V379A and N381A showed little or no expression based on mTf binding. These nine mutants showed no or low mTf binding, indicating that these mutants were poorly expressed and were not further analysed. Mutants that showed a reduction (to less than 75%) of the double-positive population compared to WT mTfR-1 are K191A against Clone C var. 18; P227A against Clone C var. 18; N253A against Clone C, Clone C var. 18, and Clone C var. 13; G254A against Clone C, Clone C var. 18, and Clone C var. 13; S255A against Clone C, Clone C var. 18, and Clone C var. 13; P324A against Clone C and Clone C var. 13; and S328A against Clone C var. 18 and Clone C var. 13. Mutation of the SK residues in mTfR-1 (residues 225-227) that corresponded to those in the human receptor (residues 223-225) had no effect on Clone C binding (Table 9), confirming that this putative epitope identified by chemical cross-linking is an area unlikely to interact with the CDR3. However, 3 mutants (N253A, G254, S255A) showed a consistent loss in binding to the original Clone C and two of its variants while retaining binding to control antibody 8D3 (FIG. 21 and Table 9), which in addition to mTf binding confirmed the structural integrity of the expressed mutants. This epitope, consisting of the residues NGS, represents a canonical N-glycosylation site (NXS/T) that is highly conserved in TfR-1 across different species (FIG. 22) and is consistent with the cross-species TfR-1 reactivity of Clone C (WO2018/031424).

TABLE 9

FACS Analysis of Clone C Binding to mTfR-1 Alanine Mutants

| Mutation | Clone C | Clone C v18 | Clone C v13 | 8D3 |
|---|---|---|---|---|
| WT | 100 | 100 | 100 | 100 |
| K191A | 51 | 25 | | 91 |
| I192A | 61 | 18 | | 13 |
| Q193A | 152 | 178 | | 63 |
| V194A | 184 | 199 | | 60 |
| K195A | 236 | 150 | | 63 |

TABLE 9-continued

FACS Analysis of Clone C Binding to mTfR-1 Alanine Mutants

| Mutation | Clone C | Clone C v18 | Clone C v13 | 8D3 |
|---|---|---|---|---|
| S196A | 123 | 104 | 47 | 74 |
| S197A | 111 | 66 | 56 | 100 |
| I198A | 239 | 79 | 73 | 94 |
| G199A | 72 | 42 | 36 | 69 |
| Q200A | 90 | 171 | 72 | 66 |
| N201A | 0 | 0 | 0 | 1 |
| M202A | 166 | 153 | 103 | 81 |
| F224A | 0 | 0 | 0 | 0 |
| S225A | 180 | 163 | 73 | 64 |
| K226A | 157 | 91 | 77 | 111 |
| P227A | 77 | 20 | 47 | 63 |
| T228A | 68 | 45 | 65 | 89 |
| E229A | 81 | 51 | 43 | 68 |
| V230A | 58 | 59 | 47 | 81 |
| S231A | 283 | 173 | 101 | 65 |
| N253A | 26 | 10 | 27 | 87 |
| G254A | 35 | 32 | 22 | 58 |
| S255A | 14 | 23 | 19 | 56 |
| L256A | 1 | 0 | 0 | 13 |
| Q274A | 182 | 229 | 84 | 87 |
| S275A | 97 | 136 | 54 | 70 |
| N277A | 137 | 155 | 84 | 56 |
| A278T | 25 | 21 | 12 | 45 |
| I279A | 177 | 206 | 85 | 74 |
| P324A | 27 | 39 | 25 | 39 |
| P325A | 148 | 175 | 83 | 119 |
| S326A | 136 | 129 | 77 | 31 |
| Q327A | 83 | 119 | 85 | 124 |
| S328A | 50 | 20 | 22 | 141 |
| S329A | 212 | 182 | 73 | 18 |
| G330A | 307 | 231 | 87 | 90 |
| L331A | 0 | 0 | 0 | 0 |
| P332A | 257 | 218 | 79 | 57 |
| N333A | 213 | 161 | 94 | 90 |
| I334A | 0 | 0 | 0 | 0 |
| P335A | 169 | 138 | 75 | 94 |
| I378A | 142 | 80 | 115 | 92 |
| V379A | 0 | 0 | 0 | 0 |
| K380A | 193 | 162 | 81 | 66 |
| N381A | 32 | 0 | 11 | 26 |
| V382A | 357 | 241 | 111 | 82 |
| L383A | 328 | 354 | 121 | 73 |
| K384A | 187 | 147 | 85 | 35 |

Figures 22, 23:
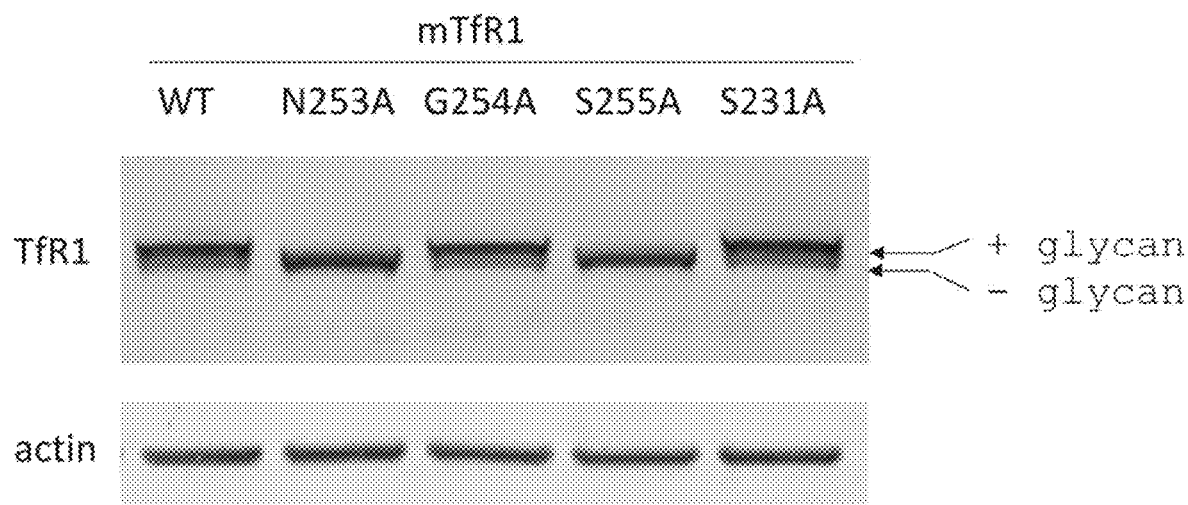
FIG. 22. TfR-1 Homology Alignment Surrounding the NGS epitope. A portion of the TfR-1 sequence surrounding the NGS site from human, mouse, rat, pig and rhesus macaque are aligned for comparison across multiple species (SEQ ID NOS 91-95, respectively, in order of appearance). Residues NGS identified as Clone C binding epitope are boxed and represent a conserved glycosylation site.
FIG. 23. Glycosylation of mTfR-1 Alanine Mutants. Alanine mutants of mTfR-1 were transiently expressed in Expi293 cells and lysed in RIPA buffer. Cell lysates were resolved on SDS-PAGE gel and analysed by Western blotting using anti-TfR-1 and anti-actin antibodies. The downward shift in the TfR-1 band in N253A and S255A mutants compared to WT or G254A and S231A indicates glycan loss.

The lysates from cells transfected with alanine mutants at residues NGS were further analysed by SDS-PAGE under reducing conditions followed by Western blotting using anti-TfR1 and anti-actin antibodies (FIG. 23). The shift on the blot relative to WT or a distant mutant not involved in binding (S231A) confirmed NGS as a glycosylation site of TfR-1 as previously reported (Lawrence et al. 1999). Mutants N253A and S255A lacked glycan attachment to the protein whereas G254A retained the glycan moiety. These results suggest that Clone C recognizes the protein itself rather than the glycan since binding was disrupted regardless of the glycosylation state. Nevertheless, it cannot be excluded that the glycan may play a role in retaining the native structure of TfR-1 and indirectly contribute to the Clone C-hTfR-1 binding interaction.

Additionally, the data indicate that the epitope recognized by Clone C is structural rather than linear because of the specificity of Clone C for TfR-1 over numerous proteins in the proteome with canonical N-linked glycosylation sites. Further, the NGS epitope and SK cross-linked region were calculated to be ~14-20 Å apart (FIG. 24), which overlaps with the distance between the CDR3 and the cross-linked T107 (FIG. 19) that was at the range of 18-24 Å (based on VNAR structure PDB: 2I25; (Stanfield et al. 2007). Hence, the combined chemical cross-linking and alanine scanning data not only defines the epitope but also indicates that Clone C binds in a particular orientation on hTfR-1.

Figure 24:
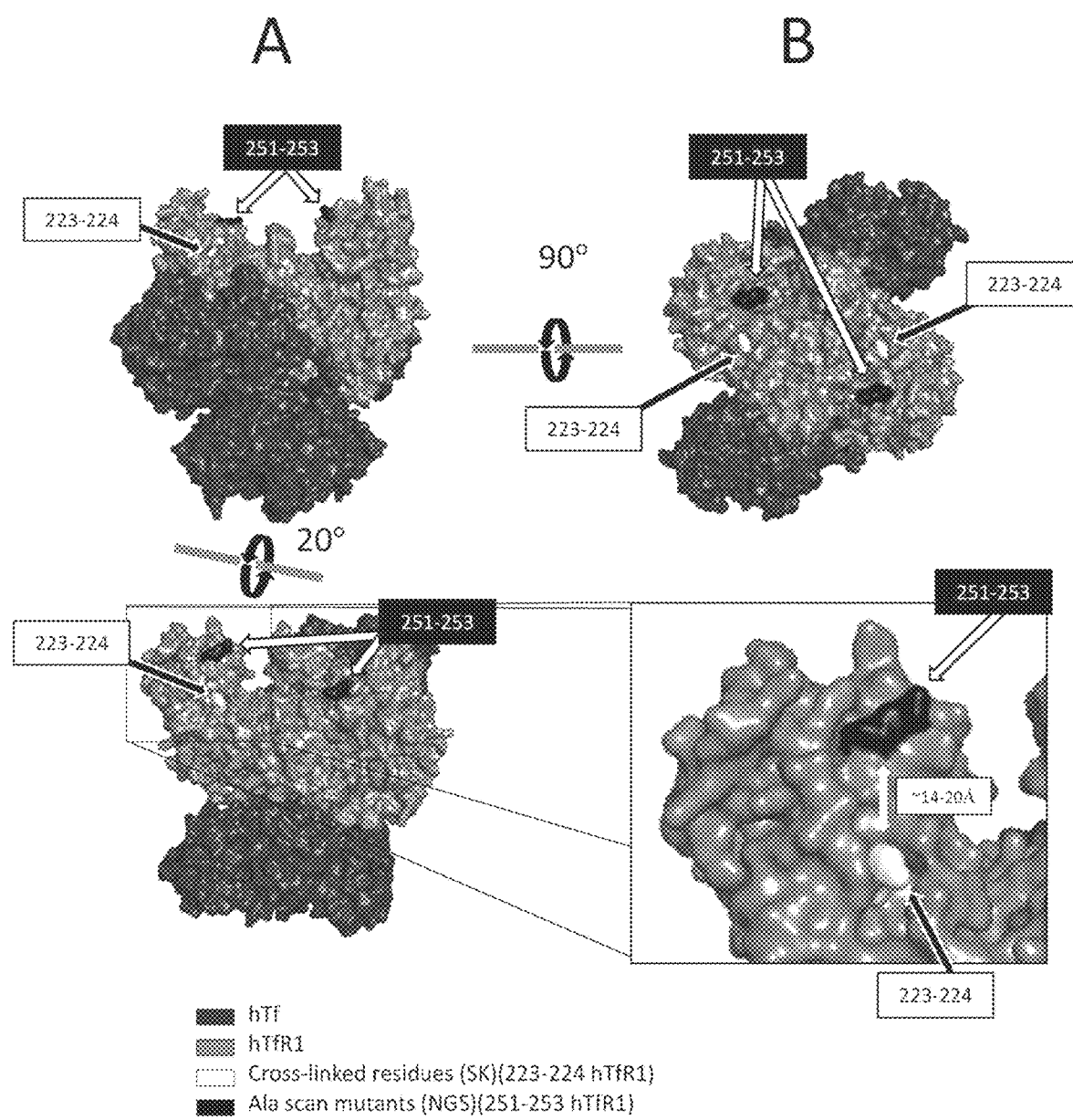
FIG. 24. Structural Model of hTfR-1 Showing the Clone C Epitope. Side (A) and top (B) views of the dimeric human TfR-1/transferrin complex (PDB: 1SUV) space filling model is shown with the NGS residues (251-253) depicted in black. SK residues (223-224) identified by cross-linking are depicted in white. The approximate the distance between these two regions, measured using PyMOL, is in the range of 14-20 Å, depending on the residue and atom used for the measurement.

By comparison, the 8D3 antibody only binds to mouse TfR-1 (not to human TfR-WO1) and its epitope has been mapped to the sequence QSNGNL (SEQ ID NO. 72) at the tip of the apical domain (WO2014/033074); Niewoehner et al. 2014). This region of TfR1 shows poor homology between species and is under selective mutational pressure by viruses that use this receptor to gain cellular entry (Demogines et al. 2013), which helps explain the species specificity of most monoclonal antibodies to the receptor. In contrast, the 253-255 glycosylation site recognized by Clone C while naturally surface exposed, lies deeper within the structure of the receptor (FIG. 24). Again, these results are consistent with the binding properties of single domain VNARs which have been shown to access cryptic epitopes inaccessible to monoclonal antibodies (Stanfield et al. 2004) and may explain the relative high frequency of obtaining species cross-reactive VNAR antibodies to multiple non-competing epitopes (WO2016/077840, TfR binding compounds).

Example 8. Confirmation of the NGS Glycosylation Site as the Clone C Epitope

Three mTfR1 mutants M1 (AGS), M2 (NAS) and M3 (NGA) were transiently transfected using an Expi293 expression system as described above. M1 (AGS) is the same mutant as N253A, M2 (NAS) is the same as G254A and M3 (NGA) is the same as S255A in FIG. 7.

Cell cultures from the mutants were centrifuged at 4,600 g for 10 minutes at room temperature, the supernatants were passed through 0.45 μm syringe filters and the eluate loaded onto 1 ml HisTrap™ Excel (GE Healthcare) columns at a 2 ml/min flow rate. The columns were washed with 20 volumes of buffer containing 20 mM phosphate buffer pH 7.4, 300 mM NaCl and the proteins eluted with a 10-volume gradient with buffer containing 500 mM imidazole. Selected fractions were concentrated using 30,000-50,000 1\4W concentrators (Amicon) followed by buffer exchange to PBS pH 7.4 using HiTrap™ Desalting Sephadex G-25 columns (GE Healthcare).

Figure 25:
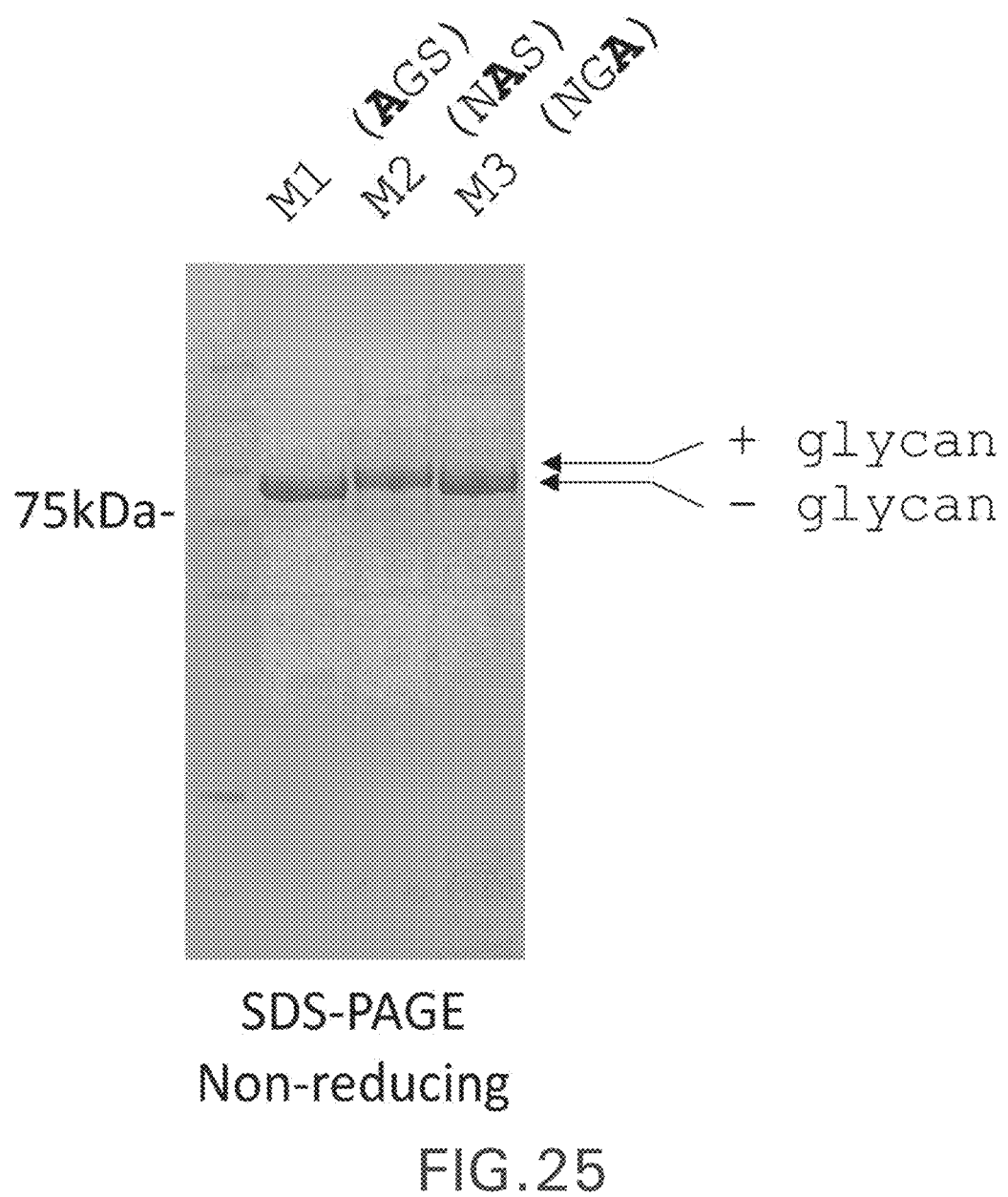
FIG. 25. Purification of mTfR-1 Alanine Mutants. Three mTfR-1 mutants M1 (AGS), M2 (NAS) and M3 (NGA) were purified and analysed by SDS-PAGE. The mutants M1 and M3 migrate faster compared to M2, indicative of lower mass due to the lack of glycan.

The purified mutants M1, M2 and M3 were analysed by non-reducing SDS-PAGE and the stained gel indicates that only M2 (NAS) was glycosylated as shown by the size shift of the migrating protein (FIG. 25) and in the Western blot using transfected cell lysates (FIG. 7).

The biochemical EC50 (equilibrium constant, the concentration at which the ratio of bound to unbound is 50:50) of Clone C-hFc to the 3 purified alanine mutant receptors was determined by ELISA. Serial dilutions the VNAR-Fc fusion protein in blocking buffer (PBS-0.1% Tween+2.5% milk) were exposed to pre-blocked Nunc Maxisorp 96-well plates coated with the M1, M2 and M3 mutants at 1 μg/mL. After washing in PBS-0.1% Tween-20, binding of Clone C-hFc fusion was detected using an anti-human IgG (Fc specific) peroxidase antibody (Sigma-Aldrich) and the plates were developed using the chromogenic substrate TMB. Absorbance at 450 nm was recorded using an Envision multi-well reader (Perkin Elmer) and EC50s were calculated by fitting curves (non-linear regression) using GraphPad Prism®.

Figure 26:
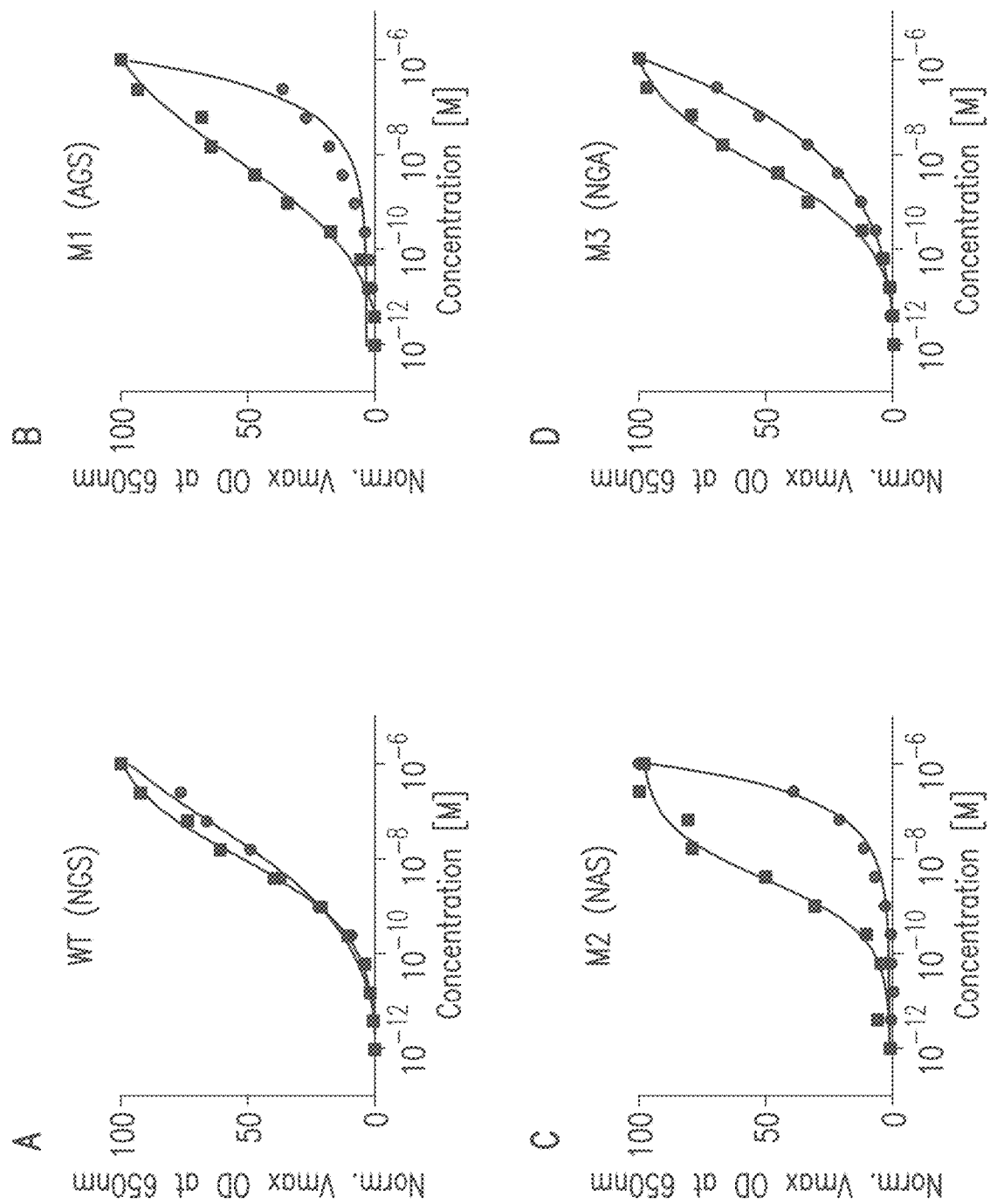
FIG. 26. Binding Analysis of Clone C to mTfR-1 Alanine Mutants. ELISA plates were coated with (A) WT mTfR-1, (B) alanine mutant M1 (AGS), (C) alanine mutant M2 (NAS), or (D) alanine mutant M3 (NGA) and incubated with serial dilutions of Clone C, formatted as an hFc fusion, (solid circles) or control 8D3 antibodies (solid boxes). Since Clone C binding to the alanine mutants did not reach saturation, EC50 values could not be calculated.

The binding of Clone C compared to the 8D3 antibody was tested on purified WT mTfR1 in addition to the three mutants by ELISA (FIG. 26). EC50s were calculated at 65.4 nM and 11.1 nM for Clone C and 8D3, respectively. The binding of Clone C was significantly reduced for M1, M2 and M3 mutants of mTfR-1 compared to the WT receptor, whereas 8D3 retained similar binding to all 3 mutants. These results confirm that the Clone C epitope on TfR-1 is the NGS glycosylation site.

Figure 27:
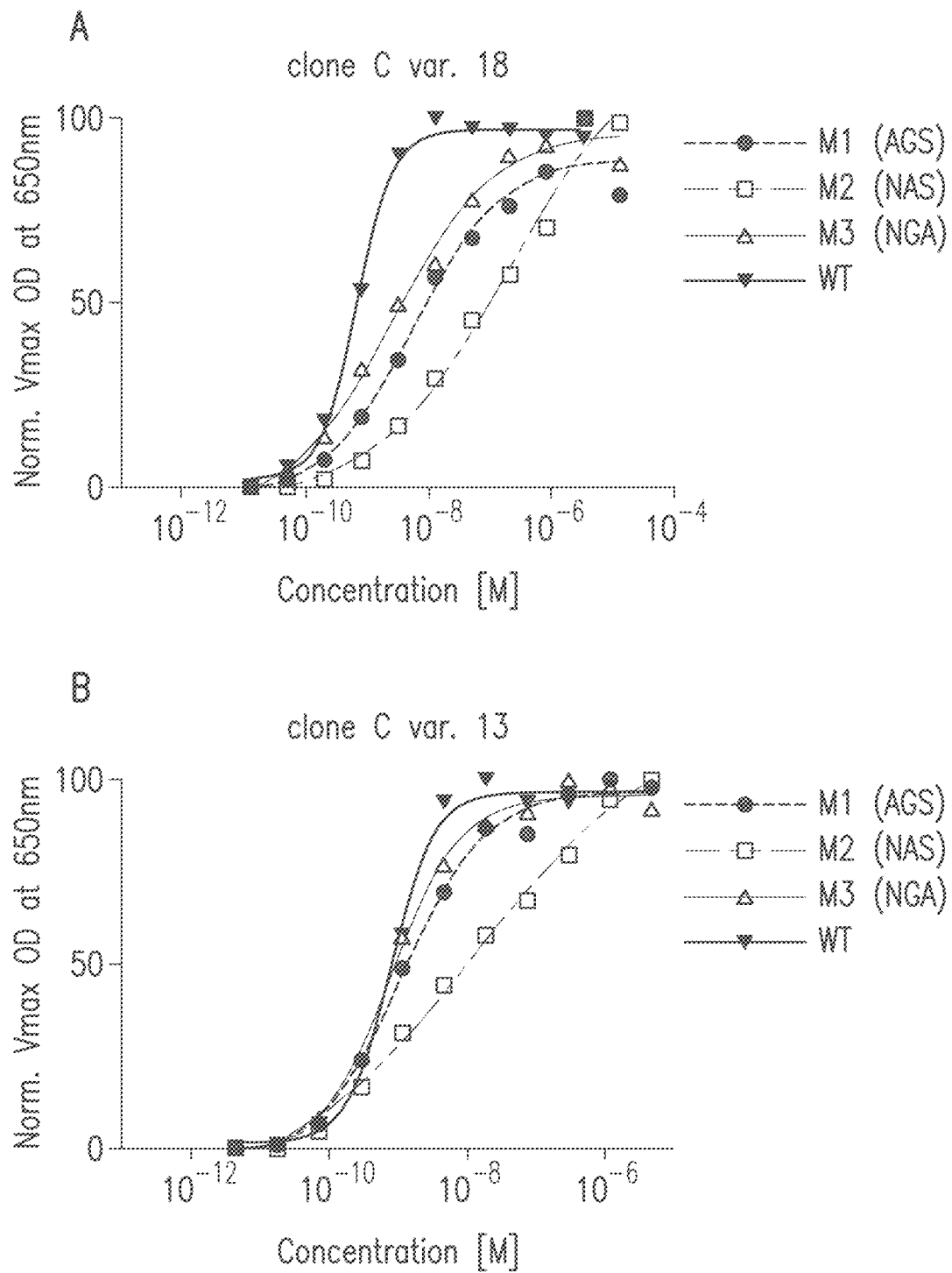
FIG. 27. Binding Analysis of Clone C Variants to mTfR-1 Alanine Mutants. ELISA plates were coated with WT mTfR-1, alanine mutant M1 (AGS), alanine mutant M2 (NAS), or alanine mutant M3 (NGA) and incubated with serial dilutions of (A) Clone C variant 18 or (B) Clone C variant 13 (Table 1). The variants were formatted as VNAR-hFc fusions.
Figure 28:
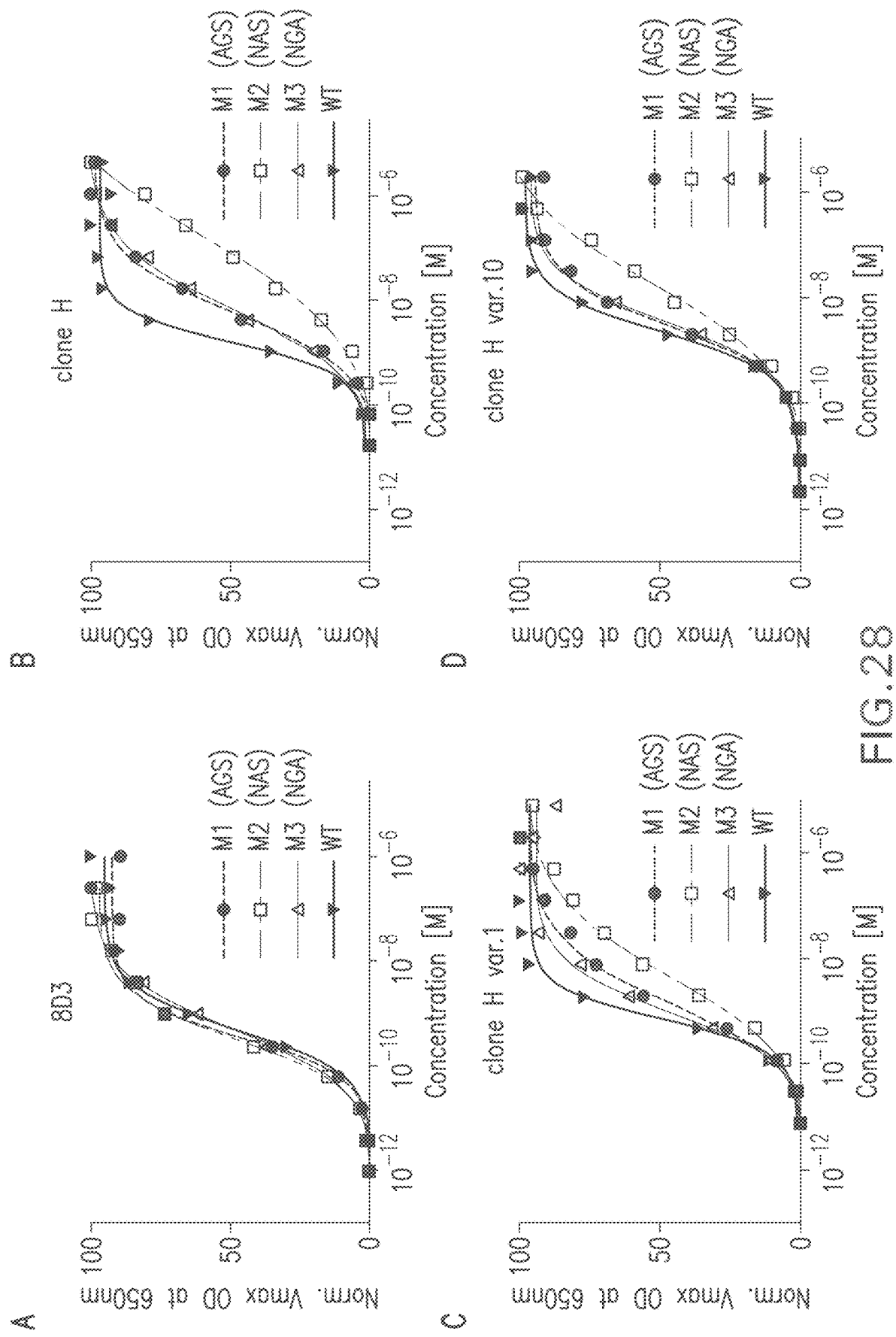
FIG. 28. Binding Analysis of Clone H and Its Variants to mTfR-1 alanine Mutants. ELISA plates were coated with WT mTfR-1, alanine mutant M1 (AGS), alanine mutant M2 (NAS), or alanine mutant M3 (NGA) and incubated with serial dilutions of (A) 8D3 antibody as a control for structural integrity and affinity, (B) Clone H, (C) Clone H variant 1, and (D) Clone H variant 10 (see Table 6 for the variants). Clone H and its variants were formatted as VNAR-hFc fusions.

Two Clone C variants (var.18: CRD3 sequence VQYPQYPNYFW and var. 13: CRD3 sequence VQYPQQDNYFW; see Table 1; SEQ ID NOS. 31 and 26, respectively) also showed reduced binding to the mutants relative to WT (FIG. 27), further supporting that the Clone C epitope is the NGS glycosylation site. The EC50 values for the Clone C variants on the mutants were calculated in GraphPad Prism using serial dilutions of two Clone C variants as VNAR-hFcs (Table 10).

TABLE 10

| | EC50[M] | | | |
|---|---|---|---|---|
| | M1 (AGS) | M2 (NAS) | M3 (NGA) | WT |
| clone C var. 18 | 5.9E−09 | 2.0E−07 | 2.6E−09 | 6.9E−10 |
| clone C var. 13 | 1.1E−09 | 1.3E−08 | 7.9E−10 | 8.0E−10 |

Given the similarity between the paratopes of Clone C and Clone H (FIG. 13), these clones were analyzed for the ability to block each other's binding to mouse or human TfR-1 in a cross-competition ELISA (Table 11), indicating that that the two clones a share a similar or overlapping binding site. VNAR-Fc fusion proteins were tested for cross-blocking in a pairwise manner against mouse and human TfR-1 immobilized on biosensors (Octet®, Fortebio). $1^{st}$ and $2^{nd}$ indicates the temporal sequence of antibody binding. Black indicates competition for binding (signal less than half of maximum when measured against buffer), white indicates the lack of competition.

TABLE 11

| | 2nd | | |
|---|---|---|---|
| 1st | clone c | clone H | buffer |
| hTfR1 | | | |
| clone C | 0.1288 | 0.2256 | 0.0106 |
| clone H | 0.5695 | 0.2813 | −0.2664 |
| buffer | 8.3466 | 7.3174 | 0.2004 |
| mTfR1 | | | |
| clone C | 0.3726 | 0.5113 | 0.267 |
| clone H | 0.3466 | 0.2767 | 0.0139 |
| buffer | 3.6495 | 2.6355 | 1.4098 |

To assess the Clone H epitope, binding to mTfR-1 alanine mutants was also tested (FIG. 28). The 8D3 control antibody bound with similar affinity to WT and the three mTfR-1 ala mutants (NGS), confirming the structural integrity of the receptor mutants. Moreover, the binding of Clone H and two of its variants (variant 1: CDR3 sequence VQWPSSSN-GRYW and variant 10: CDR3 sequence QQFPSWFN-GRYW; see Table 4; SEQ ID NOS. 55 and 64, respectively) to the mutants was specifically reduced relative to WT, evidence that Clone C and Clone H interact with the same NGS epitope in TfR-1. Binding was most affected to the M2 (NAS) mutant where a similar 10-fold reduction was likewise observed for the Clone C variants (FIG. 27).

EC50 values were calculated in GraphPad Prism using serial dilutions of Clone H and two variants (Table 12).

TABLE 12

| | EC50[M] | | | |
|---|---|---|---|---|
| | M1 (AGS) | M2 (NAS) | M3 (NGA) | WT |
| 8D3 | 3.5E−10 | 3.3E−10 | 5.1E−10 | 4.9E−10 |
| clone H | 5.7E−09 | 1.7E−07 | 6.6E−09 | 1.6E−09 |
| clone H var. 1 | 1.4E−09 | 4.7E−09 | 9.9E−10 | 6.9E−10 |
| clone H var. 10 | 3.3E−09 | 2.2E−08 | 4.0E−09 | 2.5E−09 |

REFERENCES

Alata, W., S. Paris-Robidas, V. Emond, F. Bourasset and F. Calon (2014). "Brain uptake of a fluorescent vector targeting the transferrin receptor: a novel application of in situ brain perfusion." *Mol Pharm* 11(1): 243-253.

Arap, W., R. Pasqualini and E. Ruoslahti (1998). "Cancer treatment by targeted drug delivery to tumor vasculature in a mouse model." *Science* 279(5349): 377-380.

Armour, K. L., M. R. Clark, A. G. Hadley and L. M. Williamson (1999). "Recombinant human IgG molecules lacking Fcgamma receptor I binding and monocyte triggering activities." Eur J Immunol 29(8): 2613-2624.

Bich, C., S. Maedler, K. Chiesa, F. DeGiacomo, N. Bogliotti and R. Zenobi (2010). "Reactivity and applications of new amine reactive cross-linkers for mass spectrometric detection of protein-protein complexes." Anal Chem 82(1): 172-179.

Bien-Ly, N., Y. J. Yu, D. Bumbaca, J. Elstrott, C. A. Boswell, Y. Zhang, W. Luk, Y. Lu, M. S. Dennis, R. M. Weimer, I. Chung and R. J. Watts (2014). "Transferrin receptor (TfR) trafficking determines brain uptake of TfR antibody affinity variants." J Exp Med 211(2): 233-244.

Boje, K. M. (1996). "Inhibition of nitric oxide synthase attenuates blood-brain barrier disruption during experimental meningitis." *Brain Res* 720(1-2): 75-83.

Branston, S., E. Stanley, E. Keshavarz-Moore and J. Ward (2012). "Precipitation of filamentous bacteriophages for their selective recovery in primary purification." *Biotechnol Prog* 28(1): 129-136.

Cheng, Y., O. Zak, P. Aisen, S. C. Harrison and T. Walz (2004). "Structure of the human transferrin receptor-transferrin complex." Cell 116(4): 565-576.

Couch, J. A., Y. J. Yu, Y. Zhang, J. M. Tarrant, R. N. Fuji, W. J. Meilandt, H. Solanoy, R. K. Tong, K. Hoyte, W. Luk, Y. Lu, K. Gadkar, S. Prabhu, B. A. Ordonia, Q. Nguyen, Y. Lin, Z. Lin, M. Balazs, K. Scearce-Levie, J. A. Ernst, M. S. Dennis and R. J. Watts (2013). "Addressing safety liabilities of TfR bispecific antibodies that cross the blood-brain barrier." *Sci Transl Med* 5(183): 183ra157, 181-112.

Demeule, M., N. Beaudet, A. Regina, E. Besserer-Offroy, A. Murza, P. Tetreault, K. Belleville, C. Che, A. Larocque, C. Thiot, R. Beliveau, J. M. Longpre, E. Marsault, R. Leduc, J. E. Lachowicz, S. L. Gonias, J. P. Castaigne and P. Sarret (2014). "Conjugation of a brain-penetrant peptide with neurotensin provides antinociceptive properties." *J Clin Invest* 124(3): 1199-1213.

Demogines A, Abraham J, Choe H, Farzan M, Sawyer S L (2013) "Dual host-virus arms races shape an essential housekeeping protein" PLoS Biol. 11(5):e1001571.

de Vries, H. E., M. C. Blom-Roosemalen, A. G. de Boer, T. J. van Berkel, D. D. Breimer and J. Kuiper (1996). "Effect of endotoxin on permeability of bovine cerebral endothelial cell layers in vitro." *J Pharmacol Exp Ther* 277(3): 1418-1423.

Griffiths, A. D., S. C. Williams, O. Hartley, I. M. Tomlinson, P. Waterhouse, W. L. Crosby, R. E. Kontermann, P. T. Jones, N. M. Low, T. J. Allison and et al. (1994). "Isolation of high affinity human antibodies directly from large synthetic repertoires." *EMBO J* 13(14): 3245-3260.

Hasler, J., M. F. Flajnik, G. Williams, F. S. Walsh and J. L. Rutkowski (2016). "VNAR single-domain antibodies specific for BAFF inhibit B cell development by molecular mimicry." *Mol Immunol* 75: 28-37.

Lawrence C M, Ray S, Babyonyshev M, Galluser R, Borhani D W, et al. Crystal structure of the ectodomain of human transferrin receptor. Science. 1999 Oct. 22; 286 (5440):779-82.

Liu, S., R. Tobias, S. McClure, G. Styba, Q. Shi and G. Jackowski (1997). "Removal of endotoxin from recombinant protein preparations." *Clin Biochem* 30(6): 455-463.

Mayhan, W. G. (1998). "Effect of lipopolysaccharide on the permeability and reactivity of the cerebral microcirculation: role of inducible nitric oxide synthase." *Brain Res* 792(2): 353-357.

Moos, T. and E. H. Morgan (2001). "Restricted transport of anti-transferrin receptor antibody (OX26) through the blood-brain barrier in the rat." *J Neurochem* 79(1): 119-129.

Niewoehner J, Bohrmann B, Collin L, Urich E, Sade H, et al. (2014) "Increased brain penetration and potency of a therapeutic antibody using a monovalent molecular shuttle." Neuron. 81(1):49-60.

Pasqualini, R. and E. Ruoslahti (1996). "Organ targeting in vivo using phage display peptide libraries." *Nature* 380 (6572): 364-366.

Shields, R. L., A. K. Namenuk, K. Hong, Y. G. Meng, J. Rae, J. Briggs, D. Xie, J. Lai, A. Stadlen, B. Li, J. A. Fox and L. G. Presta (2001). "High resolution mapping of the binding site on human IgG1 for Fc gamma RI, Fc gamma RII, Fc gamma RIII, and FcRn and design of IgG1 variants with improved binding to the Fc gamma R." *J Biol Chem* 276(9): 6591-6604.

Shukla, A., M. Dikshit and R. C. Srimal (1995). "Nitric oxide modulates blood-brain barrier permeability during infections with an inactivated bacterium." *Neuroreport* 6(12): 1629-1632.

Stanfield, R. L., H. Dooley, P. Verdino, M. F. Flajnik and I. A. Wilson (2007). "Maturation of shark single-domain (IgNAR) antibodies: evidence for induced-fit binding." J Mol Biol 367(2): 358-372.

Stanfield R L, Dooley H, Flajnik M F, Wilson I A. (2004) "Crystal structure of a shark single-domain antibody V region in complex with lysozyme." Science 305(5691): 1770-1773.

Triguero, D., J. Buciak and W. M. Pardridge (1990). "Capillary depletion method for quantification of blood-brain barrier transport of circulating peptides and plasma proteins." *J Neurochem* 54(6): 1882-1888.

Williams, S. K., J. F. Gillis, M. A. Matthewst, R. C. Wagnert and M. W. Bitensky (1980). "Isolation and Characterization of Brain Endothelial Cells: Morphology and Enzyme Activity." *Journal of Neurochemistry* 35(2): 374-381.

Yu, Y. J., Y. Zhang, M. Kenrick, K. Hoyte, W. Luk, Y. Lu, J. Atwal, J. M. Elliott, S. Prabhu, R. J. Watts and M. S. Dennis (2011). "Boosting brain uptake of a therapeutic antibody by reducing its affinity for a transcytosis target." *Sci Transl Med* 3(84): 84ra44.

We claim:

1. A TfR-specific binding moiety comprising a Type II VNAR scaffold represented by the formula, from N to C terminus,

FW1-CDR1-FW2-HV2-FW2'-HV4-FW3-CDR3-FW4, wherein the CDR1 region consists of a peptide having an amino acid sequence of formula DSNCALS (SEQ ID NO. 2) or DSNCELS (SEQ ID NO. 7), wherein the CDR3 region consists of a peptide having an amino acid sequence selected from any one of SEQ ID NOS. 14-51 when CDR1 is DSNCALS, or selected from any one of SEQ ID NOS. 55-64 when CDR1 is DSNCELS, wherein said moiety is capable of specifically binding to human TfR-1 without substantially interfering with transferrin binding to and/or transport by human TfR-1, and is capable of crossing the blood brain barrier, with the proviso that the VNAR scaffold does not have an amino acid sequence of (Clone C; SEQ ID NO. 1)
ARVDQTPQTITKETGESLTINCVLRDSNCALSSTYWYRKKSGSTNEENIS

KGGRYVETVNSGSKSFSLRINDLTVEDSGTYRCNVVQYPSYNNYFWCDVY

GDGTAVTVN or (Clone H; SEQ ID NO. 6)
ARVDQTPQTITKETGESLTINCVLRDSNCELSSTYWYRKKSGSTNEESIS

KGGRYVETVNSGSKSFSLRINDLVVEDSGTYRCNVQQFPSSSNGRYWCDV

YGGGTAVTVNA.

2. The TfR-specific binding moiety of claim 1, wherein FW1-CDR1-FW2-HV2-FW2'-HV4-FW3 has a sequence of (SEQ ID NO. 4)
ARVDQTPQTITKETGESLTINCVLRDSNCALSSTYWYRKKSGSTNEENIS

KGGRYVETVNSGSKSFSLRINDLTVEDSGTYRCNV,

FW4 has a sequence of YGDGTAVTVN (SEQ ID NO. 5); or
wherein
FW1-CDR1-FW2-HV2-FW2'-HV4-FW3 and FW4, in combination, has a sequence which is at least 95% identical to SEQ. ID NOS. 4 and 5, provided that CDR1 is unchanged.

3. The TfR-specific binding moiety of claim 1, wherein FW1-CDR1-FW2-HV2-FW2'-HV4-FW3 has a sequence of (SEQ ID NO. 9)
ARVDQTPQTITKETGESLTINCVLRDSNCELSSTYWYRKKSGSTNEESIS

KGGRYVETVNSGSKSFSLRINDLVVEDSGTYRCNV,

FW4 has a sequence of YGGGTAVTVNA (SEQ ID NO. 10); or
wherein
FW1-CDR1-FW2-HV2-FW2'-HV4-FW3 and FW4, in combination, has a sequence which is at least 95% identical to SEQ. ID NOS. 9 and 10, provided that CDR1 is unchanged.

4. The TfR-specific binding moiety of claim 1, wherein said moiety, when formatted as an Fc fusion protein and injected into mice at 1.875 mg/kg, exhibits a concentration in murine brain homogenates of at least about 0.8 nM.

5. The TfR-specific binding moiety of claim 1, wherein said moiety has an affinity constant (KD) for human TfR-1 less than or equal to 50 nM.

6. The TfR-specific binding moiety of claim 1, wherein said moiety has an affinity constant (KD) for human TfR-1 of 200 pM to 3 nM.

7. A conjugate comprising the TfR-specific binding moiety of claim 1 operably linked to a heterologous diagnostic or therapeutic agent.

8. A kit for detecting or quantifying TfR-1 in a sample which comprises at least one TfR-specific binding moiety of claim 1 or a conjugate thereof.

9. A pharmaceutical composition comprising a TfR-specific binding moiety of claim 1 or a conjugate thereof.

10. A nucleic acid encoding the TfR-specific binding moiety of claim 1 or a conjugate thereof, wherein said conjugate is a fusion protein with a heterologous diagnostic or therapeutic agent operably linked to said moiety.

11. A vector comprising a nucleic acid of claim 10.

12. A host cell comprising a vector of claim 11.

13. A method of delivering a diagnostic or therapeutic agent across a cell membrane in a subject, which comprises administering a diagnostic or therapeutic agent operably linked to a TfR-specific binding moiety of claim 1, wherein said TfR-specific binding moiety is endocytosed to thereby deliver said diagnostic or therapeutic agent across the cell membrane.

14. A method of delivering a therapeutic or diagnostic molecule across the blood brain barrier or to the gastrointestinal (GI) tract which comprises administering a TfR-specific binding moiety of claim 1 to a subject for a time and in an amount effective to treat or diagnose a CNS disease or condition or a GI disease or condition, said therapeutic or diagnostic molecule being operably conjugated to said moiety.

15. A method of identifying, quantifying or localizing a TfR-containing biological sample or cell which comprises contacting a test sample in vitro or in vivo with any one of the TfR-specific binding moieties of claim 1, and directly or indirectly measuring the TfR-specific binding in or to said sample.

16. A method of targeting delivery of a heterologous molecule to a TfR-expressing cell which comprises delivering a TfR-specific conjugate of claim 7 to said target.

* * * * *

SEQUENCE LISTING

```
<160> NUMBER OF SEQ ID NOS: 95

<210> SEQ ID NO 1
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Val Gln Tyr Pro Ser Tyr Asn Asn Tyr Phe Trp
                85                  90                  95

Cys Asp Val Tyr Gly Asp Gly Thr Ala Val Thr Val Asn
            100                 105

<210> SEQ ID NO 2
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 2

Asp Ser Asn Cys Ala Leu Ser
1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Gln Tyr Pro Ser Tyr Asn Asn Tyr Phe Trp Cys Asp Val
1               5                   10

<210> SEQ ID NO 4
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val
                85

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Gly Asp Gly Thr Ala Val Thr Val Asn
1               5                   10

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Arg Val Asp Gln Thr Pro Gln Thr Ile Thr Lys Glu Thr Gly Glu

```
                    1               5                  10                  15
Ser Leu Thr Ile Asn Cys Val Leu Arg Asp Ser Asn Cys Glu Leu Ser
            20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
            50                  55                  60

Ser Phe Ser Leu Arg Ile Asn Asp Leu Val Val Glu Asp Ser Gly Thr
65                  70                  75                  80

Tyr Arg Cys Asn Val Gln Gln Phe Pro Ser Ser Ser Asn Gly Arg Tyr
                85                  90                  95

Trp Cys Asp Val Tyr Gly Gly Gly Thr Ala Val Thr Val Asn Ala
                100                 105                 110

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ser Asn Cys Glu Leu Ser
1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Phe Pro Ser Ser Ser Asn Gly Arg Tyr Trp Cys Asp Val
1               5                   10                  15

<210> SEQ ID NO 9
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
            50                  55                  60

Ser Phe Ser Leu Arg Ile Asn Asp Leu Val Val Glu Asp Ser Gly Thr
65                  70                  75                  80

Tyr Arg Cys Asn Val
                85

<210> SEQ ID NO 10
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Gly Gly Gly Thr Ala Val Thr Val Asn Ala
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Leu, Gln or Val
<220> FEATURE:
<221> NAME/KEY: MOD_RES
<222> LOCATION: (3)..(3)
<223> OTHER INFORMATION: Phe, His, Arg, Ser, Trp or Tyr
<220> FEATURE:
<221> NAME/KEY: MOD_RES
<222> LOCATION: (5)..(5)
<223> OTHER INFORMATION: Phe, His, Asn, Gln, Arg, Ser, Thr or Val
<220> FEATURE:
<221> NAME/KEY: MOD_RES
<222> LOCATION: (6)..(6)
<223> OTHER INFORMATION: His, Ile, Leu, Asn, Pro, Gln, Arg, Ser, Thr,
      Trp or Tyr
<220> FEATURE:
<221> NAME/KEY: MOD_RES
<222> LOCATION: (7)..(7)
<223> OTHER INFORMATION: Asp, Glu, Phe, Gly, His, Asn, Pro, Gln, Arg,
      Ser, Thr or Trp
<220> FEATURE:
<221> NAME/KEY: MOD_RES
<222> LOCATION: (8)..(8)
<223> OTHER INFORMATION: His, Asn, Pro, Arg or Ser
<220> FEATURE:
<221> NAME/KEY: MOD_RES
<222> LOCATION: (9)..(9)
<223> OTHER INFORMATION: Ala, Phe, Gly, His, Leu, Pro or Tyr
<220> FEATURE:
<221> NAME/KEY: MOD_RES
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: Phe or Tyr

<400> SEQUENCE: 11

Xaa Gln Xaa Pro Xaa Xaa Xaa Xaa Xaa Arg Xaa Trp Cys Asp Val
1               5                   10                  15

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Gln Tyr Pro
1
```

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Tyr Asn Asn Tyr
1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Gln Arg Pro Ser Tyr Asn Asn Tyr Phe Trp Cys Asp Val
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Gln Arg Pro Ser Tyr Asn Asn Tyr Phe Trp Cys Asp Val
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Gln His Pro Ser Tyr Asn Asn Tyr Phe Trp Cys Asp Val
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Gln Arg Pro Ser Tyr Asn Asn Tyr Phe Trp Cys Asp Val
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

Val Gln Ser Pro Ser Tyr Asn Asn Tyr Phe Trp Cys Asp Val
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Gln Trp Pro Ser Ile Gln Ser Pro Phe Trp Cys Asp Val
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Gln Trp Pro Ser Leu Ser Ser Pro Phe Trp Cys Asp Val
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Gln Trp Pro Ser Tyr Asn Asn Tyr Phe Trp Cys Asp Val
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Gln Trp Pro Thr Leu Ser Ser Pro Phe Trp Cys Asp Val
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Gln Tyr Pro Phe Leu Glu Asn Tyr Phe Trp Cys Asp Val
1               5                   10

<210> SEQ ID NO 24
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 24

Val Gln Tyr Pro His Tyr Asn Asn Tyr Phe Trp Cys Asp Val
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Gln Tyr Pro Gln Gln Asp Asn Pro Phe Trp Cys Asp Val
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Gln Tyr Pro Gln Gln Asp Asn Tyr Phe Trp Cys Asp Val
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Gln Tyr Pro Gln Gln Asp Arg Pro Phe Trp Cys Asp Val
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Gln Tyr Pro Gln Gln Pro Asn Tyr Phe Trp Cys Asp Val
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Gln Tyr Pro Gln Gln Thr Arg Pro Phe Trp Cys Asp Val
1               5                   10
```

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Gln Tyr Pro Gln Tyr Asp Asn Tyr Phe Trp Cys Asp Val
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Gln Tyr Pro Gln Tyr Pro Asn Tyr Phe Trp Cys Asp Val
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Gln Tyr Pro Arg Thr Asn Asn Tyr Phe Trp Cys Asp Val
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Gln Tyr Pro Ser His Asn Asn Tyr Phe Trp Cys Asp Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Gln Tyr Pro Ser Ile Phe Asn Tyr Phe Trp Cys Asp Val
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 35

Val Gln Tyr Pro Ser Asn Asn Asn Tyr Phe Trp Cys Asp Val
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Gln Tyr Pro Ser Gln Gln Asn Tyr Phe Trp Cys Asp Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Gln Tyr Pro Ser Trp Asp Asn Tyr Phe Trp Cys Asp Val
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Gln Tyr Pro Ser Tyr Asp Asn Pro Phe Trp Cys Asp Val
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Gln Tyr Pro Ser Tyr Asp Arg Pro Phe Trp Cys Asp Val
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Gln Tyr Pro Ser Tyr His Asn Tyr Phe Trp Cys Asp Val
1               5                   10

<210> SEQ ID NO 41
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 41

Val Gln Tyr Pro Ser Tyr Asn His Tyr Phe Trp Cys Asp Val
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Gln Tyr Pro Ser Tyr Asn Asn His Phe Trp Cys Asp Val
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Gln Tyr Pro Ser Tyr Asn Asn Leu Tyr Trp Cys Asp Val
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Gln Tyr Pro Ser Tyr Arg Ser Leu Phe Trp Cys Asp Val
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Gln Tyr Pro Ser Tyr Thr Arg Ala Phe Trp Cys Asp Val
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Gln Tyr Pro Ser Tyr Thr Arg Pro Phe Trp Cys Asp Val
1               5                   10
```

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Gln Tyr Pro Thr Asn Glu Asn Tyr Phe Trp Cys Asp Val
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Gln Tyr Pro Val Gln Asp Asn Tyr Phe Trp Cys Asp Val
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Gln Tyr Pro Val Gln Pro Asn Tyr Phe Trp Cys Asp Val
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Gln Tyr Pro Val Tyr Asp Asn Tyr Phe Trp Cys Asp Val
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Gln Tyr Pro Val Tyr Pro Asn Tyr Phe Trp Cys Asp Val
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Val, Ala or Leu
<220> FEATURE:
<221> NAME/KEY: MOD_RES
<222> LOCATION: (3)..(3)
<223> OTHER INFORMATION: Tyr, His, Arg, Ser or Trp
<220> FEATURE:
<221> NAME/KEY: MOD_RES
<222> LOCATION: (5)..(5)
<223> OTHER INFORMATION: Ser, Phe, His, Gln, Arg, Ser, Thr or Val
<220> FEATURE:
<221> NAME/KEY: MOD_RES
<222> LOCATION: (6)..(6)
<223> OTHER INFORMATION: Tyr, His, Ile, Leu, Asn, Gln, Thr or Trp
<220> FEATURE:
<221> NAME/KEY: MOD_RES
<222> LOCATION: (7)..(7)
<223> OTHER INFORMATION: Asn, Asp, Glu, Phe, His, Pro, Gln, Arg, Ser or
      Thr
<220> FEATURE:
<221> NAME/KEY: MOD_RES
<222> LOCATION: (8)..(8)
<223> OTHER INFORMATION: Asn, His, Arg or Ser
<220> FEATURE:
<221> NAME/KEY: MOD_RES
<222> LOCATION: (9)..(9)
<223> OTHER INFORMATION: Tyr, Ala, His, Leu or Pro
<220> FEATURE:
<221> NAME/KEY: MOD_RES
<222> LOCATION: (10)..(10)
<223> OTHER INFORMATION: Phe or Tyr

<400> SEQUENCE: 52

Xaa Gln Xaa Pro Xaa Xaa Xaa Xaa Xaa Xaa Trp Cys Asp Val
1               5                   10

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln Phe Pro
1

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Tyr Asn Asn Gly
1               5

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Gln Trp Pro Ser Ser Ser Asn Gly Arg Tyr Trp Cys Asp Val
```

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Phe Pro Ser Ser Trp Pro Phe Arg Tyr Trp Cys Asp Val
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gln Phe Pro Ser Trp Gly Asn Gly Arg Tyr Trp Cys Asp Val
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gln Phe Pro Ser Arg Phe Asn Gly Arg Tyr Trp Cys Asp Val
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Phe Pro Asn Arg Trp Asn Gly Arg Tyr Trp Cys Asp Val
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Phe Pro Ser Arg Asn Asn Gly Arg Tyr Trp Cys Asp Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic

```
                         peptide

<400> SEQUENCE: 61

Gln Gln Phe Pro Thr Arg Thr Asn Gly Arg Tyr Trp Cys Asp Val
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gln Phe Pro Ser Arg His Asn Gly Arg Tyr Trp Cys Asp Val
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Phe Pro Asn Pro Pro Asn Gly Arg Tyr Trp Cys Asp Val
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Phe Pro Ser Trp Phe Asn Gly Arg Tyr Trp Cys Asp Val
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Val
<220> FEATURE:
<221> NAME/KEY: MOD_RES
<222> LOCATION: (3)..(3)
<223> OTHER INFORMATION: Phe or Trp
<220> FEATURE:
<221> NAME/KEY: MOD_RES
<222> LOCATION: (5)..(5)
<223> OTHER INFORMATION: Ser, Asn or Thr
<220> FEATURE:
<221> NAME/KEY: MOD_RES
<222> LOCATION: (6)..(6)
<223> OTHER INFORMATION: Ser, Arg, Trp or Pro
<220> FEATURE:
<221> NAME/KEY: MOD_RES
<222> LOCATION: (7)..(7)
<223> OTHER INFORMATION: Ser, Trp, Phe, Gly, Asn, His, Thr or Pro
<220> FEATURE:
<221> NAME/KEY: MOD_RES
```

```
<222> LOCATION: (8)..(8)
<223> OTHER INFORMATION: Asn or Pro
<220> FEATURE:
<221> NAME/KEY: MOD_RES
<222> LOCATION: (9)..(9)
<223> OTHER INFORMATION: Gly or Phe

<400> SEQUENCE: 65

Xaa Gln Xaa Pro Xaa Xaa Xaa Xaa Xaa Arg Tyr Trp Cys Asp Val
1               5                   10                  15

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(4)
<223> OTHER INFORMATION: This region may encompass 0-4 residues
<220> FEATURE:
<221> NAME/KEY: MISC_FEATURE
<222> LOCATION: (5)..(8)
<223> OTHER INFORMATION: This region may encompass 0-4 residues
<220> FEATURE:
<221> NAME/KEY: MISC_FEATURE
<222> LOCATION: (9)..(12)
<223> OTHER INFORMATION: This region may encompass 0-4 residues
<220> FEATURE:
<221> NAME/KEY: MISC_FEATURE
<222> LOCATION: (13)..(16)
<223> OTHER INFORMATION: This region may encompass 0-4 residues
<220> FEATURE:
<221> NAME/KEY: MISC_FEATURE
<222> LOCATION: (17)..(20)
<223> OTHER INFORMATION: This region may encompass 0-4 residues
<220> FEATURE:
<221> NAME/KEY: MISC_FEATURE
<222> LOCATION: (21)..(24)
<223> OTHER INFORMATION: This region may encompass 0-4 residues
<220> FEATURE:
<221> NAME/KEY: MISC_FEATURE
<222> LOCATION: (25)..(28)
<223> OTHER INFORMATION: This region may encompass 0-4 residues
<220> FEATURE:
<221> NAME/KEY: MISC_FEATURE
<222> LOCATION: (29)..(32)
<223> OTHER INFORMATION: This region may encompass 0-4 residues
<220> FEATURE:
<221> NAME/KEY: MISC_FEATURE
<222> LOCATION: (1)..(32)
<223> OTHER INFORMATION: This sequence may encompass 0-4 (GlyxSerx)
      repeating units, wherein X is 0-4

<400> SEQUENCE: 66

Gly Gly Gly Gly Ser Ser Ser Ser Gly Gly Gly Gly Ser Ser Ser Ser
1               5                   10                  15

Gly Gly Gly Gly Ser Ser Ser Ser Gly Gly Gly Gly Ser Ser Ser Ser
            20                  25                  30

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Ala Tyr Ser Lys Ala Ala Thr Val Thr Gly Lys Leu
1               5                   10
```

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr His Asp Val Glu Leu Asn Leu
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Ala Tyr Ser Lys
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ser Thr Tyr Trp Tyr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Thr Val Asn Ala Arg Ser
1               5

<210> SEQ ID NO 72
<211> LENGTH: 6
<212> TYPE: PRT
<213> ORGANISM: Mus sp.

<400> SEQUENCE: 72

Gln Ser Asn Gly Asn Leu
1               5

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Val Val Gln Tyr Pro Ser Tyr Asn Asn Tyr Phe Trp Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 74

Val Xaa Xaa Xaa Pro Ser Tyr Asn Asn Tyr Phe Trp Cys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 75

Val Val Gln Xaa Xaa Xaa Tyr Asn Asn Tyr Phe Trp Cys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 76

Val Val Gln Tyr Pro Xaa Xaa Xaa Asn Tyr Phe Trp Cys

-continued

```
1               5                   10
```

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 77

```
Val Val Gln Tyr Pro Ser Tyr Xaa Xaa Xaa Phe Trp Cys
1               5                   10
```

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 78

```
Val Val Gln Tyr Pro Ser Tyr Asn Asn Xaa Xaa Xaa Cys
1               5                   10
```

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Val Gln Gln Phe Pro Ser Ser Ser Asn Gly Arg Tyr Trp Cys
1               5                   10
```

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)

```
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 80

Val Xaa Xaa Xaa Pro Ser Ser Ser Asn Gly Arg Tyr Trp Cys
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 81

Val Gln Gln Xaa Xaa Xaa Ser Ser Asn Gly Arg Tyr Trp Cys
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 82

Val Gln Gln Phe Pro Xaa Xaa Xaa Asn Gly Arg Tyr Trp Cys
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
```

```
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 83

Val Gln Gln Phe Pro Ser Ser Xaa Xaa Xaa Arg Tyr Trp Cys
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 84

Val Gln Gln Phe Pro Ser Ser Ser Asn Xaa Xaa Xaa Trp Cys
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Gln Tyr Pro Ser Tyr Asn Asn Tyr Phe Trp Cys
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Phe Pro Ser Ser Ser Asn Gly Arg Tyr Trp Cys
1               5                   10

<210> SEQ ID NO 87
<211> LENGTH: 11
<212> TYPE: PRT
<213> ORGANISM: Homo sapiens

<400> SEQUENCE: 87

Gly Tyr Val Ala Tyr Ser Lys Ala Ala Thr Val
1               5                   10
```

<210> SEQ ID NO 88
<211> LENGTH: 11
<212> TYPE: PRT
<213> ORGANISM: Homo sapiens

<400> SEQUENCE: 88

Val Ile Lys Leu Thr His Asp Val Glu Leu Asn
1               5                   10

<210> SEQ ID NO 89
<211> LENGTH: 239
<212> TYPE: PRT
<213> ORGANISM: Homo sapiens

<400> SEQUENCE: 89

Ser Lys Val Trp Arg Asp Gln His Phe Val Lys Ile Gln Val Lys Asp
1               5                   10                  15

Ser Ala Gln Asn Ser Val Ile Ile Val Asp Lys Asn Gly Arg Leu Val
            20                  25                  30

Tyr Leu Val Glu Asn Pro Gly Gly Tyr Val Ala Tyr Ser Lys Ala Ala
        35                  40                  45

Thr Val Thr Gly Lys Leu Val His Ala Asn Phe Gly Thr Lys Lys Asp
    50                  55                  60

Phe Glu Asp Leu Tyr Thr Pro Val Asn Gly Ser Ile Val Ile Val Arg
65                  70                  75                  80

Ala Gly Lys Ile Thr Phe Ala Glu Lys Val Ala Asn Ala Glu Ser Leu
                85                  90                  95

Asn Ala Ile Gly Val Leu Ile Tyr Met Asp Gln Thr Lys Phe Pro Ile
            100                 105                 110

Val Asn Ala Glu Leu Ser Phe Phe Gly His Ala His Leu Gly Thr Gly
        115                 120                 125

Asp Pro Tyr Thr Pro Gly Phe Pro Ser Phe Asn His Thr Gln Phe Pro
    130                 135                 140

Pro Ser Arg Ser Ser Gly Leu Pro Asn Ile Pro Val Gln Thr Ile Ser
145                 150                 155                 160

Arg Ala Ala Ala Glu Lys Leu Phe Gly Asn Met Glu Gly Asp Cys Pro
                165                 170                 175

Ser Asp Trp Lys Thr Asp Ser Thr Cys Arg Met Val Thr Ser Glu Ser
            180                 185                 190

Lys Asn Val Lys Leu Thr Val Ser Asn Val Leu Lys Glu Ile Lys Ile
        195                 200                 205

Leu Asn Ile Phe Gly Val Ile Lys Gly Phe Val Glu Pro Asp His Tyr
    210                 215                 220

Val Val Val Gly Ala Gln Arg Asp Ala Trp Gly Pro Gly Ala Ala
225                 230                 235

<210> SEQ ID NO 90
<211> LENGTH: 240
<212> TYPE: PRT
<213> ORGANISM: Mus musculus

<400> SEQUENCE: 90

Ser Lys Val Trp Arg Asp Glu His Tyr Val Lys Ile Gln Val Lys Ser
1               5                   10                  15

Ser Ile Gly Gln Asn Met Val Thr Ile Val Gln Ser Asn Gly Asn Leu
            20                  25                  30

Asp Pro Val Glu Ser Pro Glu Gly Tyr Val Ala Phe Ser Lys Pro Thr

```
                35                  40                  45
Glu Val Ser Gly Lys Leu Val His Ala Asn Phe Gly Thr Lys Lys Asp
 50                  55                  60

Phe Glu Glu Leu Ser Tyr Ser Val Asn Gly Ser Leu Val Ile Val Arg
 65                  70                  75                  80

Ala Gly Glu Ile Thr Phe Ala Glu Lys Val Ala Asn Ala Gln Ser Phe
                 85                  90                  95

Asn Ala Ile Gly Val Leu Ile Tyr Met Asp Lys Asn Lys Phe Pro Val
            100                 105                 110

Val Glu Ala Asp Leu Ala Leu Phe Gly His Ala His Leu Gly Thr Gly
        115                 120                 125

Asp Pro Tyr Thr Pro Gly Phe Pro Ser Phe Asn His Thr Gln Phe Pro
    130                 135                 140

Pro Ser Gln Ser Ser Gly Leu Pro Asn Ile Pro Val Gln Thr Ile Ser
145                 150                 155                 160

Arg Ala Ala Ala Glu Lys Leu Phe Gly Lys Met Glu Gly Ser Cys Pro
                165                 170                 175

Ala Arg Trp Asn Ile Asp Ser Ser Cys Lys Leu Glu Leu Ser Gln Asn
            180                 185                 190

Gln Asn Val Lys Leu Ile Val Lys Asn Val Leu Lys Glu Arg Arg Ile
        195                 200                 205

Leu Asn Ile Phe Gly Val Ile Lys Gly Tyr Glu Glu Pro Asp Arg Tyr
    210                 215                 220

Val Val Val Gly Ala Gln Arg Asp Ala Leu Gly Ala Gly Val Ala Ala
225                 230                 235                 240

<210> SEQ ID NO 91
<211> LENGTH: 60
<212> TYPE: PRT
<213> ORGANISM: Homo sapiens

<400> SEQUENCE: 91

Leu Val His Ala Asn Phe Gly Thr Lys Lys Asp Phe Glu Asp Leu Tyr
 1               5                  10                  15

Thr Pro Val Asn Gly Ser Ile Val Ile Val Arg Ala Gly Lys Ile Thr
                20                  25                  30

Phe Ala Glu Lys Val Ala Asn Ala Glu Ser Leu Asn Ala Ile Gly Val
            35                  40                  45

Leu Ile Tyr Met Asp Gln Thr Lys Phe Pro Ile Val
 50                  55                  60

<210> SEQ ID NO 92
<211> LENGTH: 60
<212> TYPE: PRT
<213> ORGANISM: Mus musculus

<400> SEQUENCE: 92

Leu Val His Ala Asn Phe Gly Thr Lys Lys Asp Phe Glu Glu Leu Ser
 1               5                  10                  15

Tyr Ser Val Asn Gly Ser Leu Val Ile Val Arg Ala Gly Glu Ile Thr
                20                  25                  30

Phe Ala Glu Lys Val Ala Asn Ala Gln Ser Phe Asn Ala Ile Gly Val
            35                  40                  45

Leu Ile Tyr Met Asp Lys Asn Lys Phe Pro Val Val
 50                  55                  60
```

```
<210> SEQ ID NO 93
<211> LENGTH: 60
<212> TYPE: PRT
<213> ORGANISM: Rattus norvegicus

<400> SEQUENCE: 93

Leu Val His Ala Asn Phe Gly Thr Lys Lys Asp Phe Glu Glu Leu Asn
1               5                   10                  15

Tyr Ser Val Asn Gly Ser Leu Val Ile Val Arg Ala Gly Lys Ile Thr
            20                  25                  30

Phe Ala Glu Lys Val Ala Asn Ala Gln Ser Phe Asn Ala Ile Gly Val
        35                  40                  45

Leu Ile Tyr Met Asp Arg Asn Thr Phe Pro Val Val
    50                  55                  60

<210> SEQ ID NO 94
<211> LENGTH: 60
<212> TYPE: PRT
<213> ORGANISM: Sus scrofa

<400> SEQUENCE: 94

Leu Ile Phe Ala Asn Phe Gly Thr Lys Lys Asp Phe Glu Asp Leu Lys
1               5                   10                  15

Met Pro Val Asn Gly Ser Leu Val Ile Val Arg Ala Gly Lys Ile Thr
            20                  25                  30

Phe Ala Glu Lys Val Ala Asn Ala Gln Ser Leu Asp Ala Ile Gly Val
        35                  40                  45

Leu Ile Tyr Met Asp Arg Ala Asn Phe Pro Ile Ile
    50                  55                  60

<210> SEQ ID NO 95
<211> LENGTH: 60
<212> TYPE: PRT
<213> ORGANISM: Macaca mulatta

<400> SEQUENCE: 95

Leu Val His Ala Asn Phe Gly Thr Lys Lys Asp Phe Glu Asp Leu Asp
1               5                   10                  15

Ser Pro Val Asn Gly Ser Ile Val Ile Val Arg Ala Gly Lys Ile Thr
            20                  25                  30

Phe Ala Glu Lys Val Ala Asn Ala Glu Ser Leu Asn Ala Ile Gly Val
        35                  40                  45

Leu Ile Tyr Met Asp Gln Thr Lys Phe Pro Ile Val
    50                  55                  60
```